United States Patent
Yamaguchi et al.

(10) Patent No.: US 10,011,576 B2
(45) Date of Patent: *Jul. 3, 2018

(54) ACTINIC RAY-SENSITIVE OR RADIATION-SENSITIVE RESIN COMPOSITION, ACTINIC RAY-SENSITIVE OR RADIATION-SENSITIVE FILM, MASK BLANK PROVIDED WITH ACTINIC RAY-SENSITIVE OR RADIATION-SENSITIVE FILM, PATTERN FORMING METHOD, METHOD FOR MANUFACTURING ELECTRONIC DEVICE, ELECTRONIC DEVICE, AND COMPOUND

(71) Applicant: FUJIFILM Corporation, Tokyo (JP)

(72) Inventors: Shuhei Yamaguchi, Shizuoka (JP);
Koutarou Takahashi, Shizuoka (JP);
Tomotaka Tsuchimura, Shizuoka (JP);
Natsumi Yokokawa, Shizuoka (JP);
Hidehiro Mochizuki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/176,810

(22) Filed: Jun. 8, 2016

(65) Prior Publication Data

US 2016/0280675 A1    Sep. 29, 2016

Related U.S. Application Data

(63) Continuation of application No. PCT/JP2015/050631, filed on Jan. 13, 2015.

(30) Foreign Application Priority Data

Feb. 18, 2014    (JP) .................. 2014-028890

(51) Int. Cl.
*G03F 7/039* (2006.01)
*G03F 7/004* (2006.01)
(Continued)

(52) U.S. Cl.
CPC ............ *C07D 307/33* (2013.01); *C08F 12/24* (2013.01); *C08F 112/14* (2013.01);
(Continued)

(58) Field of Classification Search
None
See application file for complete search history.

(56) References Cited

U.S. PATENT DOCUMENTS 5,422,221 A    6/1995  Okazaki et al.
5,663,246 A *  9/1997  Spaltenstein ............ C08G 8/36
                                                       525/398
(Continued)

FOREIGN PATENT DOCUMENTS

JP    5-216234 A    8/1993
JP    06-242602 A   9/1994
(Continued)

OTHER PUBLICATIONS

Machine translation of JP 11-254850 (1999).*
(Continued)

*Primary Examiner* — Martin J Angebranndt
(74) *Attorney, Agent, or Firm* — Sughrue Mion, PLLC

(57) ABSTRACT

The actinic ray-sensitive or radiation-sensitive resin composition includes a crosslinking agent having a polarity converting group and an alkali-soluble resin, in which the polarity converting group is a group capable of decomposing by the action of an alkaline aqueous solution to generate a carboxylic acid or sulfonic acid on the side having a crosslinking group.

11 Claims, 2 Drawing Sheets

(51) Int. Cl.
*G03F 7/20* (2006.01)
*G03F 7/32* (2006.01)
*C07D 307/33* (2006.01)
*C08F 12/24* (2006.01)
*C08F 112/14* (2006.01)
*C08F 212/32* (2006.01)
*G03F 7/038* (2006.01)
*C08F 212/14* (2006.01)
*C09D 125/18* (2006.01)
*G03F 1/50* (2012.01)
*C08F 12/22* (2006.01)

(52) U.S. Cl.
CPC .......... *C08F 212/14* (2013.01); *C09D 125/18* (2013.01); *G03F 1/50* (2013.01); *G03F 7/004* (2013.01); *G03F 7/038* (2013.01); *G03F 7/2004* (2013.01); *G03F 7/2059* (2013.01); *G03F 7/322* (2013.01); *C08F 12/22* (2013.01)

(56) References Cited

U.S. PATENT DOCUMENTS

| | | | | |
|---|---|---|---|---|
| 6,384,169 | B1 * | 5/2002 | Watanabe | G03F 7/039 430/270.1 |
| 8,163,443 | B2 | 4/2012 | Tomari et al. | |
| 9,718,901 | B2 * | 8/2017 | Tsuruta | C08F 12/24 |
| 9,904,168 | B2 * | 2/2018 | Yokokawa | G03F 7/038 |
| 2002/0061462 | A1 | 5/2002 | Uenishi | |
| 2003/0215734 | A1 | 11/2003 | Tsuihiji et al. | |
| 2006/0199099 | A1 | 9/2006 | Arao et al. | |
| 2009/0130568 | A1 | 5/2009 | Tomari et al. | |
| 2010/0298491 | A1 | 11/2010 | Okada et al. | |
| 2014/0072915 | A1 * | 3/2014 | Chen | G03F 7/0397 430/325 |
| 2015/0086911 | A1 | 3/2015 | Tsuruta et al. | |
| 2015/0118623 | A1 * | 4/2015 | Tsuruta | C08F 212/14 430/286.1 |
| 2016/0282720 | A1 * | 9/2016 | Takahashi | G03F 7/0382 |
| 2016/0320700 | A1 * | 11/2016 | Yokokawa | G03F 7/038 |

FOREIGN PATENT DOCUMENTS

| | | | |
|---|---|---|---|
| JP | 9268185 | A | 10/1997 |
| JP | 1017562 | A | 1/1998 |
| JP | 10-268515 | A | 10/1998 |
| JP | 11-254850 | A | 9/1999 |
| JP | 2000-147752 | * | 5/2000 |
| JP | 2000-330282 | A | 11/2000 |
| JP | 2002-6500 | A | 1/2002 |
| JP | 2002-148806 | A | 5/2002 |
| JP | 2003-327646 | A | 11/2003 |
| JP | 2004-29680 | A | 1/2004 |
| JP | 2005099105 | A | 4/2005 |
| JP | 2006-243161 | A | 9/2006 |
| JP | 2007045736 | A | 2/2007 |
| JP | 2007-084502 | * | 4/2007 |
| JP | 2008064963 | A | 3/2008 |
| JP | 2008076967 | A | 4/2008 |
| JP | 2008-268935 | A | 11/2008 |
| JP | 2009-162871 | A | 7/2009 |
| JP | 2009-227697 | * | 10/2009 |
| JP | 2009-237167 | * | 10/2009 |
| JP | 2010237274 | A | 10/2010 |
| JP | 2012014021 | A | 1/2012 |
| JP | 2012-241053 | A | 12/2012 |
| JP | 2014-16478 | A | 1/2014 |
| JP | 2014-24999 | A | 2/2014 |
| TW | 201403227 | A | 1/2014 |
| TW | 201404789 | A | 2/2014 |
| WO | 2007/086324 | A1 | 8/2007 |
| WO | 2007102470 | A1 | 9/2007 |
| WO | 2012-132676 | * | 10/2012 |
| WO | 2013/176063 | * | 11/2013 |
| WO | 2014/017268 | * | 1/2014 ............. G03F 7/039 |

OTHER PUBLICATIONS

Machine translation of JP 2009-237167 (2009).*
International Search Report of PCT/JP2015/050631 dated Apr. 14, 2015.
Written Opinion of PCT/JP2015/050631 dated Apr. 14, 2015.
International Preliminary Report on Patentability dated Aug. 23, 2016, in International Application No. PCT/JP2015/050631, with English translation of Written Opinion, 22 pages in English and Japanese.
Communication dated Feb. 14, 2017, issued from the Japanese Patent Office in corresponding Application No. 2014-028890.
Communication dated May 1, 2017, issued by the Korean Intellectual Property Office in corresponding Korean Application No. 10-2016-7015309.
Communication dated May 16, 2017, from the Japanese Patent Office in counterpart application No. 2014-028890.
Yeong-Deuk Shin et al. "Novel thermally degradable diepoxy crosslinkers containing sulfonate ester groups for photo-crosslinking," Polymer Degradation and Stability vol. 86 (2004) pp. 153-158.
Office Action dated Apr. 11, 2018 issued by the Intellectual Property Office of Taiwan in counterpart Taiwanese Application No. 104102173.

* cited by examiner

ACTINIC RAY-SENSITIVE OR RADIATION-SENSITIVE RESIN COMPOSITION, ACTINIC RAY-SENSITIVE OR RADIATION-SENSITIVE FILM, MASK BLANK PROVIDED WITH ACTINIC RAY-SENSITIVE OR RADIATION-SENSITIVE FILM, PATTERN FORMING METHOD, METHOD FOR MANUFACTURING ELECTRONIC DEVICE, ELECTRONIC DEVICE, AND COMPOUND

CROSS-REFERENCE TO RELATED APPLICATIONS

This application is a Continuation of PCT International Application No. PCT/JP2015/50631, filed on Jan. 13, 2015, which claims priority under 35 U.S.C. § 119(a) to Japanese Patent Application No. 2014-028890, filed on Feb. 18, 2014. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition which is suitably used in an ultramicrolithographic process which is applicable to a production process such as a production process of ultra-large scale integrations (LSIs) and high capacity microchips, a manufacturing process of a nanoimprint mold, and a production process of a high density information recording medium, and other photofabrication processes, as well as an actinic ray-sensitive or radiation-sensitive film, a mask blank provided with the actinic ray-sensitive or radiation-sensitive film, a pattern forming method, a method for manufacturing an electronic device, an electronic device, and a novel compound. More particularly, the present invention relates to an actinic ray-sensitive or radiation-sensitive resin composition which can be suitably used for microfabrication of a semiconductor device using an electron beam, X-rays, or EUV light, as well as an actinic ray-sensitive or radiation-sensitive film, a mask blank provided with the actinic ray-sensitive or radiation-sensitive film, a pattern forming method, a method for manufacturing an electronic device, an electronic device, and a novel compound.

2. Description of the Related Art

In microfabrication using a resist composition, formation of an ultrafine pattern is required due to an increase in the integration degree of an integrated circuit. Accordingly, there is an additional tendency that the exposure wavelength becomes shorter, such as from g line to i line, or further to KrF laser light or ArF laser light. Further, lithography using an electron beam, X-rays, or EUV light instead of excimer laser light has recently been under development.

However, from the viewpoint of overall performance of a resist, it remains very difficult to find a suitable combination of a resin, a photoacid generator, a basic compound, an additive, a solvent, and the like to be used. In particular, upon considering recent demand for the formation of an ultrafine pattern (for example, one having a line width of 50 nm or less) with high performance, it cannot be yet said that currently available lithography is sufficient in terms of its performance.

Typically, even in the case of providing an unexposed area intended to be removed by a developer and an exposed area not intended to be removed by a developer on a resist film when performing exposure, a region within the unexposed area being adjacent to the exposed area is subjected to exposure even in a low exposure dose (hereinafter, this region is referred to as "weakly exposed area"). Therefore, even a weakly exposed area becomes insoluble or poorly-soluble in connection with a developer, which, in turn, leads to occurrence of scum and bridging between patterns formed by the development.

In the field of an electron beam (EB) lithography, it has been found that the influence of electron scattering in a resist film (that is, forward scattering) is reduced by increasing the acceleration voltage of an EB. Accordingly, there has been recently a tendency to increase the acceleration voltage of an EB. However, if the acceleration voltage of an EB is increased, the influence of forward scattering is reduced, whereas the influence of scattering of electrons reflected in a resist substrate (that is, backward scattering) is increased. In addition, in the case of forming an isolated space pattern having a large exposure area, the influence of backward scattering is particularly significant. Thus, for example, an increase in the acceleration voltage of an EB may possibly result in occurrence of scum and bridging between isolated space patterns.

Particularly, in the case of patterning on a photomask blank used for semiconductor exposure, since a light-shielding film containing heavy atoms such as chromium, molybdenum, and tantalum is present as a layer below a resist film, the influence of backward scattering due to reflection from a layer below a resist film is more significant in comparison to the case of applying a resist onto a silicon wafer. As a consequence, in the case of forming an isolated space pattern on a photomask blank, the pattern is particularly susceptible to the influence of backward scattering, and the resolution thereof is highly likely to decrease. On the other hand, in extreme ultraviolet (EUV) lithography, there is a possibility of generating scum and bridging between patterns, due to the flare light generated by the surface topology and a phase difference of a reflection mirror constituting an optical system of an exposure apparatus, and the unintended light of different wavelengths (Out of Band light: OoB light) from that of EUV light, which is generated due to the reflection mirror also exhibiting a certain degree of reflection characteristics with respect to wavelengths different from an exposure wavelength of EUV light (typically 13.5 nm).

Further, microfabrication using a resist composition is not only used directly in the production of integrated circuits but has also been recently applied to the fabrication or the like of a so-called imprint mold structure (see, for example, JP2002-148806A, JP2008-268935A, JP2002-6500A, and SPIE Vol. 1672 (1992) 157). To this end, in particular, even in a case of forming an ultrafine pattern (for example, one having a line width of 50 nm or less) using X-rays, soft X-rays, or an electron beam as an exposure light source, it has become an important task to simultaneously provide a performance capable of inhibiting occurrence of scum and bridging, in addition to providing a favorable resist performance such as having a high resolution and good roughness characteristics. There is a need in the art for solving these desired requirements.

SUMMARY OF THE INVENTION

An object of the present invention is to provide an actinic ray-sensitive or radiation-sensitive resin composition which is capable of forming a pattern inhibiting occurrence of scum and bridging, having excellent resolution, and achieving low line edge roughness (LER), as well as an actinic ray-sensitive or radiation-sensitive film, a mask blank having the same film, and a pattern forming method, each using the composition.

Another object of the present invention is to provide an actinic ray-sensitive or radiation-sensitive resin composition which exhibits excellent line edge roughness (LER) performance, scum performance, and bridging performance, particularly in the formation of an ultrafine pattern (for example, one having a line width of 50 nm or less) by exposure using an electron beam or extreme ultraviolet rays, as well as an actinic ray-sensitive or radiation-sensitive film, a mask blank having the same film, and a pattern forming method, each using the composition.

A still another object of the present invention is to provide a method for manufacturing an electronic device including the above-mentioned pattern forming method, and an electronic device.

In one embodiment, the present invention is as follows.

[1] An actinic ray-sensitive or radiation-sensitive resin composition, comprising a crosslinking agent having a polarity converting group, and an alkali-soluble resin, in which the polarity converting group is a group capable of decomposing by the action of an alkaline aqueous solution to generate a carboxylic acid or sulfonic acid on a side having the crosslinking group.

[2] The actinic ray-sensitive or radiation-sensitive resin composition according to [1], in which the crosslinking agent is a compound represented by General Formula (1), or a compound in which two to five structures represented by General Formula (1) are connected via a linking group or a single bond represented by L in General Formula (3).

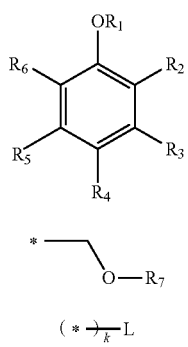

In General Formula (1), each of $R_1$ to $R_6$ independently represents a hydrogen atom, an organic group having 1 to 50 carbon atoms, or a binding site to a linking group or a single bond represented by L in General Formula (3), provided that at least one of $R_2$ to $R_6$ is a structure represented by General Formula (2), and at least one of $R_1$ to $R_6$ is a polarity converting group, or a group having the polarity converting group as a partial structure.

In General Formula (2), $R_7$ represents a hydrogen atom or an organic group having 1 to 30 carbon atoms, and * represents a binding site in any one of $R_2$ to $R_6$.

In General Formula (3), L represents a linking group or a single bond, * represents a binding site in any one of $R_1$ to $R_6$, and k is an integer of 2 to 5.

[3] The actinic ray-sensitive or radiation-sensitive resin composition according to [2], in which the linking group L in General Formula (3) is a group selected from an alkylene group, an arylene group, a carboxylic acid ester bond, an ether bond, and combinations thereof.

[4] The actinic ray-sensitive or radiation-sensitive resin composition according to any one of [1] to [3], in which the polarity converting group is any one selected from the group consisting of structures represented by the following General Formulae (4) to (8).

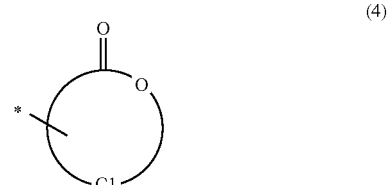

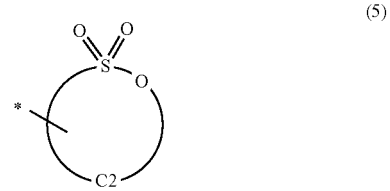

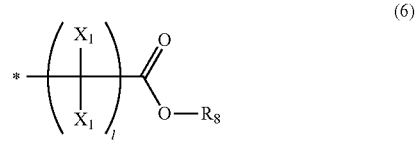

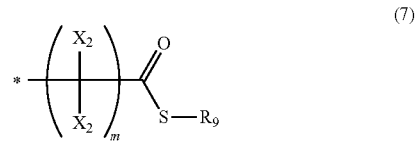

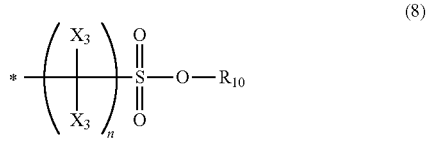

In General Formula (4), C1 represents a hydrocarbon group having 1 to 15 carbon atoms and forms a monocyclic or polycyclic ring together with the —COO— group in the formula.

In General Formula (5), C2 represents a hydrocarbon group having 1 to 15 carbon atoms and forms a monocyclic or polycyclic ring together with the —SO$_3$— group in the formula.

In General Formula (6), each $X_1$ independently represents a hydrogen atom or a substituent, $R_8$ represents an alkyl group or an aryl group, and l represents an integer of 0 to 7, provided that in the case where $R_8$ is an alkyl group, the structure represented by General Formula (6) has at least one electron withdrawing group, and in the case where $R_8$ in this case is an alkyl group which does not have an electron withdrawing group, l is 1 or more, and at least one $X_1$ is an electron withdrawing group.

In General Formula (7), each $X_2$ independently represents a hydrogen atom or a substituent, $R_9$ represents an alkyl group or an aryl group, and m represents an integer of 0 to 7.

In General Formula (8), each $X_3$ independently represents a hydrogen atom or a substituent, $R_{10}$ represents an alkyl group or an aryl group, and n represents an integer of 0 to 7.

In General Formulae (4) to (8), * represents a binding site in any one of $R_1$ to $R_6$.

[5] The actinic ray-sensitive or radiation-sensitive resin composition according to any one of [1] to [4], in which the alkali-soluble resin includes a repeating unit represented by the following General Formula (II).

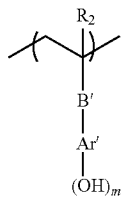

(II)

In the formula, $R_2$ represents a hydrogen atom, a methyl group which may have a substituent, or a halogen atom.

B' represents a single bond or a divalent organic group.

Ar' represents an aromatic ring group.

m represents an integer of 1 or more.

[6] The actinic ray-sensitive or radiation-sensitive resin composition according to [5], in which the alkali-soluble resin includes at least a repeating unit represented by the following General Formula (12), as the repeating unit represented by General Formula (II).

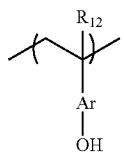

(12)

In General Formula (12), $R_{12}$ represents a hydrogen atom or a methyl group.

Ar represents an aromatic ring group.

[7] The actinic ray-sensitive or radiation-sensitive resin composition according to any one of [1] to [6], further comprising a basic compound or ammonium salt compound whose basicity is decreased upon irradiation with actinic rays or radiation.

[8] An actinic ray-sensitive or radiation-sensitive film comprised of the actinic ray-sensitive or radiation-sensitive resin composition according to any one of [1] to [7].

[9] A mask blank provided with the actinic ray-sensitive or radiation-sensitive film according to [8].

[10] A pattern forming method, comprising:

a step of forming the actinic ray-sensitive or radiation-sensitive film according to [8];

a step of exposing the film; and a step of developing the exposed film using a developer to form a pattern.

[11] The pattern forming method according to [10], in which the exposure is carried out using X-rays, an electron beam, or EUV.

[12] A method for manufacturing an electronic device, comprising the pattern forming method according to [10] or [11].

[13] An electronic device manufactured by the method for manufacturing an electronic device according to [12].

[14] A compound represented by the following General Formula (1), or a compound in which two or three structures represented by General Formula (1) are connected via a linking group or a single bond represented by L in General Formula (3a).

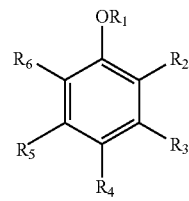

(1)

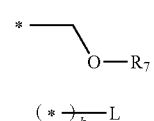

(2)

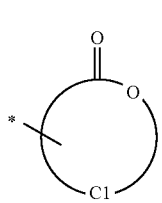

(3a)

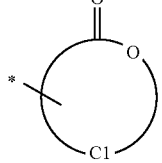

(4)

In General Formula (1), each of $R_1$ to $R_6$ independently represents a hydrogen atom, an organic group having 1 to 50 carbon atoms, or a binding site to a linking group or a single bond represented by L in General Formula (3a), provided that at least one of $R_2$ to $R_6$ is a structure represented by General Formula (2), and at least one of $R_1$ to $R_6$ is a structure represented by General Formula (4), or a group containing the structure represented by General Formula (4).

In General Formula (2), $R_7$ represents a hydrogen atom or an organic group having 1 to 30 carbon atoms, and * represents a binding site in any one of $R_2$ to $R_6$.

In General Formula (3a), L represents a linking group or a single bond, * represents a binding site in any one of $R_1$ to $R_6$, and $k_1$ is 2 or 3.

In General Formula (4), C1 represents a hydrocarbon group having 1 to 15 carbon atoms and forms a monocyclic or polycyclic ring together with a —COO— group in the formula.

According to the present invention, it has become possible to provide an actinic ray-sensitive or radiation-sensitive resin composition which is capable of forming a pattern inhibiting occurrence of scum and bridging, having excellent resolution, and achieving low line edge roughness (LER), as well as an actinic ray-sensitive or radiation-sensitive film, a mask blank having the same film, and a pattern forming method, each using the composition. Further, according to the present invention, it has become possible to provide a method for manufacturing an electronic device including the above-mentioned pattern forming method, and an electronic device.

DESCRIPTION OF THE PREFERRED EMBODIMENTS

Figure 1:
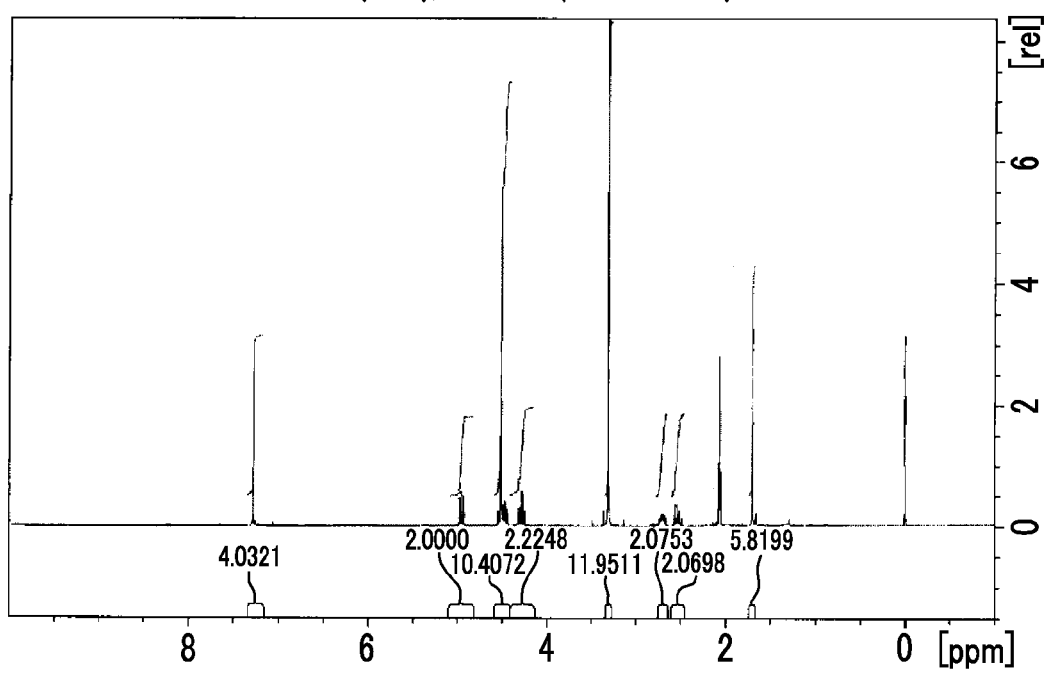
FIG. 1 shows an NMR chart ($^1$HNMR, acetone-d6) of a crosslinking agent (C-1) synthesized in Examples.

In the description of the present invention, when a group (atomic group) is denoted without specifying whether substituted or unsubstituted, the group includes both a group having no substituent and a group having a substituent. For example, "an alkyl group" includes not only an alkyl group having no substituent (unsubstituted alkyl group) but also an alkyl group having a substituent (substituted alkyl group).

Incidentally, the term "actinic rays" or "radiation" as used herein indicates, for example, a bright line spectrum of mercury lamp, far ultraviolet rays typified by excimer laser, extreme ultraviolet rays (EUV light), X-rays, or an electron beam (EB). Also, in the present invention, the "light" means actinic rays or radiation.

Furthermore, unless otherwise indicated, the term "exposure" as used herein includes not only exposure to a mercury lamp, far ultraviolet rays represented by excimer laser, extreme ultraviolet rays (EUV light), X-rays, or the like but also lithography with a particle beam such as an electron beam and an ion beam.

Hereinafter, embodiments of the present invention will be described in more detail.

<Crosslinking Agent>

The actinic ray-sensitive or radiation-sensitive resin composition of the present invention contains a crosslinking agent (hereinafter referred to also as "crosslinking agent of the present invention" or "crosslinking agent (C)") having "a group capable of decomposing by the action of an alkaline aqueous solution to generate a carboxylic acid or sulfonic acid on the side having a crosslinking group (hereinafter referred to as "polarity converting group")". The polarity converting group contained in the crosslinking agent of the present invention exhibits a greater change of hydrophilicity before alkali development to hydrophobicity after hydrolysis by alkali development, as compared to that of a phenolic hydroxyl group in a compound which has been conventionally used as a crosslinking agent. This is believed to greatly contribute to increased dissolution contrast in a weakly exposed area, consequently becoming possible to improve the roughness characteristics and resolution, and also to inhibit the occurrence of scum and bridging caused by the residual error from weakly exposed areas. The crosslinking agent of the present invention having a polarity converting group is particularly effective in weakly exposed areas, since the polymerization of a crosslinking agent is partially in progress therein.

The polarity converting group contained in the crosslinking agent of the present invention, as described above, is a group capable of decomposing by the action of an alkaline aqueous solution to generate a carboxylic acid or sulfonic acid on the side having a crosslinking group. Specifically, the crosslinking agent has a crosslinking group and a polarity converting group. The polarity converting group interacts with an alkaline aqueous solution, and consequently the crosslinking agent has a crosslinking group and a carboxylic acid or sulfonic acid in one molecule. In the present invention, the term "crosslinking group" is a group which insolubilizes exposed areas by newly forming chemical bonds in the system by the action of active species such as an acid, generated upon irradiation with actinic rays or radiation. The crosslinking group is, for example, a group represented by —CH$_2$—O—R$_7$ as General Formula (2) described later.

The number of polarity converting groups in the crosslinking agent (C) is, in one embodiment of the present invention, preferably 1 to 6, and more preferably 1 to 3.

In one embodiment of the present invention, the polarity converting group is preferably a group represented by any one of the following General Formulae (4) to (8), and from the viewpoint of, for example, dissolution contrast, more preferably a group represented by General Formula (4).

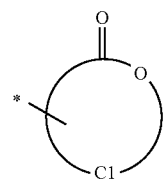

(4)

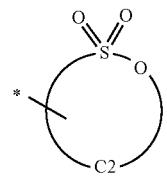

(5)

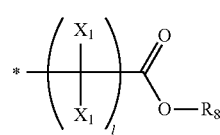

(6)

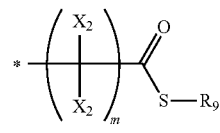

(7)

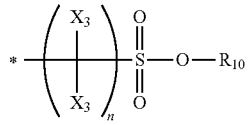

(8)

In General Formula (4), C1 represents a hydrocarbon group having 1 to 15 carbon atoms and forms a monocyclic or polycyclic ring together with the —COO— group in the formula.

In General Formula (5), C2 represents a hydrocarbon group having 1 to 15 carbon atoms and forms a monocyclic or polycyclic ring together with the —SO$_3$— group in the formula.

In General Formula (6), each X$_1$ independently represents a hydrogen atom or a substituent, R$_8$ represents an alkyl group or an aryl group, and l represents an integer of 0 to 7, provided that in the case where R$_8$ is an alkyl group, the structure represented by General Formula (6) has at least one electron withdrawing group, and in the case where R$_8$ in this case is an alkyl group which does not have an electron withdrawing group, l is 1 or more and at least one X$_1$ is an electron withdrawing group.

In General Formula (7), each X$_2$ independently represents a hydrogen atom or a substituent, R$_9$ represents an alkyl group or an aryl group, and m represents an integer of 0 to 7.

In General Formula (8), each X$_3$ independently represents a hydrogen atom or a substituent, R$_{10}$ represents an alkyl group or an aryl group, and n represents an integer of 0 to 7.

In General Formulae (4) to (8), * represents a binding site in any one of R$_1$ to R$_6$.

General Formula (4) will be described in more detail.

Examples of the monocyclic or polycyclic ring, which is formed by the hydrocarbon group having 1 to 15 carbon atoms represented by C1 together with the —COO— group in the formula, include a 5- to 7-membered ring lactone structure, and a structure in which a bicyclo structure and a spiro structure are formed in a 5- to 7-membered ring lactone structure and another monocyclic or polycyclic structure is condensed thereto. The monocyclic and polycyclic ring may further have a substituent, and may contain a heteroatom as a ring-constituting atom.

General Formula (5) will be described in more detail.

Examples of the monocyclic or polycyclic ring, which is formed by the hydrocarbon group having 1 to 15 carbon atoms represented by C2 together with the —SO$_3$— group in the formula, include a 5- to 7-membered ring sultone structure, and a structure in which a bicyclo structure and a spiro structure are formed in a 5- to 7-membered ring sultone structure and another monocyclic or polycyclic structure is condensed thereto. The monocyclic and polycyclic ring may further have a substituent, and may contain a heteroatom as a ring-constituting atom.

General Formula (6) will be described in more detail.

The group represented by General Formula (6) has at least one electron withdrawing group.

Here, the electron withdrawing group is a functional group having a σ$_m$ value of Hammett's rule (Ref: Hansch et al., Chemical Reviews, 1991, Vol. 91, No. 2, 165-195) of 0 or more, preferably a functional group having a σ$_m$ value of Hammett's rule of +0.1 or more.

Specific examples of the electron withdrawing group include a halogen atom such as a fluorine atom, a chlorine atom, or a bromine atom, a mercapto group, a hydroxy group, an alkoxy group (a methoxy group, an ethoxy group, an isopropoxy group, t-butoxy group, a benzyl group, and the like), a cyano group, a nitro group, an alkylsulfonyl group, an arylsulfonyl group, alkoxysulfonyl group, aryloxysulfonyl group, an alkoxycarbonyl group, an aryloxycarbonyl group, an acyloxy group, an acyl group, a vinyl group, and an alkyl group having these groups (for example, a trifluoromethyl group), and an aryl group (for example, pentafluorophenyl group).

Examples of the substituent represented by X$_1$ include an alkyl group, a cycloalkyl group, and an electron withdrawing group.

Examples of the alkyl group represented by X$_1$ include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group. The alkyl group may have a substituent.

Examples of the cycloalkyl group represented by X$_1$ include cyclopropyl, cyclobutyl, cyclopentyl, cyclohexyl, cycloheptyl, cyclooctyl, cyclododecanyl, cyclopentenyl, cyclohexenyl, cyclooctadienyl, bicyclo[4.3.0]nonanyl, decahydronaphthalenyl, tricyclo[5.2.1.0$^{2,6}$]decanyl, bornyl, isobornyl, norbornyl, adamantyl, noradamantyl, 1,7,7-trimethylcyclo[2.2.1.0$^{2,6}$]heptanyl, and 3,7,7-trimethylbicyclo[4.1.0]heptanyl. The cycloalkyl group may have a substituent.

The electron withdrawing group represented by X$_1$ is as described above.

Examples of the alkyl group represented by R$_8$ include the same specific examples as the alkyl group represented by X$_1$. The alkyl group may have a substituent, and may have, for example, an electron withdrawing group as a substituent. In the case where R$_8$ is not an alkyl group having an electron withdrawing group, l in General Formula (6) is one or more, and at least one X$_1$ is an electron withdrawing group.

Examples of the aryl group represented by R$_8$ include a phenyl group, a tolyl group, a naphthyl group, a fluorene group, carbazole group, and a benzothiazole group. The cycloalkyl group may have a substituent.

l preferably represents an integer of 0 to 3.

General Formula (7) will be described in more detail.

Examples of the substituent represented by X$_2$ include an alkyl group, a cycloalkyl group, and an electron withdrawing group.

Examples of the alkyl group represented by X$_2$ include the same specific examples as the alkyl group represented by X$_1$. The alkyl group may have a substituent.

Examples of the cycloalkyl group represented by X$_2$ include the same specific examples as the cycloalkyl group represented by X$_1$. The cycloalkyl group may have a substituent.

The electron withdrawing group represented by X$_2$ is as described above.

Examples of the alkyl group represented by R$_9$ include the same specific examples as the alkyl group represented by X$_1$. The alkyl group may have a substituent, and may have, for example, an electron withdrawing group as a substituent.

Examples of the aryl group represented by R$_9$ include the same specific examples as the aryl group represented by R$_8$. The aryl group may have a substituent, and may have, for example, an electron withdrawing group as a substituent.

m preferably represents an integer of 0 to 3.

General Formula (8) will be described in more detail.

Examples of the substituent represented by X$_3$ include an alkyl group, a cycloalkyl group, and an electron withdrawing group.

Examples of the alkyl group represented by X$_3$ include the same specific examples as the alkyl group represented by X$_1$. The alkyl group may have a substituent.

Examples of the cycloalkyl group represented by X$_3$ include the same specific examples as the cycloalkyl group represented by X$_1$. The cycloalkyl group may have a substituent.

The electron withdrawing group represented by X$_3$ is as described above.

Examples of the alkyl group represented by R$_{10}$ include the same specific examples as the alkyl group represented by X$_1$ described above. The alkyl group may have a substituent and may have, for example, an electron withdrawing group as a substituent.

Examples of the aryl group represented by R$_{10}$ include the same specific examples as the aryl group represented by R$_8$ described above. The aryl group may have a substituent and may have, for example, an electron withdrawing group as a substituent.

n preferably represents an integer of 0 to 3.

In one embodiment of the present invention, the cross-linking agent of the present invention is preferably, for example, "a compound represented by the following General Formula (1)", or "a compound in which two to five structures represented by General Formula (1) are connected via a linking group or a single bond represented by L in General Formula (3)".

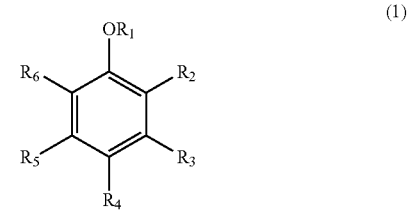

(1)

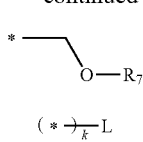

In General Formula (1), each of $R_1$ to $R_6$ independently represents a hydrogen atom, an organic group having 1 to 50 carbon atoms, or a binding site to a linking group or a single bond represented by L in General Formula (3), provided that at least one of $R_2$ to $R_6$ is a structure represented by General Formula (2), and at least one of $R_1$ to $R_6$ is the polarity converting group, or has the polarity converting group as a partial structure.

In General Formula (2), $R_7$ represents a hydrogen atom or an organic group having 1 to 30 carbon atoms, and * represents a binding site in any one of $R_2$ to $R_6$.

In General Formula (3), L represents a linking group or a single bond, * represents a binding site in any one of $R_1$ to $R_6$ and k is an integer of 2 to 5.

In one embodiment of the present invention, the polarity converting group is preferably a group represented by any one of General Formulae (4) to (8).

In the case where the crosslinking agent (C) is a compound represented by General Formula (1), each of $R_1$ to $R_6$ independently represents a hydrogen atom, or an organic group having 1 to 50 carbon atoms. Examples of the organic group having 1 to 50 carbon atoms include an alkyl group, a cycloalkyl group, or an aryl group, or, groups in which these groups are connected by an alkylene group, an arylene group, a carboxylic acid ester bond, a carbonate ester bond, an ether bond, a thioether bond, a sulfo group, a sulfone group, a urethane bond, a urea bond, or a group including a combination thereof.

Meanwhile, at least one of $R_1$ to $R_6$ is the polarity converting group, or has the polarity converting group as a partial structure. In one embodiment of the present invention, $R_1$ is preferably a polarity converting group represented by any one of General Formulae (4) to (8), or has the polarity converting group as a partial structure.

At least one of $R_2$ to $R_6$ is a structure represented by General Formula (2). Examples of the organic group having 1 to 30 carbon atoms represented by $R_7$ in General Formula (2) include the same specific examples as the organic group represented by $R_1$ to $R_6$ described above. In one embodiment of the present invention, $R_7$ is particularly preferably, for example, a hydrogen atom, an alkyl group having 1 to 6 carbon atoms, or a cycloalkyl group having 3 to 6 carbon atoms. Incidentally, $R_7$ may be the above-mentioned polarity converting group, or may be a group having the polarity converting group as a partial structure.

In another embodiment of the present invention, the crosslinking agent (C) may be a compound in which 2 to 5 of a structure represented by General Formula (1) are connected via a linking group or a single bond represented by L in General Formula (3). In this case, at least one of $R_1$ to $R_6$ in General Formula (1) represents a binding site to a linking group or a single bond represented by General Formula (3).

Examples of the linking group represented by L in General Formula (3) include an alkylene group, an arylene group, a carboxylic acid ester bond, a carbonate ester bond, an ether bond, a thioether bond, a sulfo group, a sulfone group, a urethane bond, a urea bond, or a group formed by combining two or more of these groups, preferably, an alkylene group, an arylene group, and a carboxylic ester bond.

k preferably represents 2 or 3.

In one embodiment of the present invention, the crosslinking agent of the present invention is, for example, a compound represented by General Formula (1), preferably a compound having the structure represented by General Formula (4) as a polarity converting group, or a compound in which two or three such compounds are connected via a linking group or a single bond represented by L in the following General Formula (3a).

In General Formula (3a), L has the same meaning as L in General Formula (3), and $k_1$ represents 2 or 3.

Specific examples of the crosslinking agent of the present invention are set forth below, but the present invention is not limited thereto.

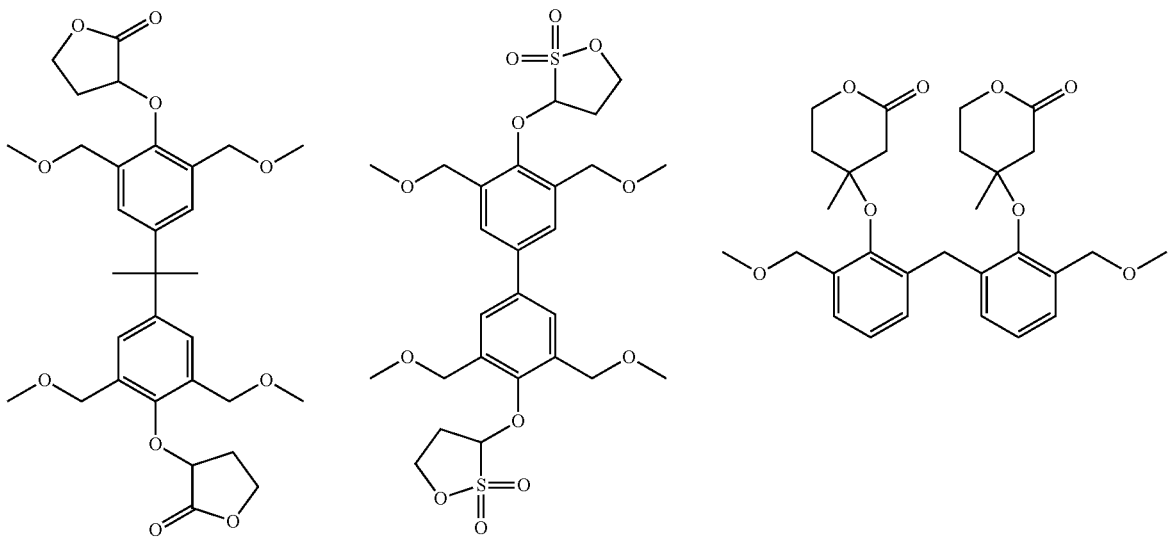

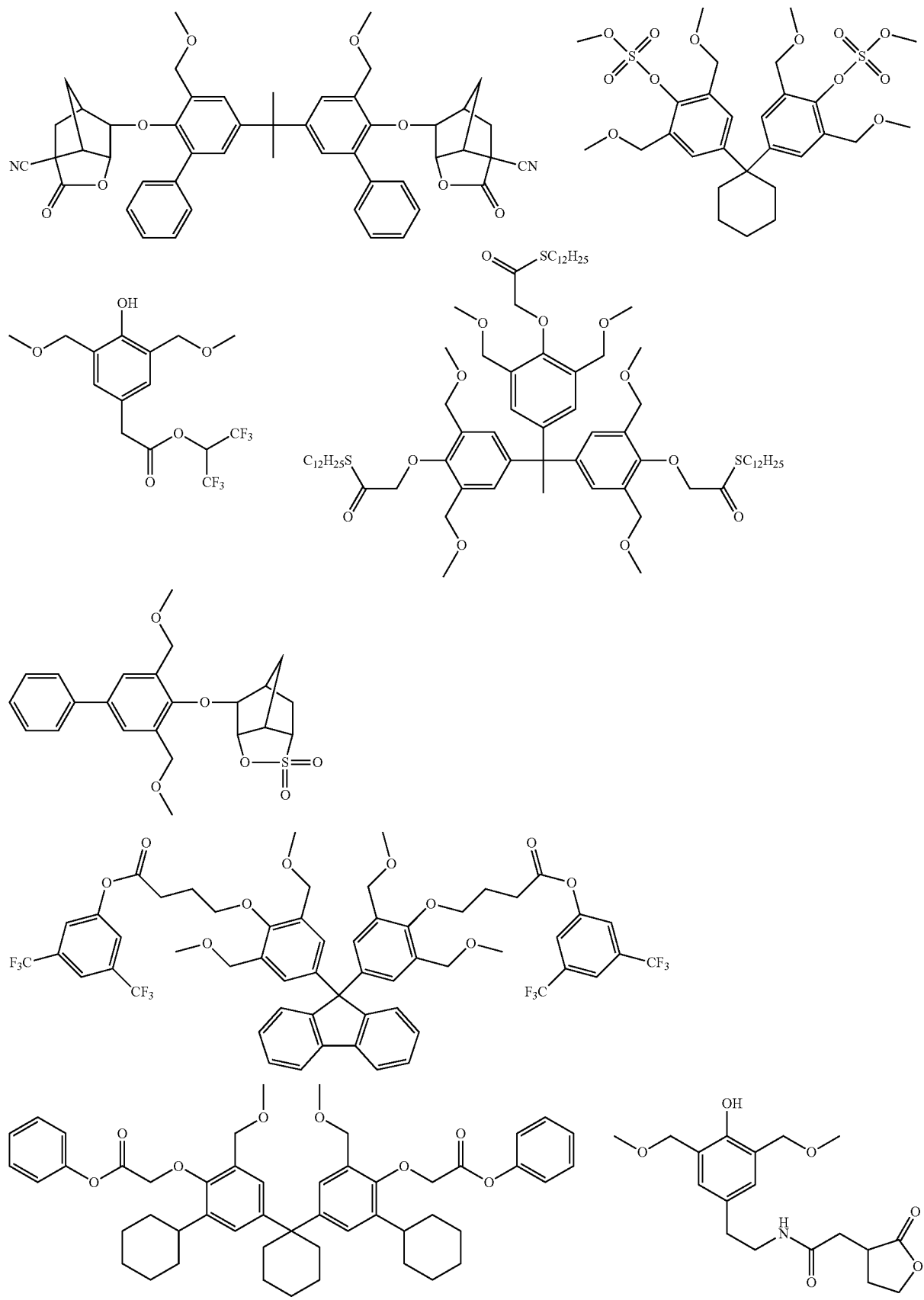

-continued
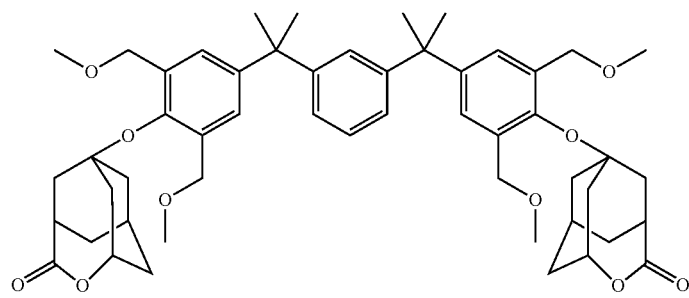
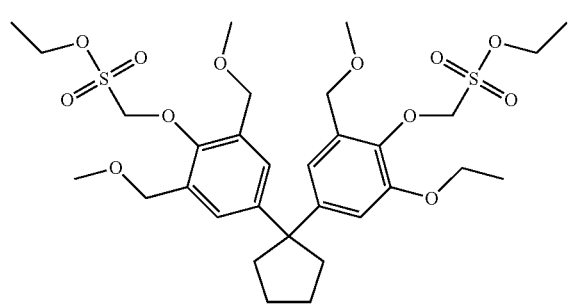
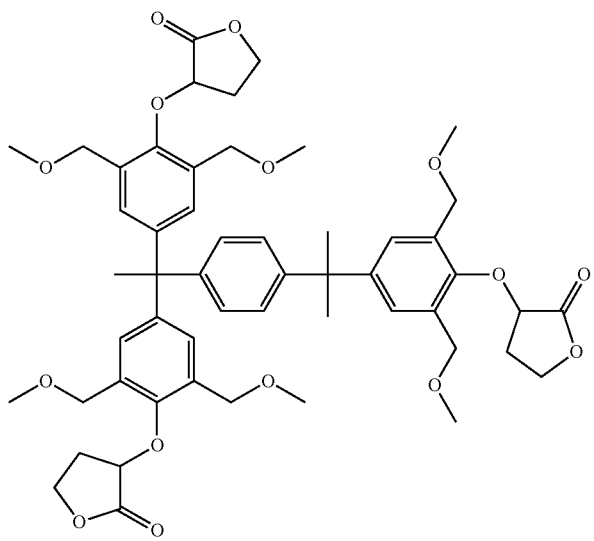
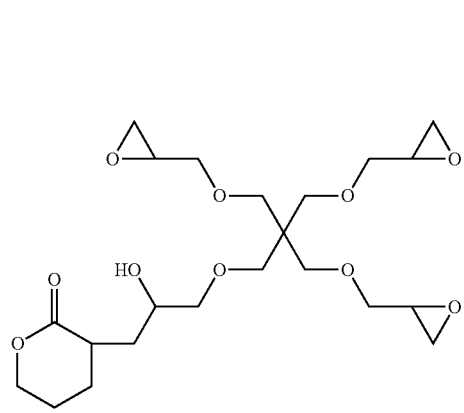
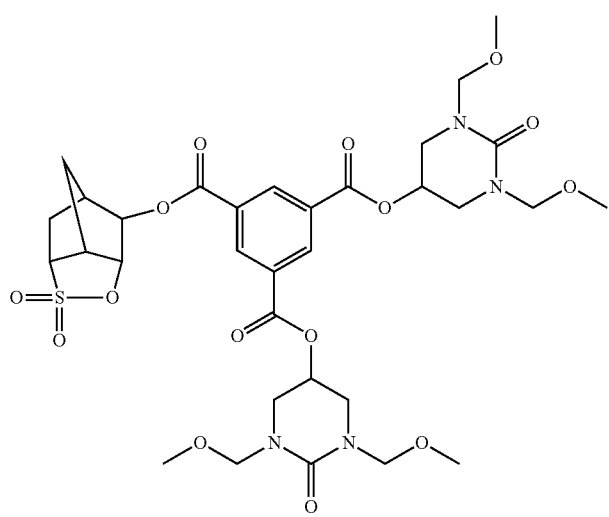
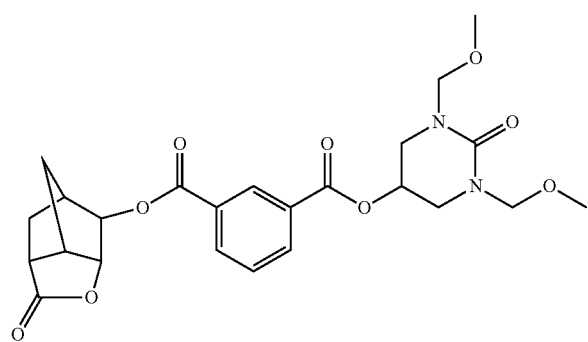

-continued

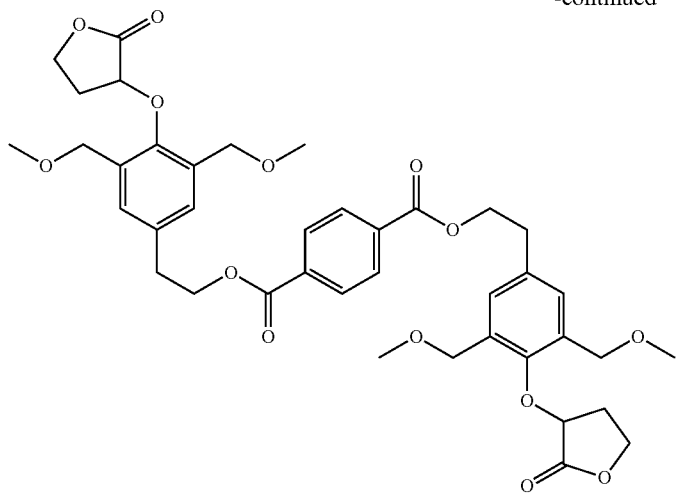

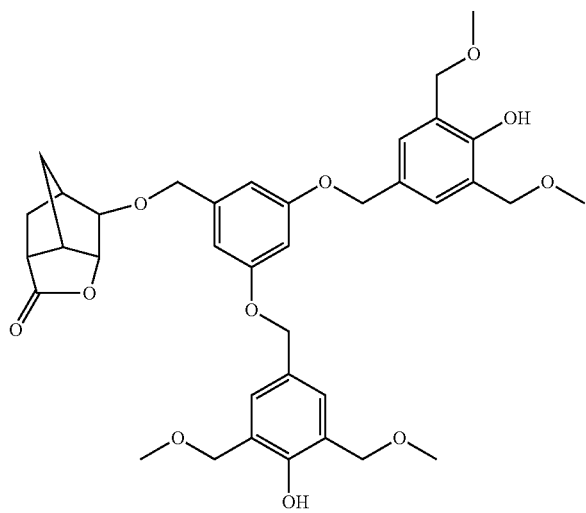

The synthesis method of the crosslinking agent (C) of the present invention may be appropriately selected depending on the desired compound, and is not limited to specific synthetic methods. An example of the method for synthesizing the crosslinking agent (C) is a method of obtaining a desired compound through a substitution reaction using a compound having a crosslinking group and a nucleophilic group (for example, a hydroxyl group) and a compound having a polarity converting group and a leaving group (for example, a halogen atom such as bromine) as raw materials.

The content of the crosslinking agent (C) in the present invention is preferably 3 to 65 mass %, more preferably 5 to 50 mass %, and still more preferably 20 to 40 mass %, based on the solid content of the actinic ray-sensitive or radiation-sensitive resin composition of the present invention. The crosslinking agent (C) may be used alone or in combination of two or more thereof.

<Alkali-Soluble Resin>

The actinic ray-sensitive or radiation-sensitive resin composition of the present invention contains an alkali-soluble resin (hereinafter referred to also as "resin (A)").

The resin (A) is not particularly limited as long as it is alkali-soluble, but the resin (A) is preferably a resin containing a phenolic hydroxyl group.

The phenolic hydroxyl group as used in the present invention is a group formed by substituting a hydrogen atom of an aromatic ring group by a hydroxyl group. The aromatic ring of this aromatic ring group is a monocyclic or polycyclic aromatic ring and includes, for example, a benzene ring and a naphthalene ring.

In the case where the composition of the present invention, in one embodiment, contains a later-described "acid generator (B)", a crossling reaction takes place in the exposed area between the alkali-soluble resin (A) containing a phenolic hydroxyl group and the crosslinking agent (C) of the present invention, by the action of an acid generated from the acid generator (B) upon irradiation with actinic rays or radiation, whereby a negative pattern is formed.

In the case where the resin (A) of the present invention contains a phenolic hydroxyl group, the resin (A) is preferably a repeating unit represented by the following General Formula (II).

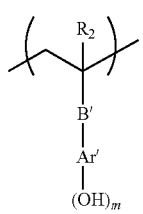

(II)

In the formula,

R₂ represents a hydrogen atom, a methyl group which may have a substituent, or a halogen atom;

B' represents a single bond or a divalent organic group;

Ar' represents an aromatic ring group; and m represents an integer of 1 or greater.

Examples of the methyl group which may have a substituent for R₂ include a trifluoromethyl group and a hydroxymethyl group.

R₂ is preferably a hydrogen atom or a methyl group, and a hydrogen atom is preferred from the viewpoint of developability.

The divalent linking group of B' is preferably a carbonyl group, an alkylene group (preferably having 1 to 10 carbon atoms, and more preferably 1 to 5 carbon atoms), a sulfonyl group (—S(=O)₂—), —O—, —NH—, or a divalent linking group formed by combining these groups.

B' preferably represents a single bond, a carbonyloxy group (—C(=O)—O—), or —C(=O)—NH—; and more preferably represents a single bond or a carbonyloxy group (—C(=O)—O—), and it is particularly preferable for B' to represent a single bond, from the viewpoint of enhancing dry etching resistance.

The aromatic ring of Ar' is a monocyclic or polycyclic aromatic ring, and examples thereof include aromatic hydrocarbon rings having 6 to 18 carbon atoms which have a substituent, such as a benzene ring, a naphthalene ring, an anthracene ring, a fluorene ring, and a phenanthrene ring; and aromatic heterocyclic rings containing heterocyclic rings such as, for example, a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring. Among them, a benzene ring and a naphthalene ring are preferred from the viewpoint of resolution, and a benzene ring is most preferred from the viewpoint of sensitivity.

m is preferably an integer of 1 to 5, and most preferably 1. When m is 1 and Ar' is a benzene ring, the position of substitution of —OH may be a para-position, a meta-position, or an ortho-position with respect to the bonding position of the benzene ring to B' (when B' is a single bond, the polymer main chain). However, from the viewpoint of crosslinking reactivity, a para-position and a meta-position are preferred, and a para-position is more preferred.

The aromatic ring of Ar' may have a substituent other than the group represented by —OH, and examples of the substituent may include an alkyl group, a cycloalkyl group, a halogen atom, a hydroxyl group, an alkoxy group, a carboxyl group, an alkoxycarbonyl group, an alkylcarbonyl group, an alkylcarbonyloxy group, an alkylsulfonyloxy group, and an arylcarbonyl group.

The repeating unit having a phenolic hydroxyl group is more preferably a repeating unit represented by the following General Formula (12), from the viewpoints of crosslinking reactivity, developability, and dry etching resistance.

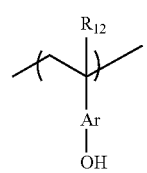

(12)

In General Formula (12),

R₁₂ represents a hydrogen atom or a methyl group.

Ar represents an aromatic ring.

R₁₂ represents a hydrogen atom or a methyl group, and is preferably a hydrogen atom in view of the developability.

Ar in General Formula (12) is the same as Ar' in General Formula (II) and its preferred range is also the same as that in General Formula (II). As for the repeating unit represented by General Formula (12), a repeating unit derived from hydroxystyrene (that is, a repeating unit of General Formula (12) in which R₁₂ is a hydrogen atom and Ar is a benzene ring) is preferred from the viewpoint of the sensitivity.

The resin (A) may be constituted by only the above described repeating unit having a phenolic hydroxyl group. The resin (A) may have a repeating unit as described below, in addition to the above described repeating unit having a phenolic hydroxyl group. In this case, the content of the repeating unit having a phenolic hydroxyl group is preferably 10 mol % to 98 mol %, more preferably 30 mol % to 97 mol %, and still more preferably 40 mol % to 95 mol %, based on the total content of the repeating units of the resin (A). Accordingly, particularly, in the case where the resist film is a thin film (for example, in the case where the thickness of the resist film is from 10 nm to 150 nm), it is possible to more reliably reduce the dissolution rate of an exposed area of the resist film of the present invention, which is formed using the composition of the present invention, in an alkali developer (that is, it is possible to more reliably control the dissolution rate of the resist film employing the composition of the present invention to an optimum level). As a result, the sensitivity may be more reliably improved.

Examples of the repeating unit having a phenolic hydroxyl group will be described below, but are not limited thereto.

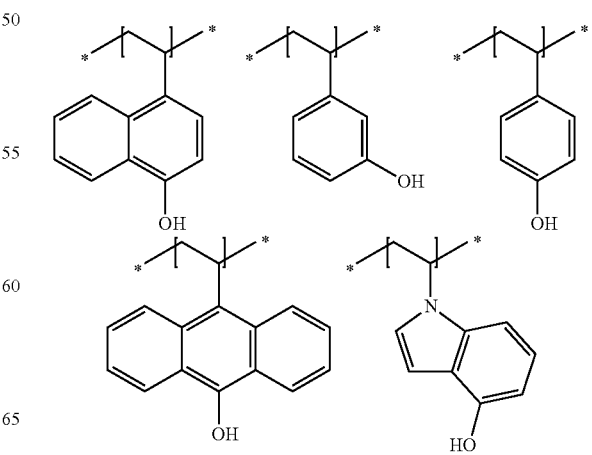

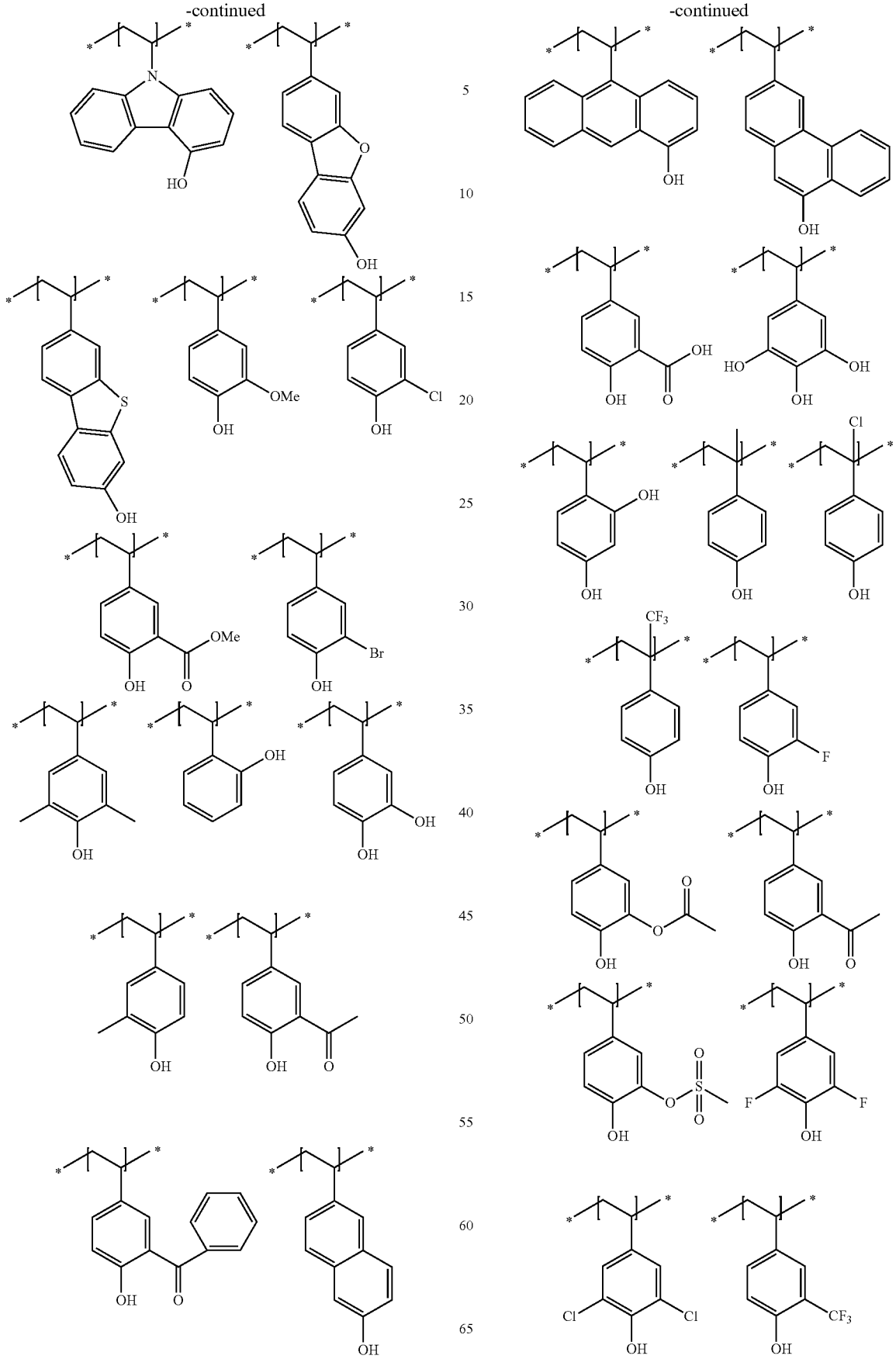

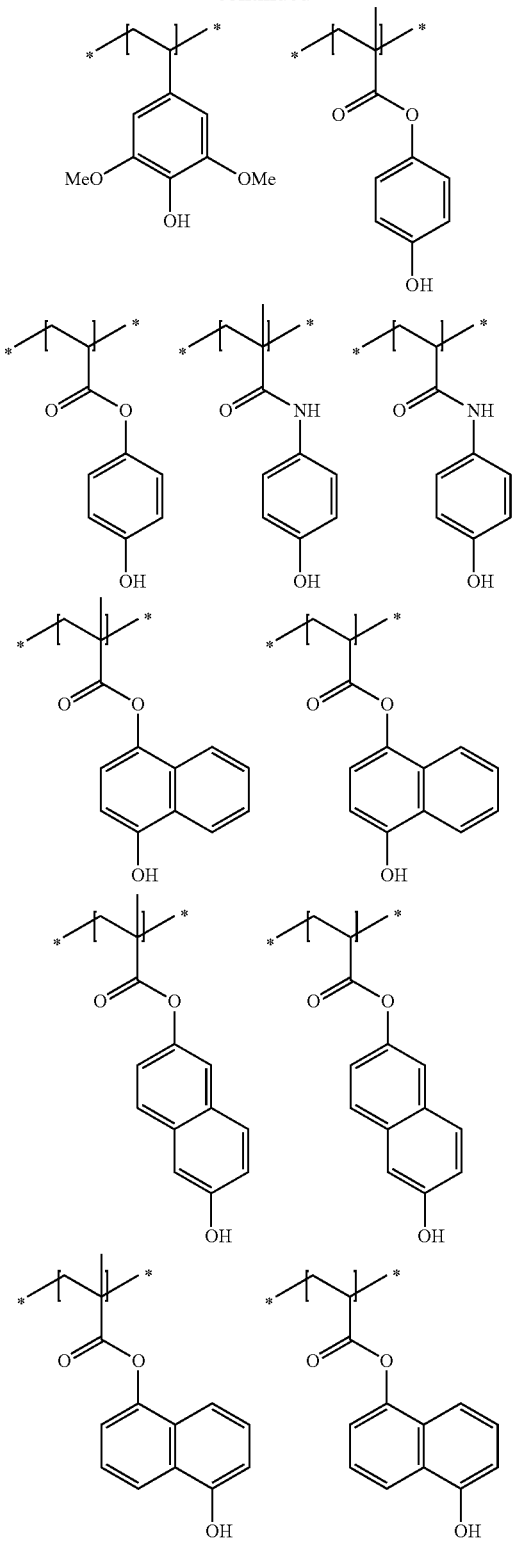

The resin (A) preferably has "a structure in which a hydrogen atom of the phenolic hydroxyl group is substituted with a group having a non-acid-decomposable polycyclic alicyclic hydrocarbon structure" from the viewpoints of achieving a high glass transition temperature (Tg) and favorable dry etching resistance.

Due to the fact that the resin (A) has a specific structure as described above, the glass transition temperature (Tg) of the resin (A) becomes high, so that a very hard resist film can be formed and the acid diffusion or dry etching resistance can be controlled. Accordingly, an acid is highly constrained from diffusion in the area exposed to actinic rays or radiation such as an electron beam and extreme ultraviolet rays, and this produces an excellent effect in terms of resolution, pattern profile, and LER in a fine pattern. Also, the point that the resin (A) has a non-acid-decomposable polycyclic alicyclic hydrocarbon structure further contributes to an improvement in dry etching resistance. Furthermore, although details are unknown, it is presumed that the polycyclic alicyclic hydrocarbon structure has a high hydrogen radical-donating property and become to serve as a hydrogen source when decomposing a photoacid generator, as a result, the decomposition efficiency of the photoacid generator and in turn, the acid generation efficiency are further enhanced. This is considered to contribute to excellent sensitivity.

In the aforementioned specific structure which may be taken by the resin (A) in the context of the present invention, an aromatic ring such as a benzene ring and a group having a non-acid-decomposable polycyclic alicyclic hydrocarbon structure are connected through an oxygen atom derived from a phenolic hydroxyl group. As described above, that structure not only contributes to high dry etching resistance but also enables raising the glass transition temperature (Tg) of the resin (A). As a consequence, combinatorial effects thereof are believed to provide higher resolution.

In the present invention, the "non-acid-decomposable" means a property of not causing a decomposition reaction by an acid generated from a photoacid generator.

More specifically, the group having a non-acid-decomposable polycyclic alicyclic hydrocarbon structure is preferably a group stable to an acid and an alkali. The term "group stable to an acid and an alkali" means a group not exhibiting acid decomposability and alkali decomposability. The term "acid decomposability" as used herein means a property of causing a decomposition reaction by the action of an acid generated from a photoacid generator.

Also, the term "alkali decomposability" means a property of causing a decomposition reaction by the action of an alkali developer, and the group exhibiting alkali decomposability includes the conventionally known group capable of decomposing by the action of an alkali developer to increase the dissolution rate in an alkali developer (for example, a group having a lactone structure), which is contained in the resin suitably used for the chemically amplified positive resist composition.

In the present invention, the group having a polycyclic alicyclic hydrocarbon structure is not particularly limited as long as it is a monovalent group having a polycyclic alicyclic hydrocarbon structure, but the total number of carbon atoms thereof is preferably 5 to 40, and more preferably 7 to 30. The polycyclic alicyclic hydrocarbon structure may have an unsaturated bond in the ring.

The polycyclic alicyclic hydrocarbon structure in the group having a polycyclic alicyclic hydrocarbon structure means a structure having plural monocyclic alicyclic hydrocarbon groups, or a polycyclic alicyclic hydrocarbon structure, and may be a crosslinked structure. The monocyclic alicyclic hydrocarbon group is preferably a cycloalkyl group having 3 to 8 carbon atoms, and examples thereof include a cyclopropyl group, a cyclopentyl group, a cyclohexyl group, a cyclobutyl group, and a cyclooctyl group. The structure having plural monocyclic alicyclic hydrocarbon groups has plural such groups. The structure having plural monocyclic alicyclic hydrocarbon groups preferably has two to four monocyclic alicyclic hydrocarbon groups, and particularly preferably two monocyclic alicyclic hydrocarbon groups.

The polycyclic alicyclic hydrocarbon structure may be a bicyclo-, tricyclo-, or tetracyclo-structure having 5 or more carbon atoms and is preferably a polycyclic cyclo-structure having 6 to 30 carbon atoms, and examples thereof may include an adamantane structure, a decalin structure, a norbornane structure, a norbornene structure, a cedrol structure, an isobornane structure, a bornane structure, a dicyclopentane structure, an α-pinene structure, a tricyclodecane structure, a tetracyclododecane structure, and an androstane structure. Incidentally, a part of carbon atoms in the monocyclic or polycyclic cycloalkyl group may be substituted by a heteroatom such as oxygen atom.

The polycyclic alicyclic hydrocarbon structure is preferably an adamantane structure, a decalin structure, a norbornane structure, a norbornene structure, a cedrol structure, a structure having a plurality of cyclohexyl groups, a structure having a plurality of cycloheptyl groups, a structure having a plurality of cyclooctyl groups, a structure having a plurality of cyclodecanyl groups, a structure having a plurality of cyclododecanyl groups, or a tricyclodecane structure, and most preferably an adamantane structure in view of dry etching resistance (that is, it is most preferred that the group having a non-acid-decomposable polycyclic alicyclic hydrocarbon structure is a group having a non-acid-decomposable adamantane structure).

Chemical formulae of these polycyclic alicyclic hydrocarbon structures (for the structure having plural monocyclic alicyclic hydrocarbon groups, a monocyclic alicyclic hydrocarbon structure corresponding to the monocyclic alicyclic hydrocarbon group (specifically structures of the following Formulae (47) to (50))) are illustrated below.

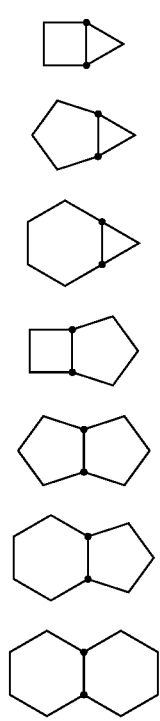

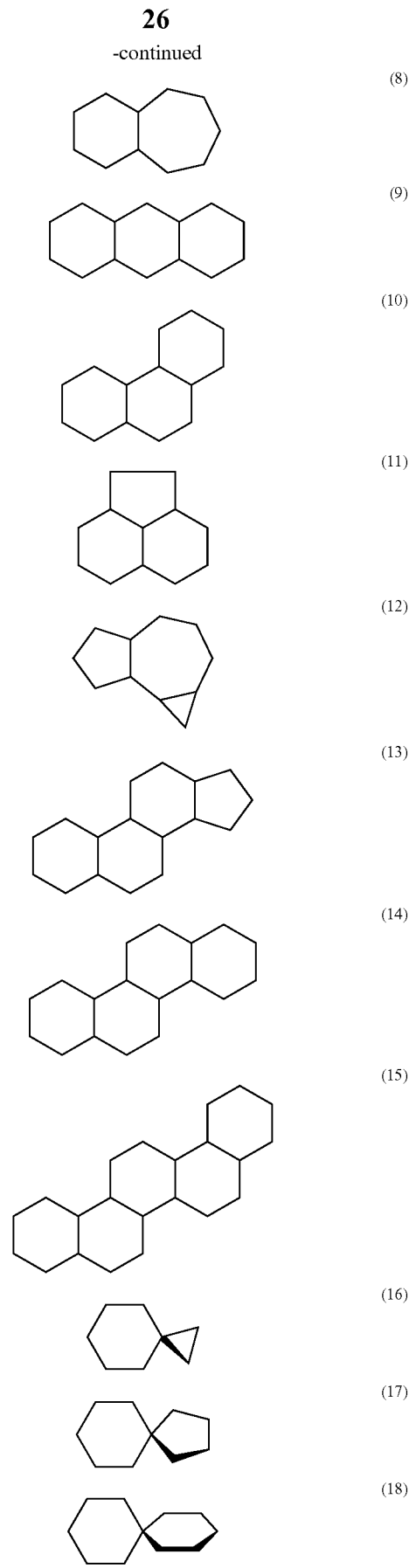

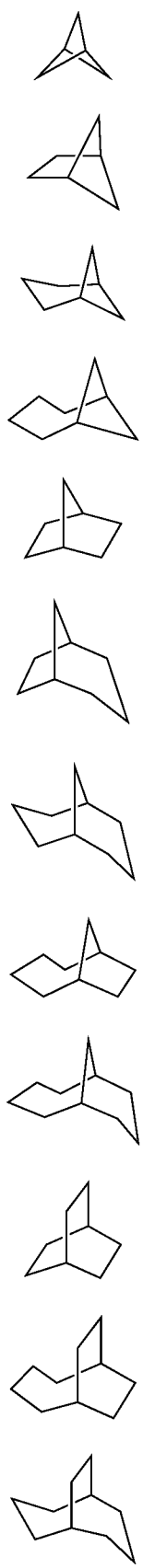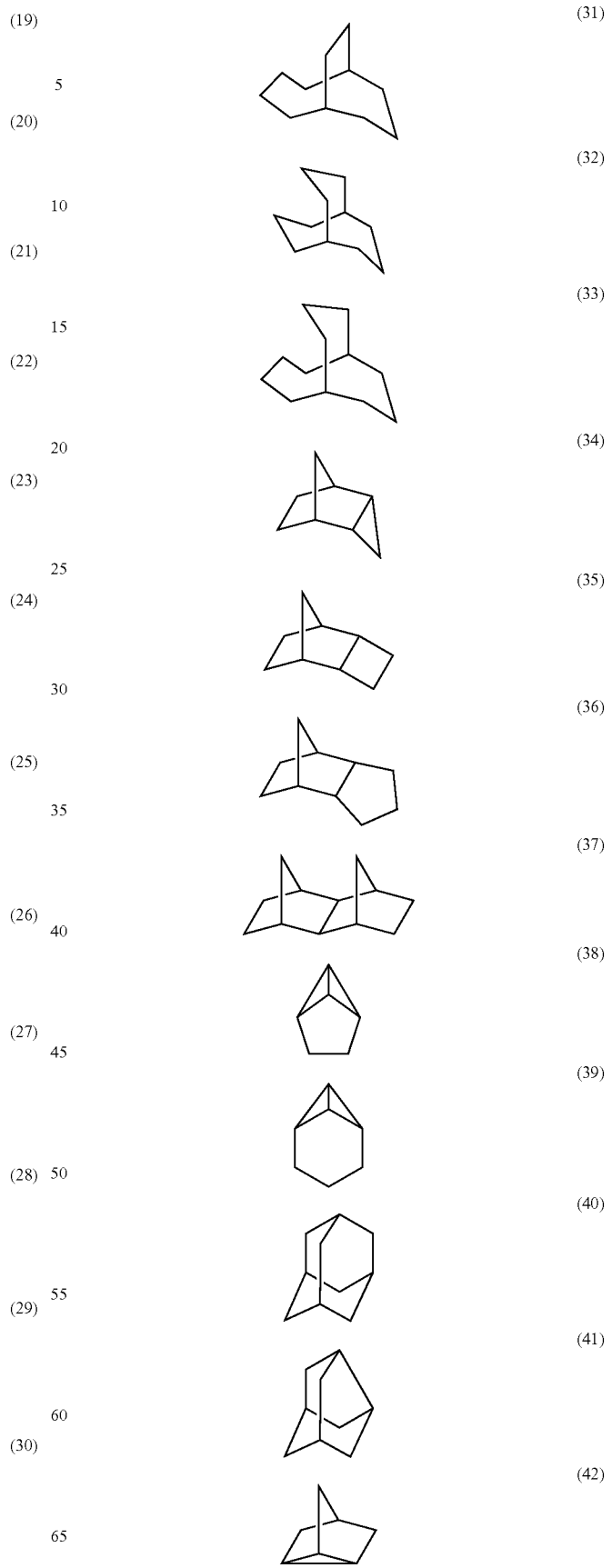

(43) 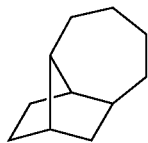

(44) 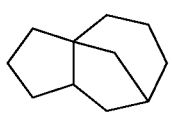

(45) 

(46) 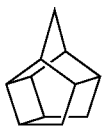

(47) 

(48) 

(49) 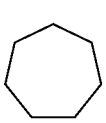

(50)

(51) 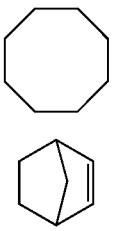

The polycyclic alicyclic hydrocarbon structure may further have a substituent, and examples of the substituent may include an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, a carbonyl group, a thiocarbonyl group, an alkoxycarbonyl group (preferably having 2 to 7 carbon atoms), and a group formed by combining these groups (preferably having a total of 1 to 30 carbon atoms, and more preferably a total of 1 to 15 carbon atoms).

The polycyclic alicyclic hydrocarbon structure is preferably a structure represented by any one of Formulae (7), (23), (40), (41), and (51), or a structure having two monovalent groups each formed by substituting a bond for one arbitrary hydrogen atom in the structure of Formula (48), more preferably a structure represented by any one of Formulae (23), (40), and (51), or a structure having two monovalent groups each formed by substituting a bond for one arbitrary hydrogen atom in the structure of Formula (48), and most preferably a structure represented by Formula (40).

The group having a polycyclic alicyclic hydrocarbon structure is preferably a monovalent group formed by substituting a bond for one arbitrary hydrogen atom in the above-described hydrocarbon structure.

The above-described "structure where a hydrogen atom of a phenolic hydroxyl group is substituted by a group having a non-acid-decomposable polycyclic alicyclic hydrocarbon structure" is preferably contained as a repeating unit in the resin (A). The above-described structure is more preferably contained as a repeating unit represented by the following General Formula (3A) in resin (A).

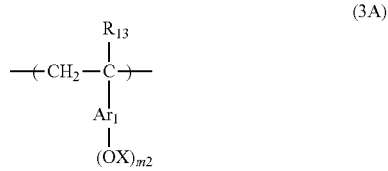

(3A)

In General Formula (3A), $R_{13}$ represents a hydrogen atom or a methyl group.

X represents a group having a non-acid-decomposable polycyclic alicyclic hydrocarbon structure.

$Ar_1$ represents an aromatic ring.

m2 is an integer of 1 or more.

In General Formula (3A), $R_{13}$ represents a hydrogen atom or a methyl group and is particularly preferably a hydrogen atom.

Examples of the aromatic ring represented by $Ar_1$ in General Formula (3A) may include an aromatic hydrocarbon ring having 6 to 18 carbon atoms which may have a substituent, such as benzene ring, naphthalene ring, anthracene ring, fluorene ring, and phenanthrene ring, and an aromatic heterocyclic ring containing a heterocyclic ring such as thiophene ring, furan ring, pyrrole ring, benzothiophene ring, benzofuran ring, benzopyrrole ring, triazine ring, imidazole ring, benzimidazole ring, triazole ring, thiadiazole ring, and thiazole ring. Among these, a benzene ring and a naphthalene ring are preferred in view of resolution, and a benzene ring is most preferred.

The aromatic ring of $Ar_1$ may have a substituent other than the group represented by —OX, and examples of the substituent may include an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, and an alkoxycarbonyl group (preferably having 2 to 7 carbon atoms). Among these, an alkyl group, an alkoxy group, and an alkoxycarbonyl group are preferred, and an alkoxy group is more preferred.

X represents a group having a non-acid-decomposable polycyclic alicyclic hydrocarbon structure. Specific examples and preferred ranges of the group having a non-acid-decomposable polycyclic alicyclic hydrocarbon structure represented by X are the same as those described above. X is more preferably a group represented by —Y—$X_2$ in later-described General Formula (4).

m2 is preferably an integer of 1 to 5, and most preferably 1. When m2 is 1 and $Ar_1$ is a benzene ring, the position of substitution of —OX may be a para-position, a meta-position, or an ortho-position with respect to the bonding position of the benzene ring to the polymer main chain. A para-position and a meta-position are preferred, and a para-position is more preferred.

In the present invention, the repeating unit represented by General Formula (3A) is preferably a repeating unit represented by the following General Formula (4A).

When the resin (A) having a repeating unit represented by General Formula (4A) is used, Tg of the resin (A) becomes high and a very hard resist film is formed, so that the acid diffusion and dry etching resistance can be more reliably controlled.

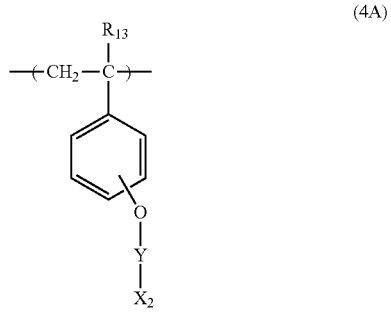

(4A)

In General Formula (4A), $R_{13}$ represents a hydrogen atom or a methyl group.

Y represents a single bond or a divalent linking group.

$X_2$ represents a non-acid-decomposable polycyclic alicyclic hydrocarbon group.

Preferred embodiments of the repeating unit represented by General Formula (4A) for use in the present invention are described below.

In General Formula (4A), $R_{13}$ represents a hydrogen atom or a methyl group and is particularly preferably a hydrogen atom.

In General Formula (4A), Y is preferably a divalent linking group. The divalent linking group of Y is preferably a carbonyl group, a thiocarbonyl group, an alkylene group (preferably having 1 to 10 carbon atoms, more preferably 1 to 5 carbon atoms), a sulfonyl group, —COCH₂—, —NH—, or a divalent linking group formed by combining these groups (preferably having a total of 1 to 20 carbon atoms, and more preferably a total of 1 to 10 carbon atoms), more preferably a carbonyl group, —COCH₂—, a sulfonyl group, —CONH—, or —CSNH—, still more preferably a carbonyl group or —COCH₂—, and particularly preferably a carbonyl group.

$X_2$ represents a polycyclic alicyclic hydrocarbon group and is non-acid-decomposable. The total number of carbon atoms in the polycyclic alicyclic hydrocarbon group is preferably 5 to 40, and more preferably 7 to 30. The polycyclic alicyclic hydrocarbon group may have an unsaturated bond in the ring thereof.

This polycyclic alicyclic hydrocarbon group is a group having plural monocyclic alicyclic hydrocarbon groups, or a polycyclic alicyclic hydrocarbon group, and may be a crosslinked group. The monocyclic alicyclic hydrocarbon group is preferably a cycloalkyl group having 3 to 8 carbon atoms, and examples thereof may include a cyclopropyl group, a cyclopentyl group, a cyclohexyl group, a cyclobutyl group, and a cyclooctyl group. The polycyclic alicyclic hydrocarbon group has plural such groups. The group having plural monocyclic alicyclic hydrocarbon groups preferably has two to four monocyclic alicyclic hydrocarbon groups, and particularly preferably two monocyclic alicyclic hydrocarbon groups.

The polycyclic alicyclic hydrocarbon group may include a group containing, for example, a bicyclo-, tricyclo-, or tetracyclo-structure having 5 or more carbon atoms and is preferably a group containing a polycyclic cyclo-structure having 6 to 30 carbon atoms, and examples thereof include an adamantyl group, a norbornyl group, a norbornenyl group, an isobornyl group, a camphanyl group, a dicyclopentyl group, an α-pinel group, a tricyclodecanyl group, a tetracyclododecyl group, and an androstanyl group. Incidentally, a part of carbon atoms in the monocyclic or polycyclic cycloalkyl group may be substituted by a heteroatom such as oxygen atom.

The polycyclic alicyclic hydrocarbon group of $X_2$ is preferably an adamantyl group, a decalin group, a norbornyl group, a norbornenyl group, a cedrol group, a group having a plurality of cyclohexyl groups, a group having a plurality of cycloheptyl groups, a group having a plurality of cyclooctyl groups, a group having a plurality of cyclodecanyl groups, a group having a plurality of cyclododecanyl groups, or a tricyclodecanyl group, and most preferably an adamantyl group in view of dry etching resistance. Examples of the chemical formula of the polycyclic alicyclic hydrocarbon structure in the polycyclic alicyclic hydrocarbon group of $X_2$ are the same as those of the chemical formula of the polycyclic alicyclic hydrocarbon structure in the above-described group having a polycyclic alicyclic hydrocarbon structure, and the preferred range thereof is also the same. The polycyclic alicyclic hydrocarbon group of $X_2$ includes a monovalent group formed by substituting a bond for one arbitrary hydrogen atom in the above-described polycyclic alicyclic hydrocarbon structure.

The alicyclic hydrocarbon group may further have a substituent, and examples of the substituent are the same as those described above as the substituent which may be substituted on the polycyclic alicyclic hydrocarbon structure.

In General Formula (4A), the substitution position of —O—Y—$X_2$ may be a para-position, a meta-position, or an ortho-position with respect to the bonding position of the benzene ring to the polymer main chain but is preferably a para-position.

In the present invention, the repeating unit represented by General Formula (3A) is most preferably a repeating unit represented by the following General Formula (4'):

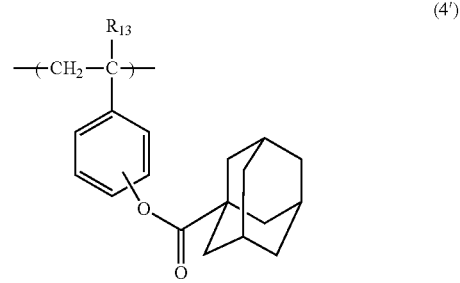

(4')

In General Formula (4'), $R_{13}$ represents a hydrogen atom or a methyl group.

In General Formula (4'), $R_{13}$ represents a hydrogen atom or a methyl group and is particularly preferably a hydrogen atom.

In General Formula (4'), the substitution position of the adamantyl ester group may be a para-position, a meta-position, or an ortho-position with respect to the bonding position of the benzene ring to the polymer main chain but is preferably a para-position.
Specific examples of the repeating unit represented by General Formula (3A) may include the followings.
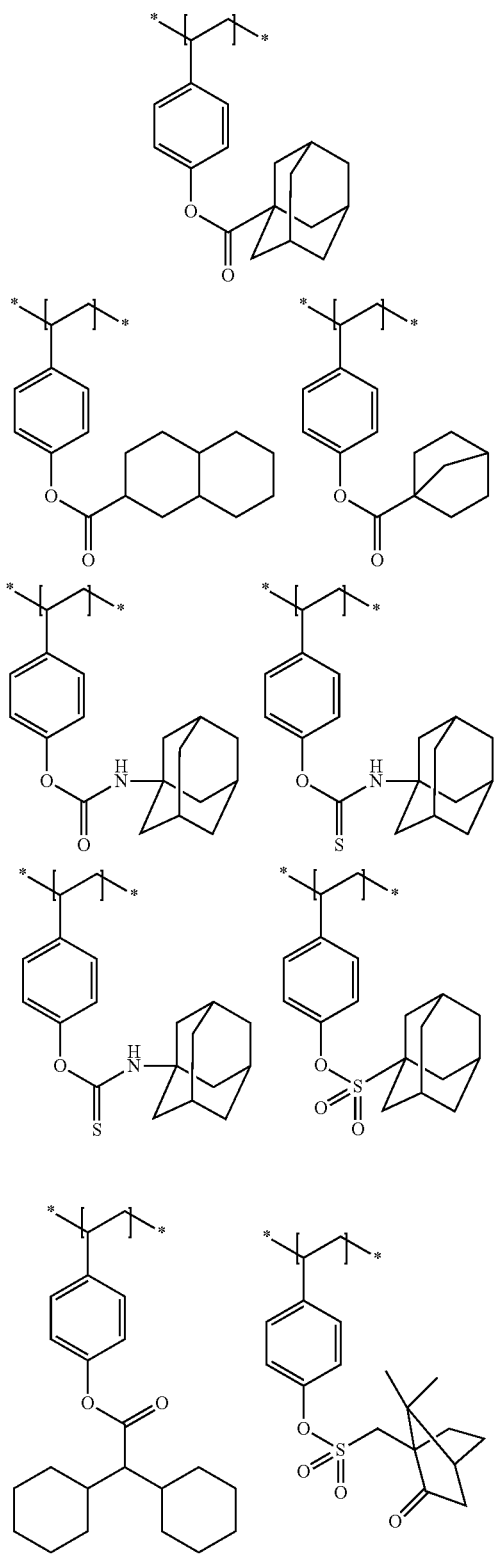
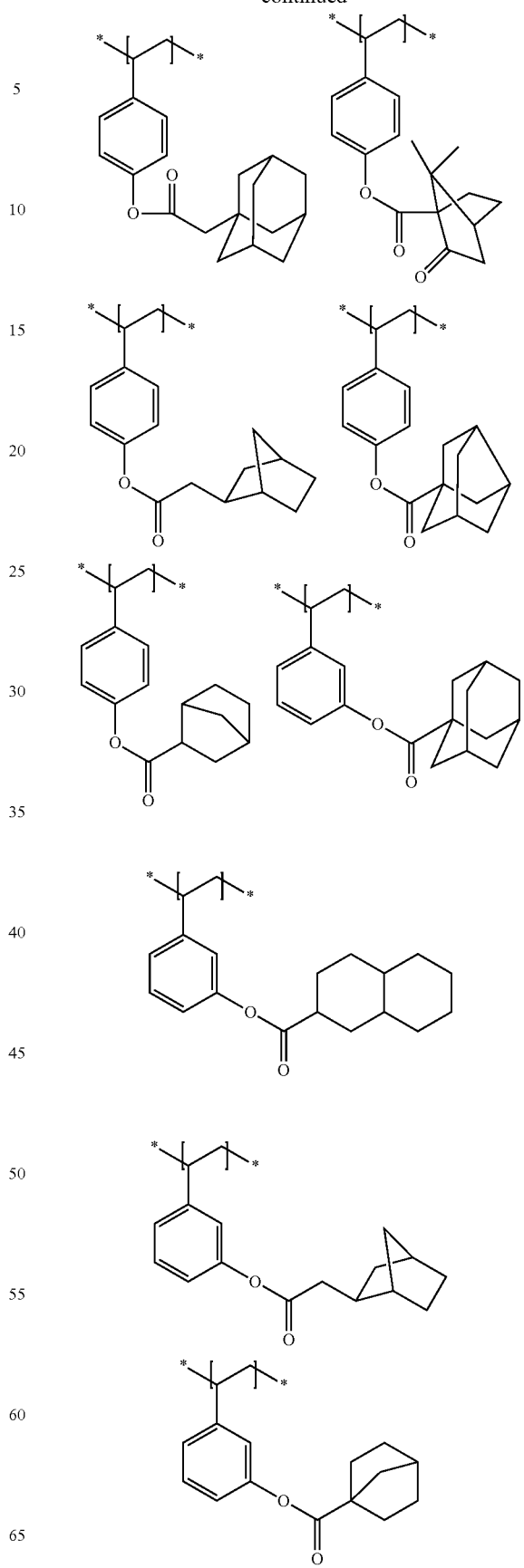

35
-continued
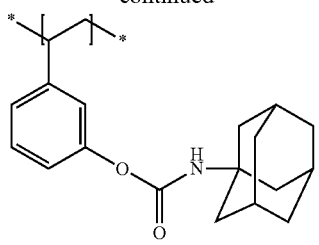
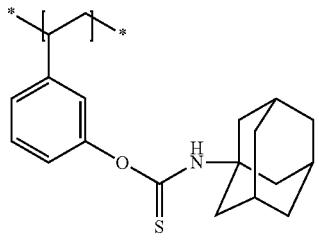
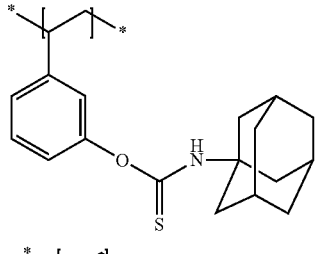
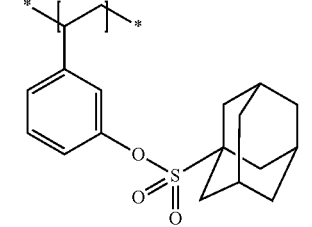
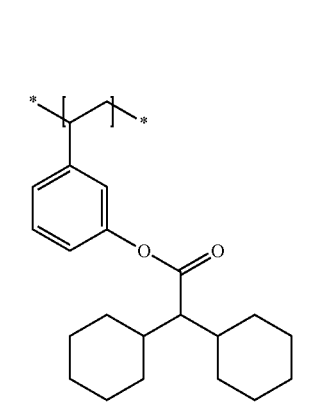
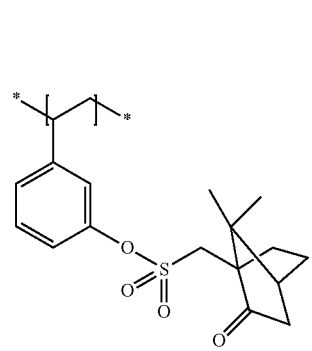
36
-continued
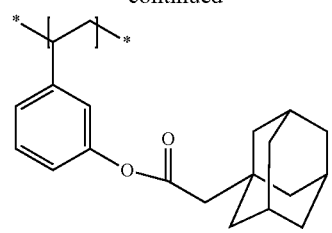
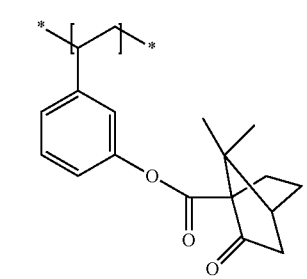
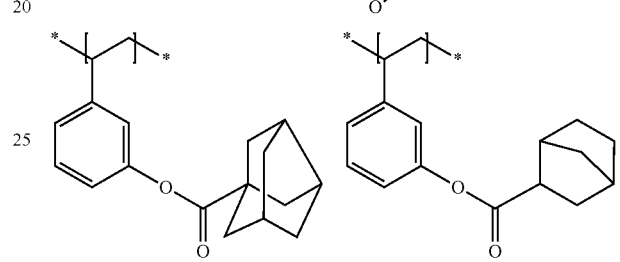
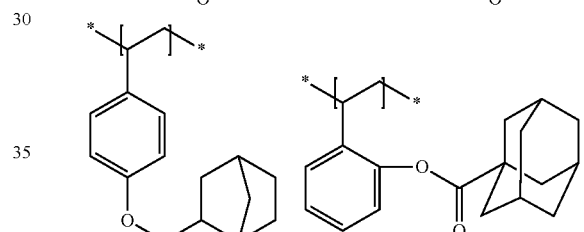
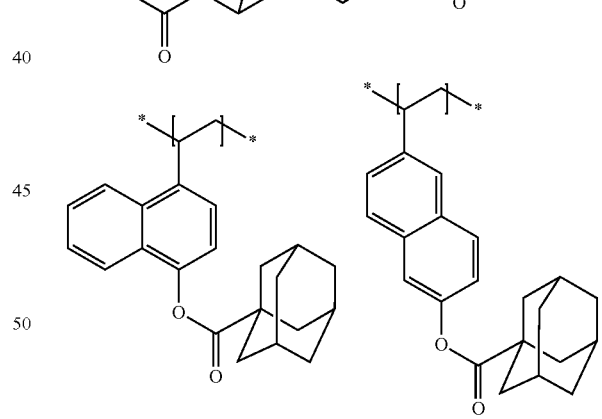
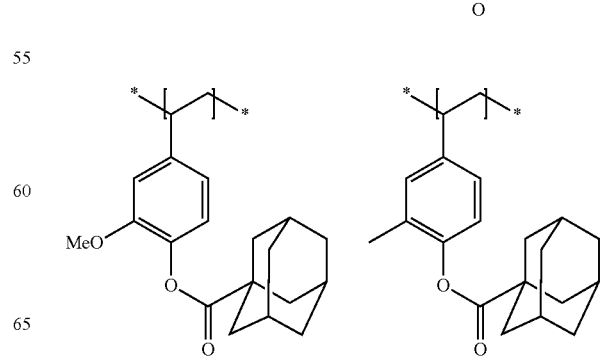

-continued

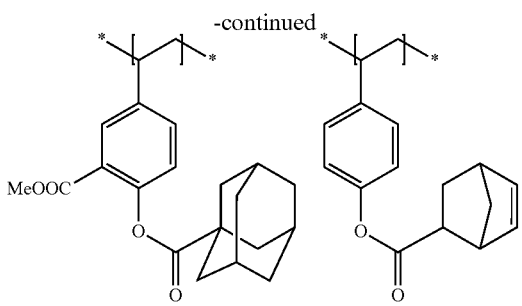

In the case where the resin (A) contains a repeating unit having the above-mentioned "structure where a hydrogen atom of the phenolic hydroxyl group is substituted by a group having a non-acid-decomposable polycyclic alicyclic hydrocarbon structure", the content of the repeating unit is preferably 1 mol % to 40 mol %, and more preferably 2 mol % to 30 mol %, based on total repeating units of the resin (A).

The resin (A) may further include a repeating unit having a structural moiety capable of decomposing upon irradiation with actinic rays or radiation to generate an acid on the side chain.

Preferably, the resin (A) used in the present invention further has the following repeating unit (hereinafter, also referred to as "other repeating unit") as a repeating unit other than the above described repeating unit.

Examples of a polymerizable monomer for forming these other repeating units may include styrene, alkyl-substituted styrene, alkoxy-substituted styrene, halogen-substituted styrene, O-alkylated styrene, O-acylated styrene, hydrogenated hydroxystyrene, a maleic anhydride, an acrylic acid derivative (for example, acrylic acid or acrylic acid ester), a methacrylic acid derivative (for example, methacrylic acid or methacrylic acid ester), N-substituted maleimide, acrylonitrile, methacrylonitrile, vinyl naphthalene, vinyl anthracene, and indene which may have a substituent.

The resin (A) may or may not contain these other repeating units. In the case where the resin (A) contains these other repeating units, the content of these repeating units in the resin (A) is generally 1 mol % to 30 mol %, preferably 1 mol % to 20 mol %, and still more preferably 2 to 10 mol %, based on the total repeating units constituting the resin (A).

The resin (A) may be synthesized by a known method such as a radical polymerization method, an anionic polymerization method, or a living radical polymerization method (for example, an iniferter method). For example, in the anionic polymerization method, vinyl monomers are dissolved in an appropriate organic solvent, and reacted usually under a cooling condition by using a metal compound (for example, butyllithium) as an initiator, whereby the polymer can be obtained.

As the resin (A), a polyphenol compound produced by a condensation reaction of an aromatic ketone or aromatic aldehyde and a compound containing 1 to 3 phenolic hydroxyl groups (see, for example, JP2008-145539A), a calixarene derivative (see, for example, JP2004-18421A), a Noria derivative (see, for example, JP2009-222920A), and a polyphenol derivative (see, for example, JP2008-94782A) can also be applied, and these may be modified by a polymer reaction to synthesize the resin.

The resin (A) is preferably synthesized by modifying a polymer synthesized by a radical polymerization or anionic polymerization method, through a polymer reaction.

The weight average molecular weight of the resin (A) is preferably 1,000 to 200,000, more preferably 2,000 to 50,000, and still more preferably 2,000 to 15,000.

The polydispersity (molecular weight distribution) (Mw/Mn) of the resin (A) is preferably 2.0 or less, and from the viewpoint of enhancing the sensitivity and resolution, the polydispersity thereof is preferably 1.0 to 1.80, more preferably 1.0 to 1.60, and most preferably 1.0 to 1.20. The use of living polymerization such as living anionic polymerization is preferred because the obtained polymer compound may have a uniform polydispersity (molecular weight distribution). The weight average molecular weight and polydispersity of the compound (D) as a polymer compound are defined as values in terms of polystyrene by GPC measurement.

The amount of the resin (A) added in the composition of the present invention is preferably 30 mass % to 95 mass %, more preferably 40 mass % to 90 mass %, and particularly preferably 50 mass % to 85 mass %, based on the total solid content of the composition.

Specific examples of the resin (A) will be shown below, but the present invention is not limited thereto.

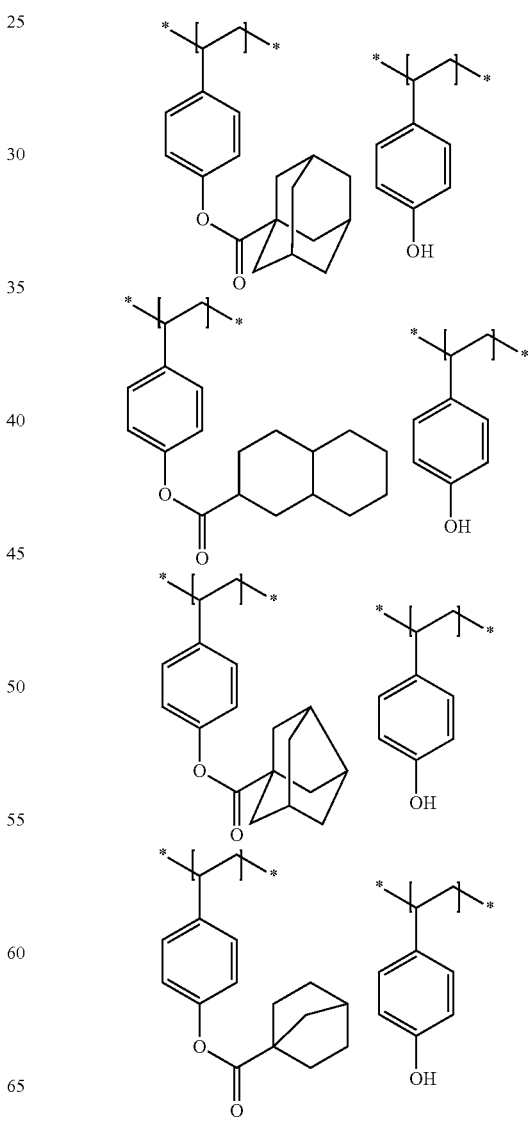

39
-continued
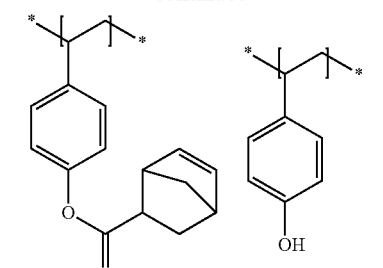
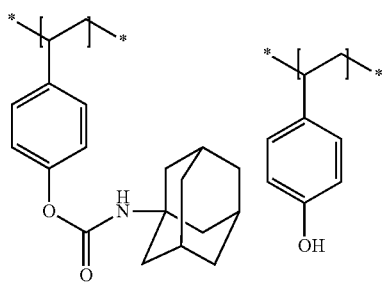
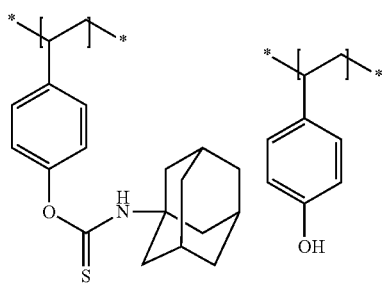
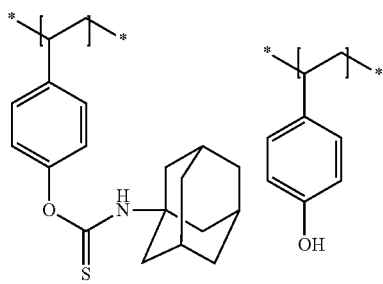
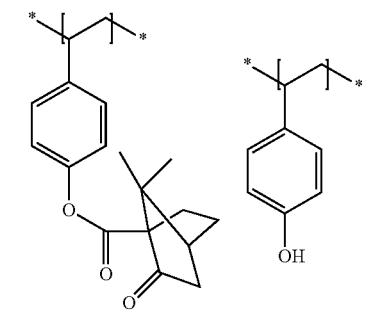
40
-continued
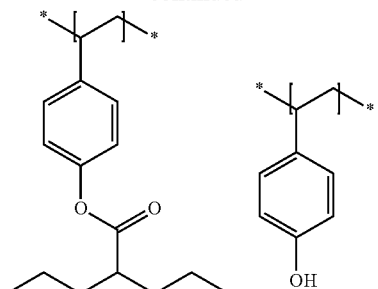
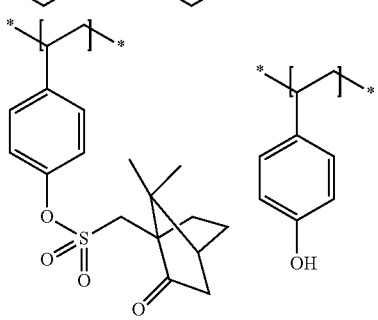
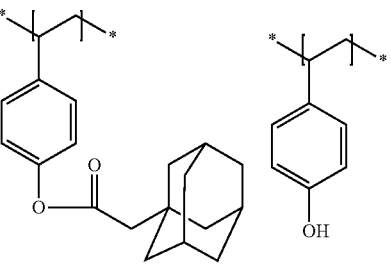
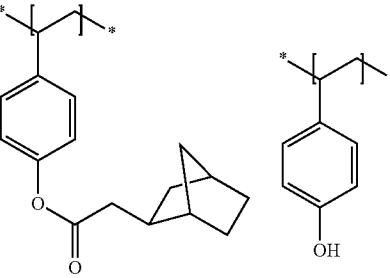
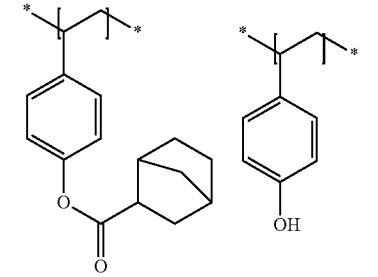

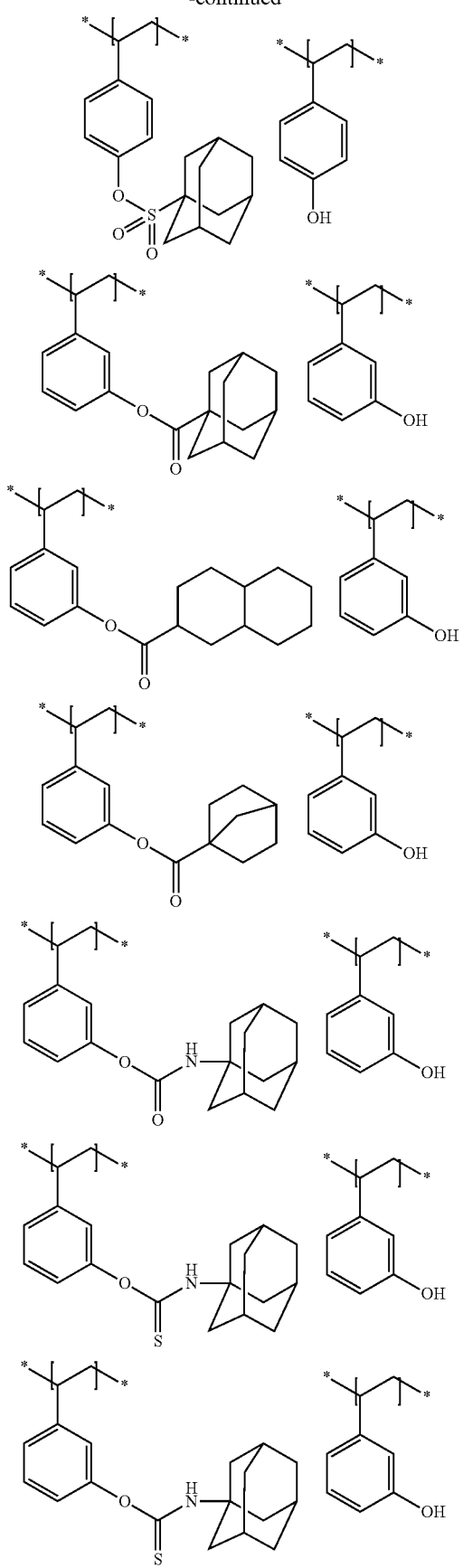
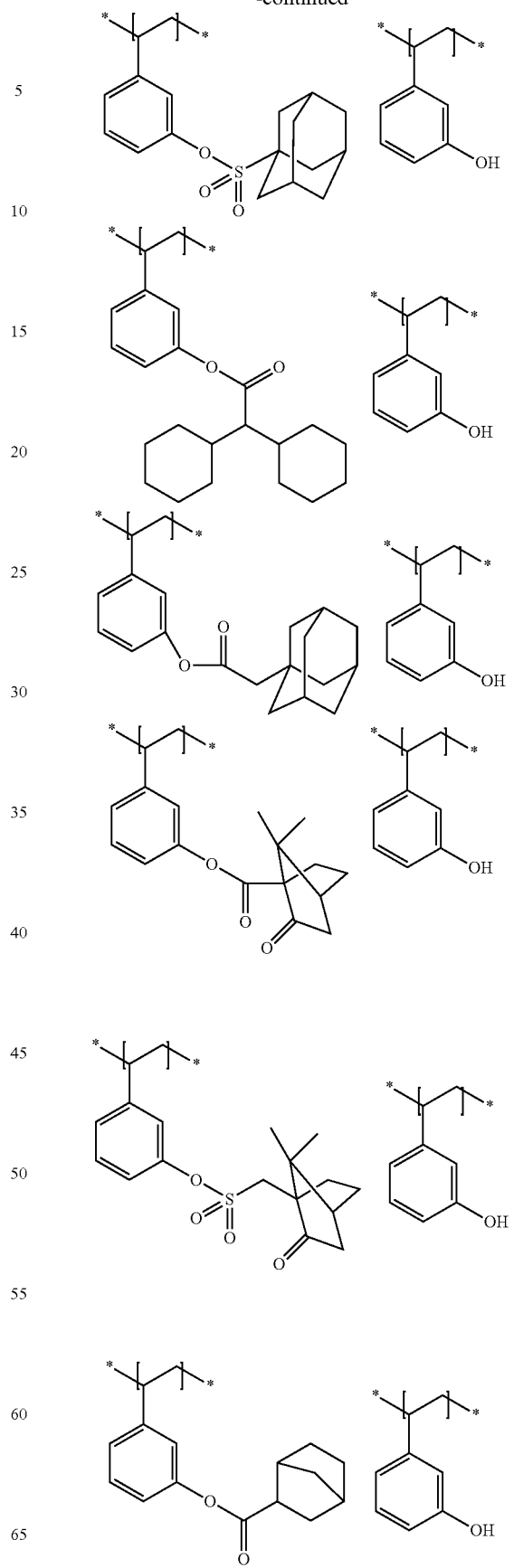

43
-continued
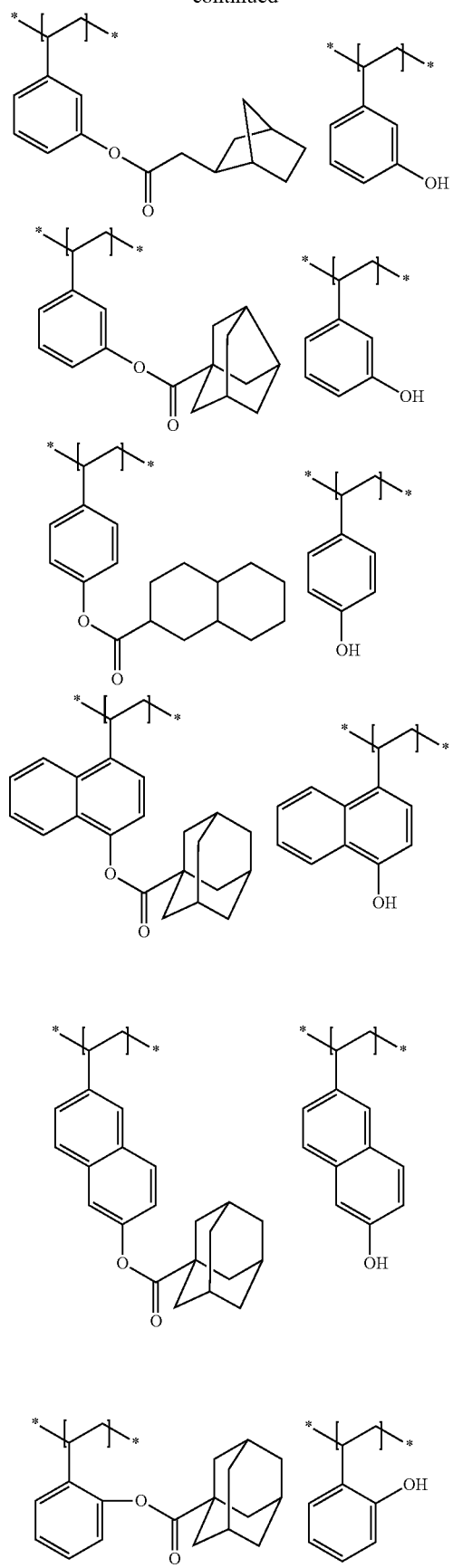
44
-continued
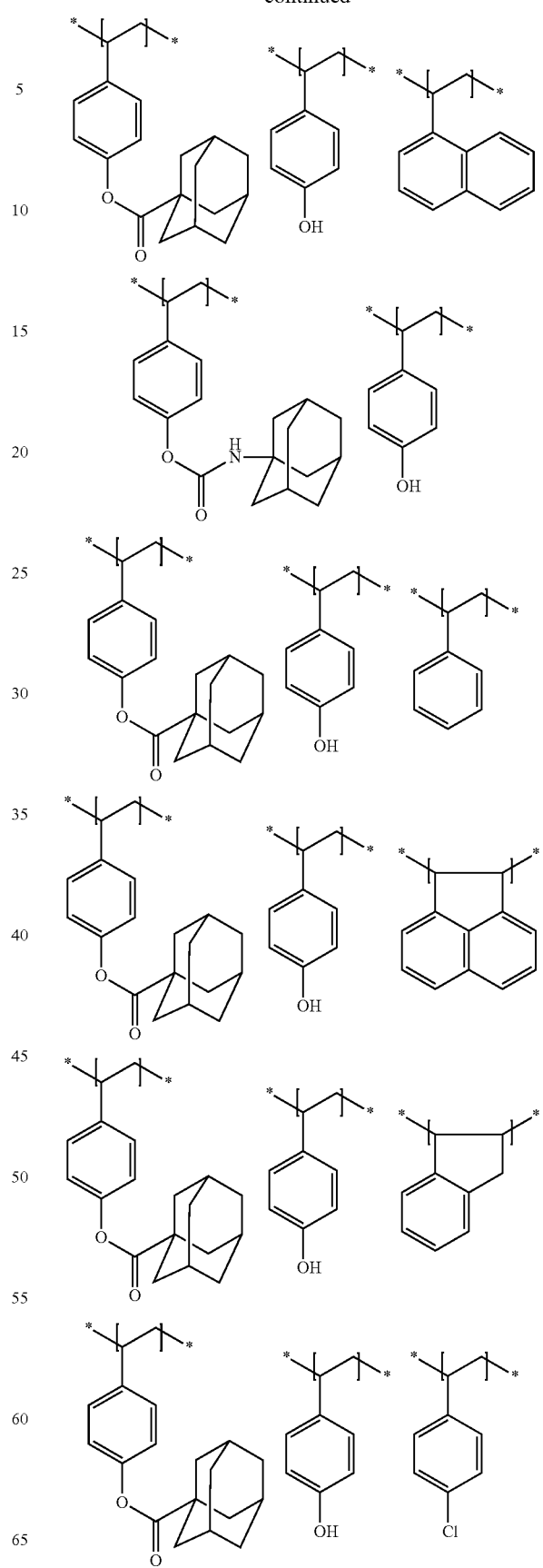

-continued

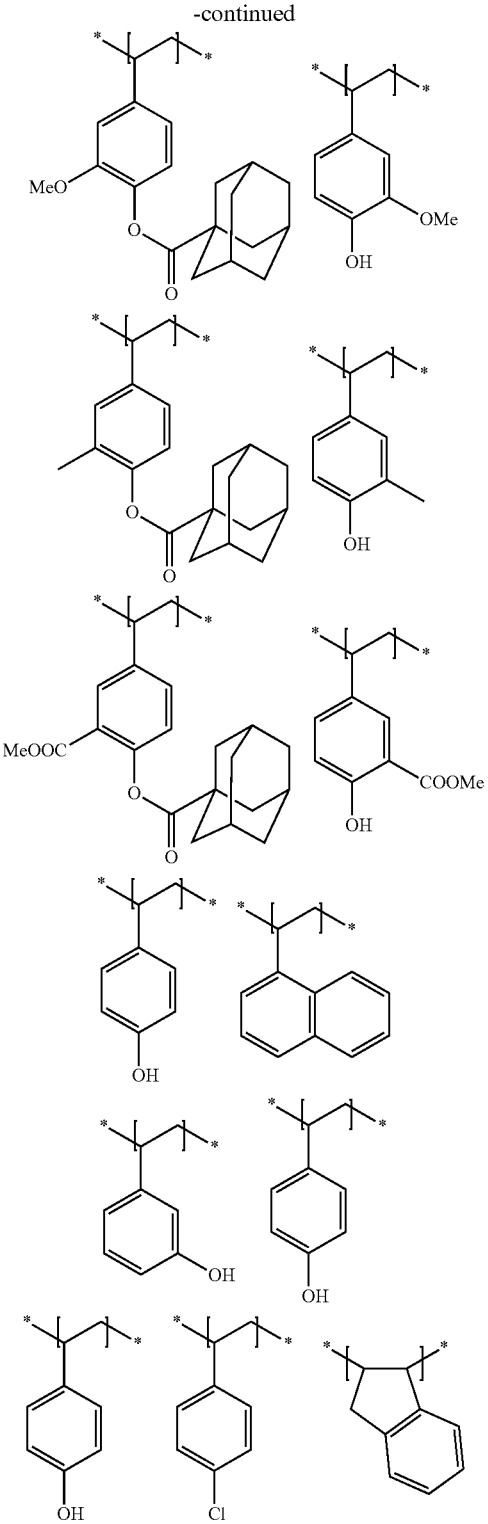

<Compound Capable of Generating Acid Upon Irradiation with Actinic Rays or Radiation>

The composition of the present invention may further contain a compound capable of generating an acid upon irradiation with actinic rays or radiation (hereinafter referred to as a "compound (B)", "acid generator", or "photoacid generator").

A preferred embodiment of the acid generator is an onium salt compound. Examples of the onium salt compound include a sulfonium salt, an iodonium salt, and a phosphonium salt.

Another preferred embodiment of the acid generator is a compound capable of generating a sulfonic acid, an imide acid, or a methide acid upon irradiation with actinic rays or radiation. Examples of the acid generator in this embodiment include a sulfonium salt, an iodonium salt, a phosphonium salt, oxime sulfonate, and imidosulfonate.

The acid generator is preferably a compound capable of generating an acid upon irradiation with an electron beam or extreme ultraviolet rays.

In the present invention, the onium salt compound is preferably a sulfonium compound represented by the following General Formula (7) or an iodonium compound represented by General Formula (8):

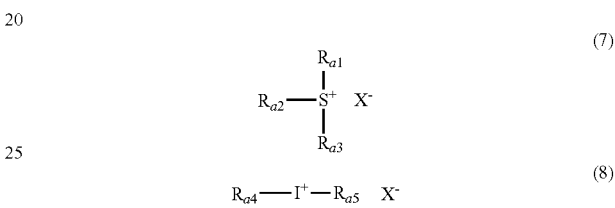

In General Formula (7) and General Formula (8), each of $R_{a1}$, $R_{a2}$, $R_{a3}$, $R_{a4}$, and $R_{a5}$ independently represents an organic group.

$X^-$ represents an organic anion.

Hereinafter, the sulfonium compound represented by General Formula (7) and the iodonium compound represented by General Formula (8) will be described in more detail.

Each of $R_{a1}$, $R_{a2}$, and $R_{a3}$ in General Formula (7) and $R_{a4}$ and $R_{a5}$ in General Formula (8) independently represents an organic group, as described above, and each of at least one of $R_{a1}$, $R_{a2}$, or $R_{a3}$ and at least one of $R_{a4}$ or $R_{a5}$ is preferably an aryl group. The aryl group is preferably a phenyl group or a naphthyl group, and more preferably a phenyl group.

Examples of the organic anion of $X^-$ in General Formulae (7) and (8) include a sulfonate anion, a carboxylate anion, a bis(alkylsulfonyl)amido anion, and a tris(alkylsulfonyl)methide anion. The organic anion is preferably an organic anion represented by the following General Formula (9), (10), or (11), and more preferably an organic anion represented by the following General Formula (9).

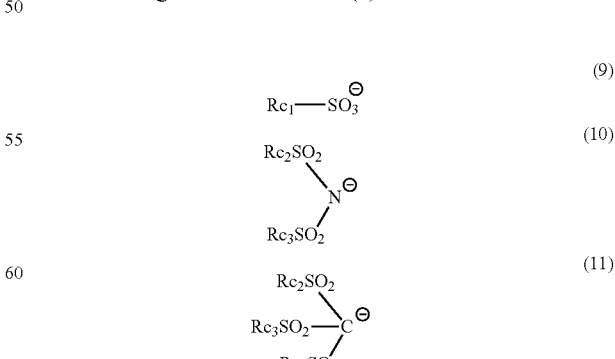

In General Formulae (9), (10), and (11), each of $Rc_1$, $Rc_2$, $Rc_3$, and $Rc_4$ independently represents an organic group.

The organic anion of X⁻ corresponds to a sulfonic acid, an imide acid, or a methide acid which is an acid generated upon irradiation with actinic rays or radiation such as an electron beam and extreme ultraviolet rays.

Examples of the organic group of $Rc_1$, $Rc_2$, $Rc_3$, and $Rc_4$ include an alkyl group, an aryl group, and a group formed by combining a plurality of such groups. Among these organic groups, more preferred are an alkyl group substituted with a fluorine atom or a fluoroalkyl group at the 1-position, and a phenyl group substituted with a fluorine atom or a fluoroalkyl group. By having a fluorine atom or a fluoroalkyl group, the acidity of the acid generated by light irradiation is increased and the sensitivity is enhanced. However, the terminal group preferably contains no fluorine atom as a substituent.

Also, in the present invention, in view of suppressing diffusion of an acid generated by exposure into a non-exposed area, thereby improving a resolution or a pattern profile, the compound (B) is preferably a compound which generates an acid with a volume of 130 Å³ or more (more preferably, a sulfonic acid), more preferably a compound which generates an acid with a volume of 190 Å³ or more (more preferably, a sulfonic acid), still more preferably, a compound which generates an acid with a volume of 270 Å³ or more (more preferably, a sulfonic acid), and particularly preferably a compound which generates an acid with a volume of 400 Å³ or more (more preferably, a sulfonic acid). Meanwhile, in view of the sensitivity or the coating solvent solubility, the volume is preferably 2,000 Å³ or less, and more preferably 1,500 Å³ or less. The value of the volume was obtained using "WinMOPAC" manufactured by FUJITSU LIMITED. That is, the "accessible volume" of each acid may be calculated by, first, inputting a chemical structure of an acid according to each case, determining the most stable conformation of each acid by a molecular force field calculation using a MM3 method with an initial structure of this structure, and then performing a molecular orbital calculation using a PM3 method for the most stable conformation.

Hereinafter, a particularly preferred acid generator in the present invention will be exemplified. Also, some examples are given calculated values of volume (unit: Å³). Meanwhile, the value calculated herein is a volume value of an acid in which a proton is bound to an anion moiety.

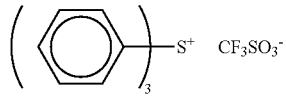
(z1)

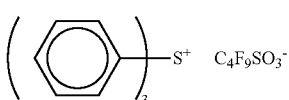
(z2)
113 Å³

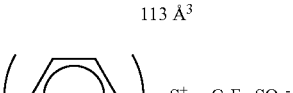
(z3)
220 Å³

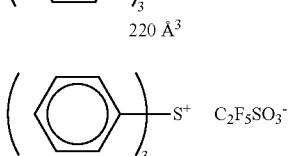
(z4)

-continued

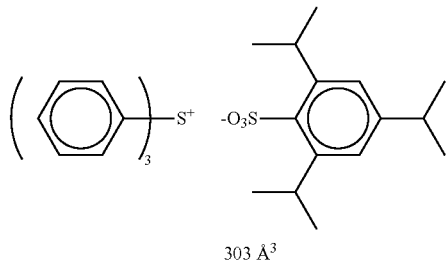
(z5)
303 Å³

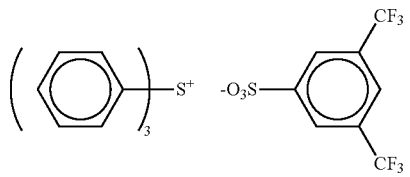
(z6)

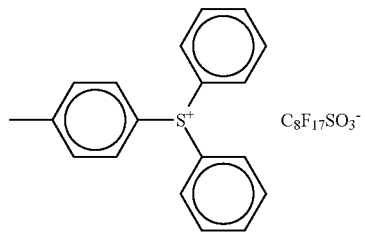
(z7)

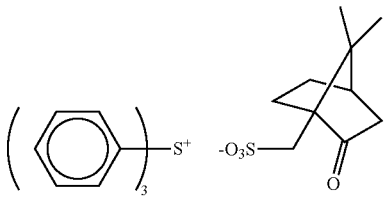
(z8)
216 Å³

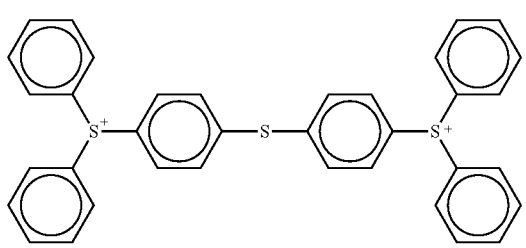
(z9)

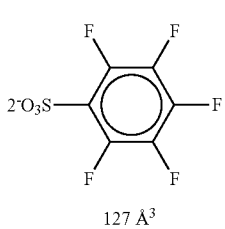
127 Å³

(z10)
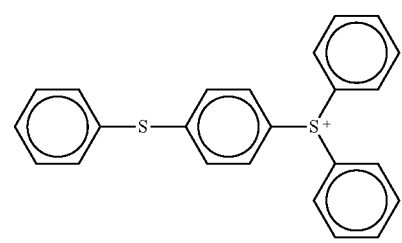
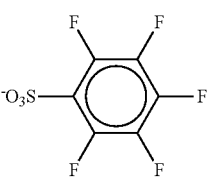
127 Å³
(z11)
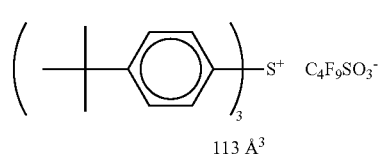
113 Å³
(z12)
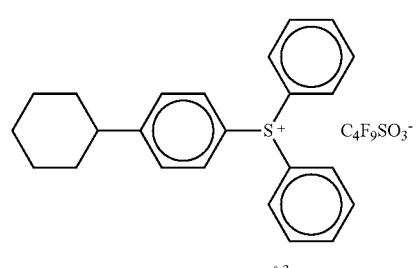
113 Å³
(z13)
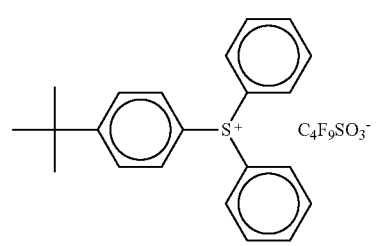
113 Å³
(z14)
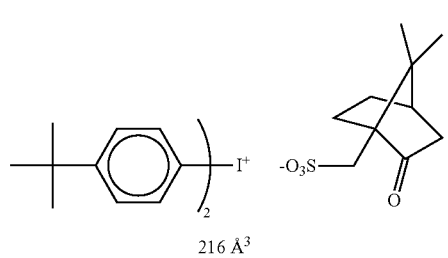
216 Å³
(z15)
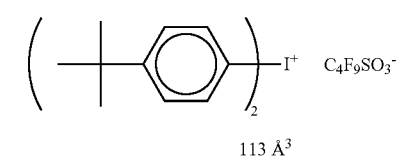
113 Å³
(z16)
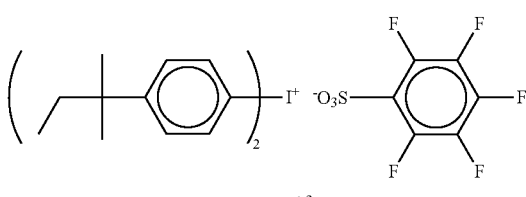
127 Å³
(z17)
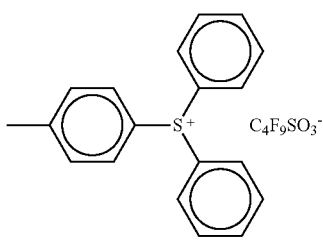
113 Å³
(z18)
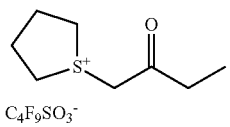
$C_4F_9SO_3^-$
113 Å³
(z19)
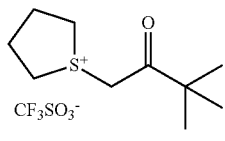
$CF_3SO_3^-$
113 Å³
(z20)
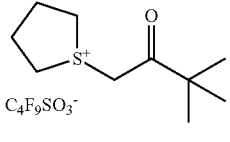
$C_4F_9SO_3^-$
113 Å³
(z21)
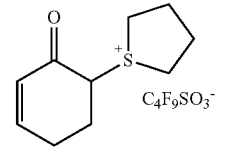
113 Å³
(z22)
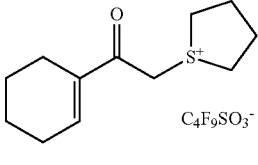
113 Å³

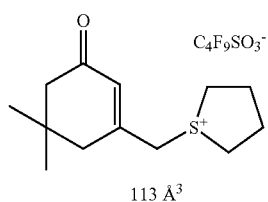
(z23)
113 Å³
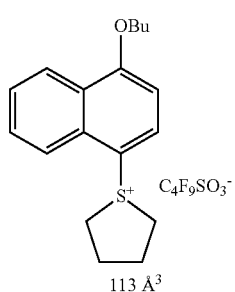
(z24)
113 Å³
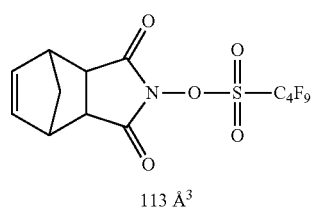
(z25)
113 Å³
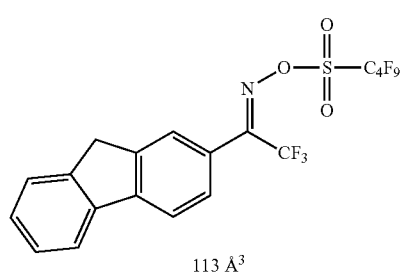
(z26)
113 Å³
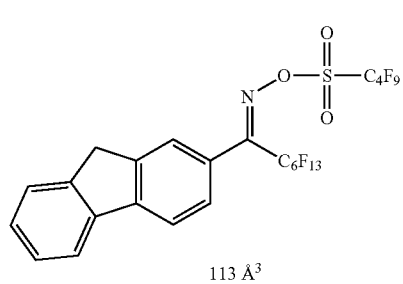
(z27)
113 Å³
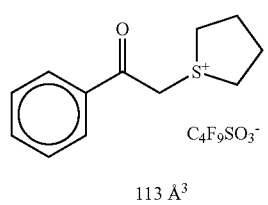
(z28)
113 Å³
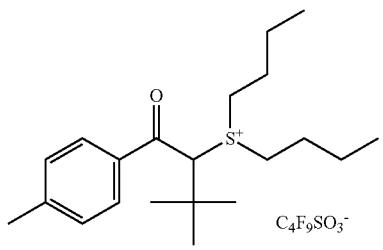
(z29)
113 Å³
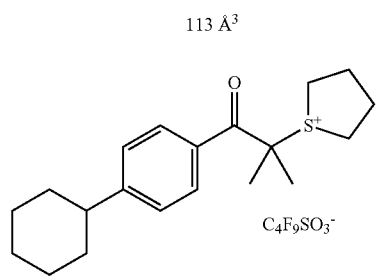
(z30)
113 Å³
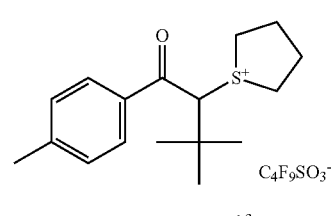
(z31)
113 Å³
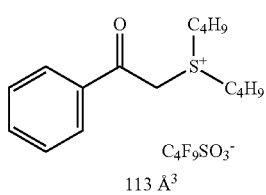
(z32)
113 Å³
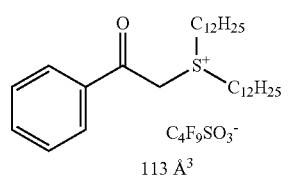
(z33)
113 Å³
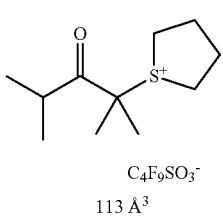
(z34)
113 Å³

-continued
(z35)
113 Å³
(z36)
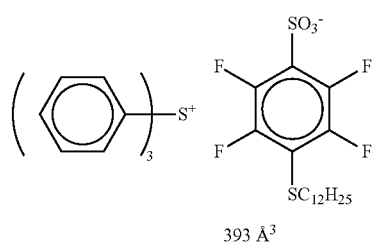
393 Å³
(z37)
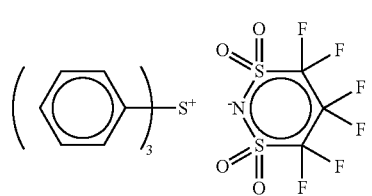
136 Å³
(z38)
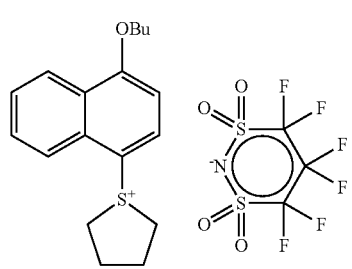
136 Å³
(z40)
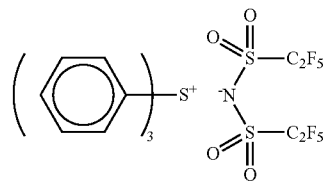
173 Å³
(z42)
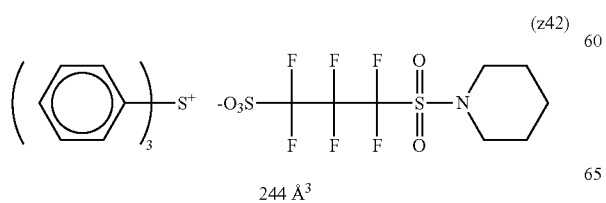
244 Å³
-continued
(z43)
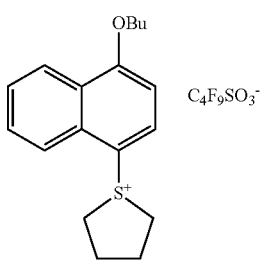
113 Å³
(z44)
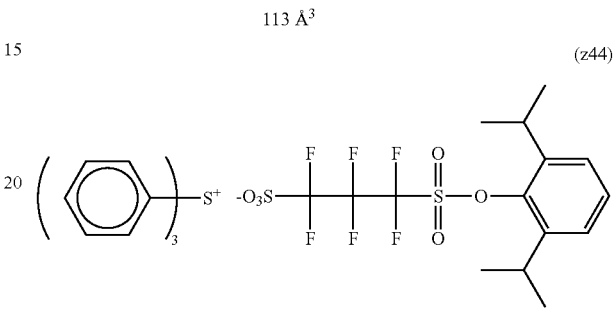
347 Å³
(z45)
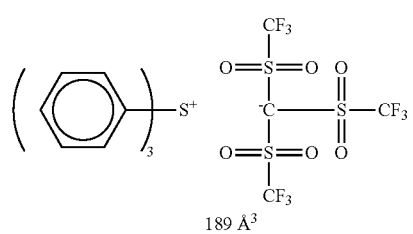
189 Å³
(z46)
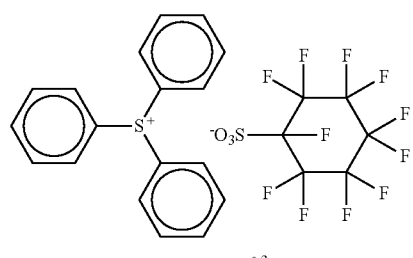
136 Å³
(z47)
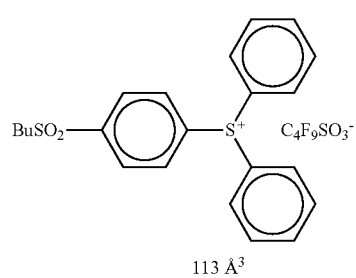
113 Å³

(z48)
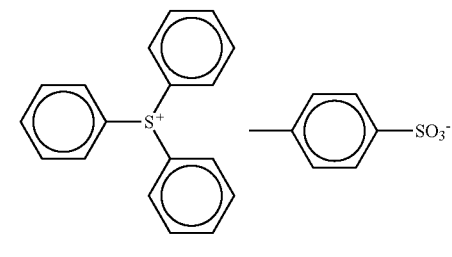
186 Å³
(z49)
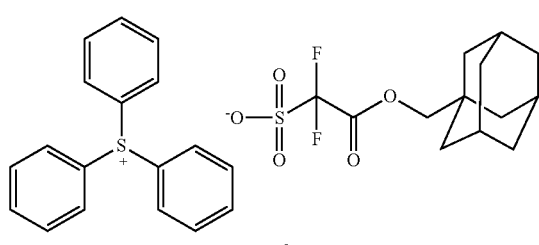
271 Å³
(z50)
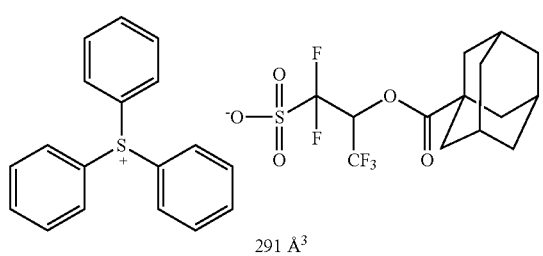
291 Å³
(z51)
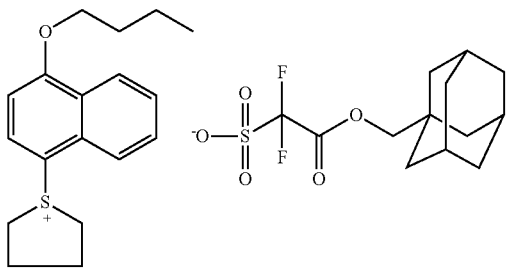
271 Å³
(z52)
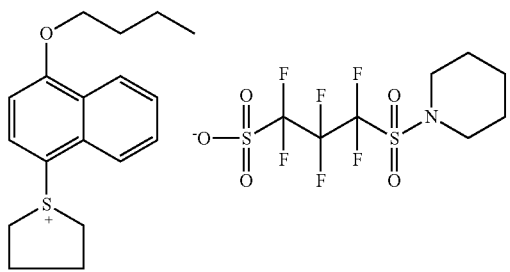
244 Å³
(z53)
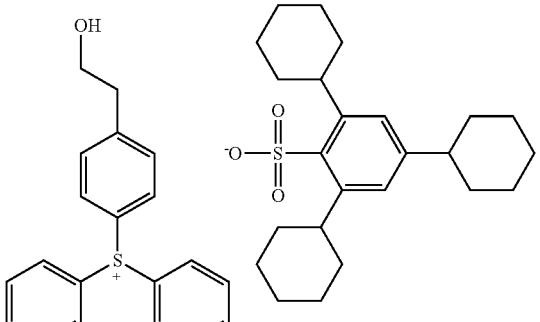
437 Å³
(z54)
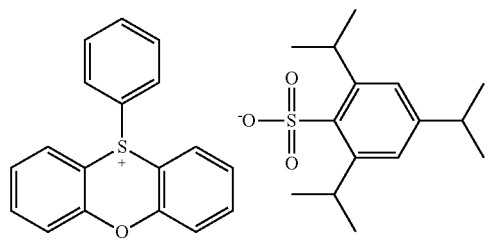
303 Å³
(z55)
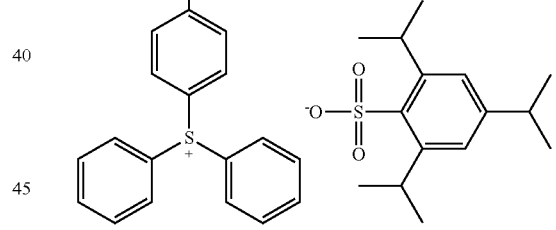
303 Å³
(z56)
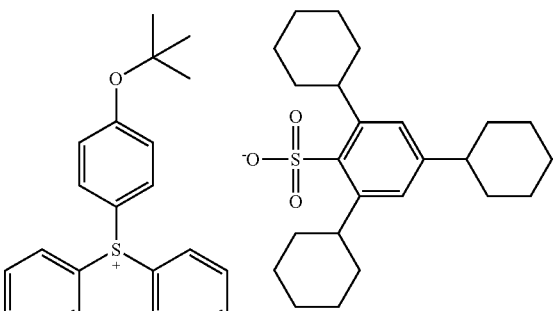
437 Å³

(z57)
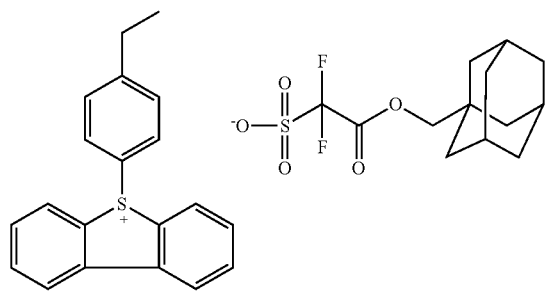
271 Å³
(z58)
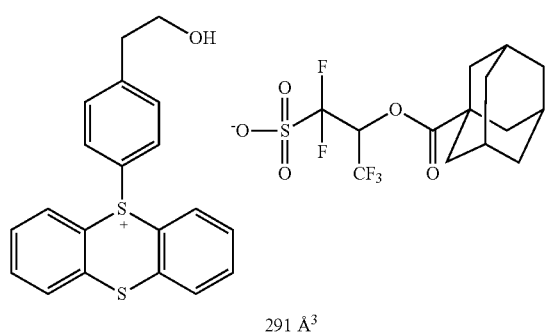
291 Å³
(z59)
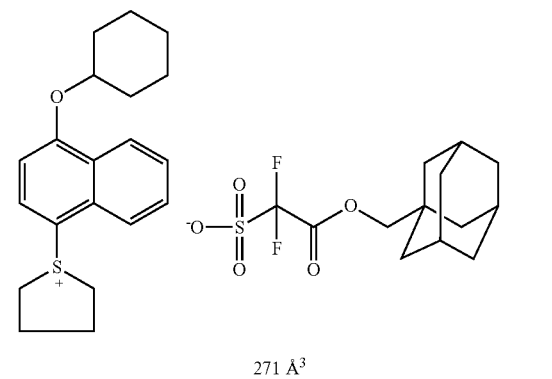
271 Å³
(z60)
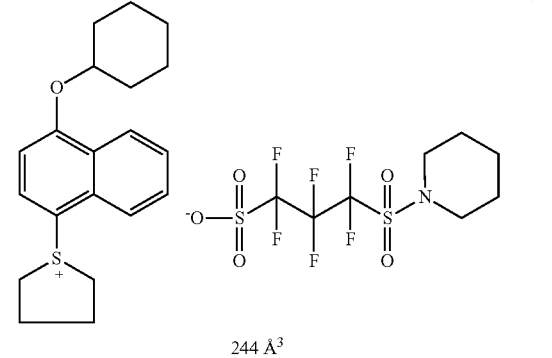
244 Å³
(z61)
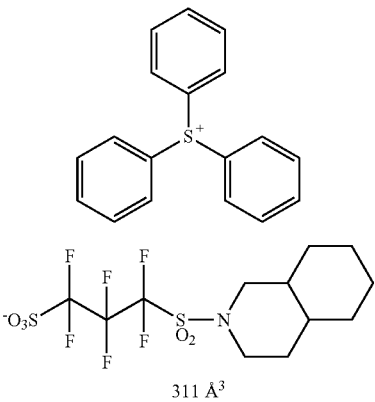
311 Å³
(z62)
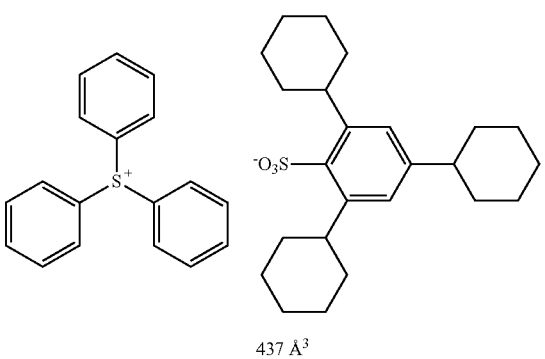
437 Å³
(z63)
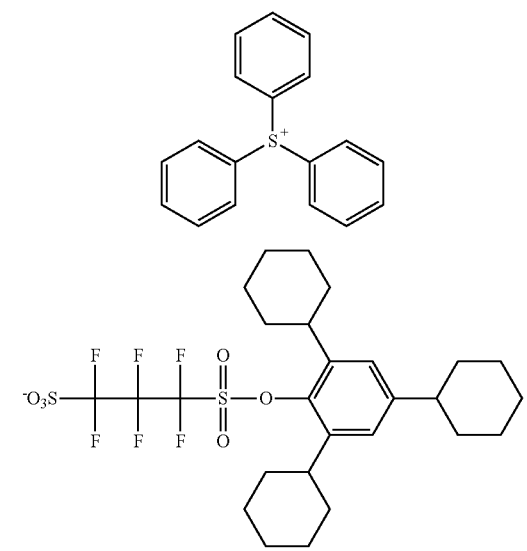
535 Å³

-continued (z64)
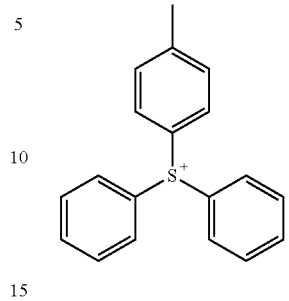

437 Å³

(z67)
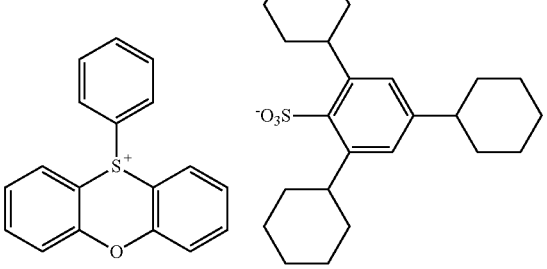

437 Å³

(z65)
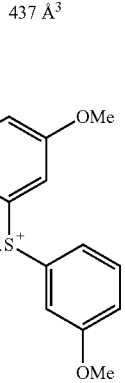

(z68)

437 Å³

(z66)
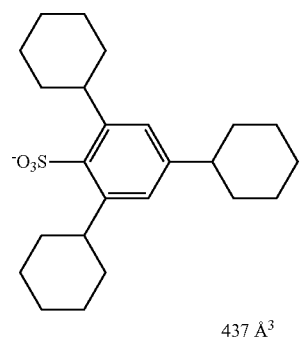

437 Å³

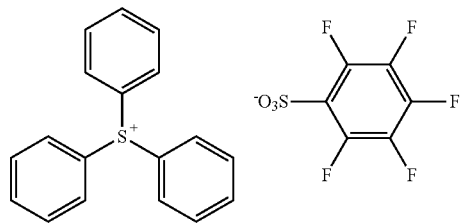

127 Å³

As the acid generator (preferably an onium compound) for use in the present invention, a polymer-type acid generator where a group capable of generating an acid upon irradiation with actinic rays or radiation (photoacid-generating group) is introduced into the main or side chain of a polymer compound may also be used.

The content of the acid generator in the composition is preferably 0.1 mass % to 25 mass %, more preferably 0.5 mass % to 20 mass %, and still more preferably 1 mass % to 18 mass %, based on the total solid content of the composition.

The acid generator may be used alone or in combination of two or more thereof.

<Another Crosslinking Agent>

The composition of the present invention may further contain another crosslinking agent (hereinafter referred to also as a "compound (C')" or "another crosslinking agent") other than the above-mentioned crosslinking agent (C) of the present invention. The compound (C') is preferably a compound containing two or more hydroxymethyl groups or alkoxymethyl groups within the molecule. Further, the compound (C') preferably contains a methylol group from the viewpoint of improving LER.

First, description will be made on the case where the compound (C') is a low molecular weight compound (hereinafter referred to as compound (C'-1)). Preferred examples of the compound (C'-1) include hydroxymethylated or alkoxymethylated phenol compounds, alkoxymethylated melamine-based compounds, alkoxymethyl glycoluril-based compounds, and alkoxymethylated urea-based compounds. The particularly preferred compound (C'-1) is a phenol derivative or alkoxymethyl glycoluril derivative hav-

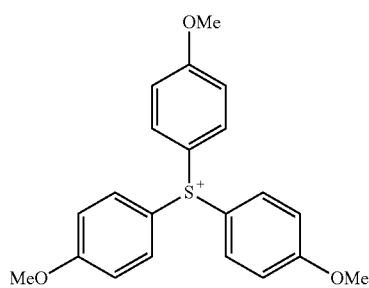

ing a molecular weight of 1,200 or less and containing, within the molecule, 3 to 5 benzene rings and a total of two or more hydroxymethyl groups or alkoxymethyl groups. The alkoxymethyl group is preferably a methoxymethyl group or an ethoxymethyl group.

Among examples of the compound (C'-1), a phenol derivative having a hydroxymethyl group may be obtained by reacting a corresponding phenol compound having no hydroxymethyl group with formaldehyde in the presence of a base catalyst. Also, a phenol derivative having an alkoxymethyl group may be obtained by reacting a corresponding phenol derivative having a hydroxymethyl group with an alcohol in the presence of an acid catalyst.

As for other preferred examples of the compound (C'-1), compounds having an N-hydroxymethyl group or an N-alkoxymethyl group, such as alkoxymethylated melamine-based compounds, alkoxymethyl glycoluril-based compounds, and alkoxymethylated urea-based compounds may be further exemplified.

As for such compounds, hexamethoxymethylmelamine, hexaethoxymethylmelamine, tetramethoxymethyl glycoluril, 1,3-bismethoxymethyl-4,5-bismethoxyethyleneurea, and bismethoxymethylurea may be exemplified, which are disclosed in EP0133216A, DE3634671B, DE3711264B, and EP0212482A.

Among specific examples of the compound (C'-1), particularly preferred are those illustrated below.

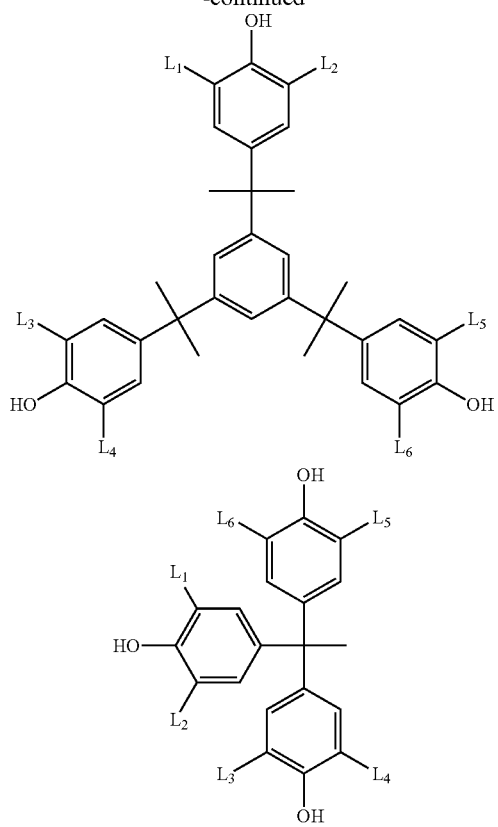

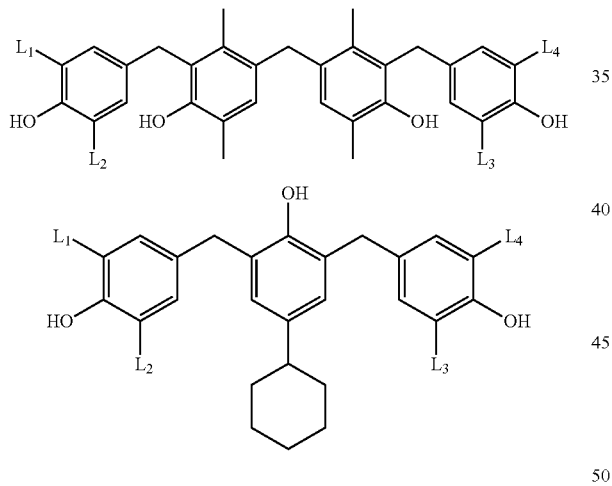

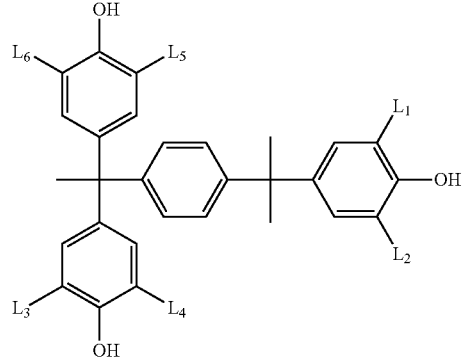

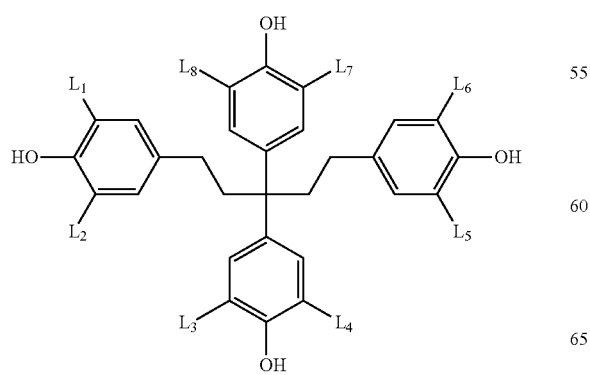

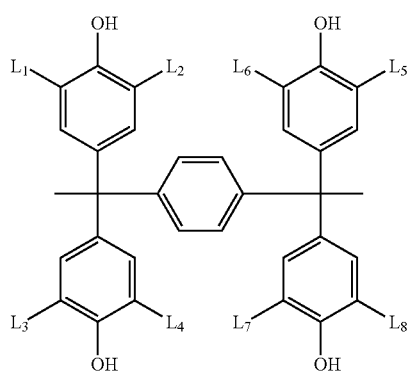

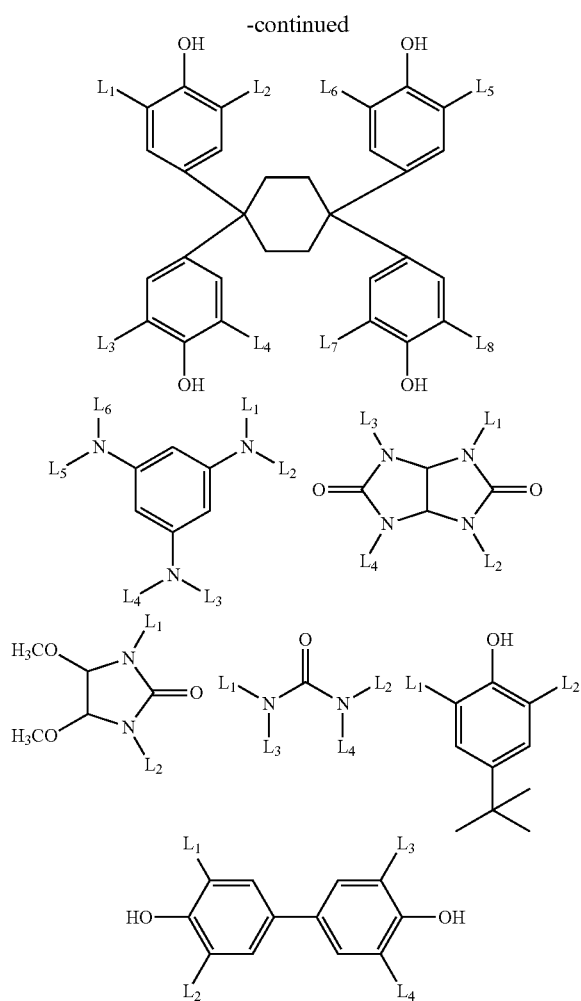

In these formulae, each of $L_1$ to $L_8$ independently represents a hydrogen atom, a hydroxymethyl group, a methoxymethyl group, an ethoxymethyl group, or an alkyl group having 1 to 6 carbon atoms.

In the present invention, the content of the compound (C'-1) is preferably 3 mass % to 65 mass %, and more preferably 5 mass % to 50 mass %, based on the total solid content of the composition of the present invention. When the content of the compound (C'-1) is within the range of 3 mass % to 65 mass %, good storage stability of the composition of the present invention can be maintained while preventing deterioration of the residual film ratio and resolution.

In the present invention, the compound (C'-1) may be used alone or in combination of two or more thereof. In view of good pattern profile, the compound (C'-1) is preferably used in combination of two or more thereof.

For example, in the case where another compound (C'-1), for example, the above-mentioned compound having an N-alkoxymethyl group is used in combination with the phenol derivative, the ratio of the phenol derivative to another compound (C'-1) is usually in a molar ratio of 90/10 to 20/80, preferably 85/15 to 40/60, and more preferably 80/20 to 50/50.

The compound (C') may be an embodiment of a resin containing a repeating unit having an acid-crosslinkable group (hereinafter, referred to also as "compound (C'-2)").

In the case of such an embodiment, because of inclusion of a crosslinking group in the molecule unit of the repeating unit, crosslinking reactivity is higher as compared with a conventional resin+crosslinking agent system (a composition containing a resin and a crosslinking agent). Due to such higher crosslinking reactivity, it is possible to form a hard film and therefore control the diffusion and dry etching resistance of an acid. As a result, since the diffusion of an acid in the areas exposed to actinic rays or radiation such as an electron beam or extreme ultraviolet rays is strongly inhibited, resolution, pattern profile, and LER in a fine pattern are excellent. Also, as in the repeating unit represented by the following General Formula (1), when the reaction point of the resin and the reaction point of the crosslinking groups are close to each other, a composition is achieved with improved sensitivity when forming a pattern.

The compound (C'-2) may be, for example, a resin containing a repeating unit represented by the following General Formula (1). The repeating unit represented by General Formula (1) is a structure containing at least one methylol group which may have a substituent.

As used herein, the term "methylol group" is a group represented by the following General Formula (M), and in one embodiment of the present invention, it is preferably a hydroxymethyl group or an alkoxymethyl group.

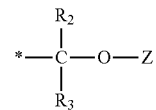

(M)

In the formula, $R_2$, $R_3$, and Z have the same definitions as those in General Formula (1) as described later.

First, General Formula (1) will be described.

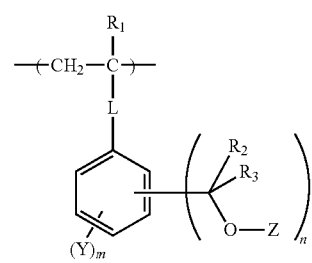

(1)

In General Formula (1), $R_1$ represents a hydrogen atom, a methyl group, or a halogen atom.

$R_2$ and $R_3$ represent a hydrogen atom, an alkyl group, or a cycloalkyl group.

L represents a divalent linking group or a single bond.

Y represents a substituent except for a methylol group.

Z represents a hydrogen atom or a substituent.

m represents an integer of 0 to 4.

n represents an integer of 1 to 5.

m+n is 5 or less.

In the case where m is 2 or more, plural Y's may be the same as or different from each other.

In the case where n is 2 or more, plural $R_2$'s, $R_3$'s, and Z's may be the same as or different from each other.

Furthermore, any two or more of Y, $R_2$, $R_3$, and Z may be bonded to each other to form a ring structure.

Each of $R_1$, $R_2$, $R_3$, L, and Y may have a substituent.

In addition, when m is 2 or more, plural Y's may be bonded to each other via a single bond or a linking group to form a ring structure.

Moreover, the repeating unit represented by General Formula (1) is preferably represented by the following General Formula (2) or (3).

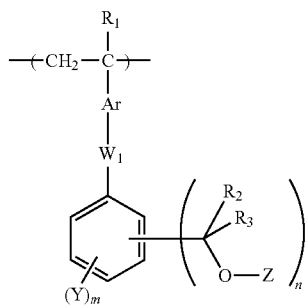
(2)

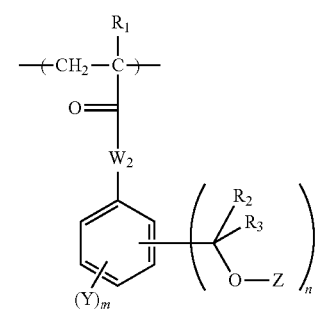
(3)

In General Formulae (2) and (3), $R_1$, $R_2$, $R_3$, Y, Z, m, and n are as defined in General Formula (1).

Ar represents an aromatic ring.

$W_1$ and $W_2$ represent a divalent linking group or a single bond.

Furthermore, the repeating unit represented by General Formula (1) is more preferably represented by the following General Formula (2') or (3').

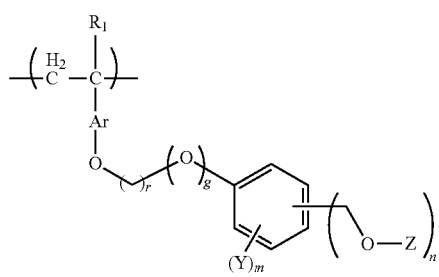
(2')

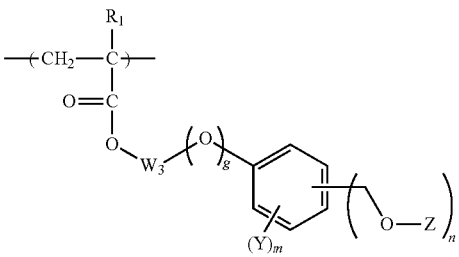
(3')

In General Formulae (2') and (3'), $R_1$, Y, Z, m, and n have the same definitions as the groups in General Formula (1), respectively. Ar in General Formula (2') has the same definition as Ar in General Formula (2).

In General Formula (3'), $W_3$ is a divalent linking group.

In General Formulae (2') and (3'), f is an integer of 0 to 6.

In General Formulae (2') and (3'), g is 0 or 1.

Furthermore, General Formula (2') is particularly preferably represented by any one of the following General Formulae (1-a) to (1-c). The compound (C'-2) particularly preferably contains a repeating unit represented by any one of the following General Formulae (1-a) to (1-c), or a repeating unit represented by General Formula (3').

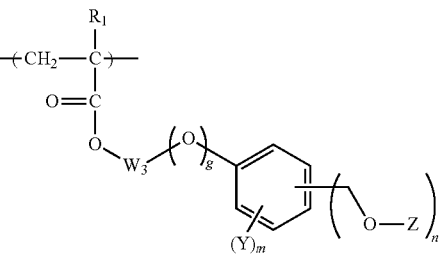
(1-a)

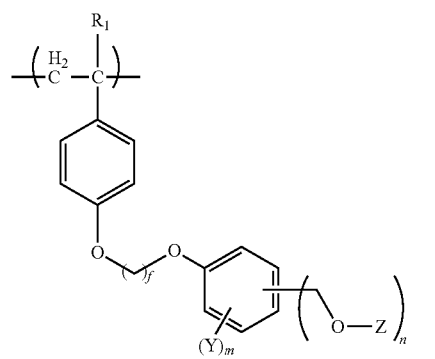
(1-b)

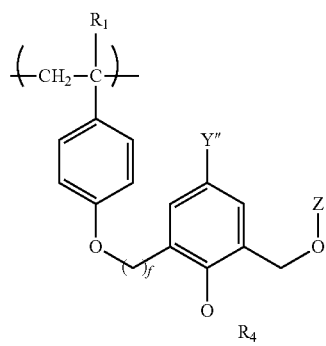

(1-c)

$R_1$, Y, and Z in General Formulae (1-a) to (1-c) have the same definitions as the groups in General Formula (1), respectively.

In General Formulae (1-a) to (1-c),

Y" represents a hydrogen atom or a monovalent substituent, provided that Y" may be a methylol group.

$R_4$ represents a hydrogen atom or a monovalent substituent.

f is an integer of 1 to 6.

m is 0 or 1 and n is an integer of 1 to 3.

The content of the repeating unit having an acid-crosslinkable group in the compound (C'-2) is preferably from 3 mol % to 40 mol %, and more preferably 5 mol % to 30 mole %, based on the total repeating units of the compound (C'-2).

The content of the compound (C'-2) is preferably 5 mass % to 50 mass %, and more preferably 10 mass % to 40 mass %, based on the total solid content of the composition of the present invention.

The compound (C'-2) may contain two or more repeating units having an acid-crosslinkable group, or may be used in combination of two or more compounds (C'-2). In addition, the compound (C'-1) and the compound (C'-2) may also be used in combination therewith.

Specific examples of the repeating unit having an acid-crosslinkable group contained in the compounds (C'-2) include the following structures.

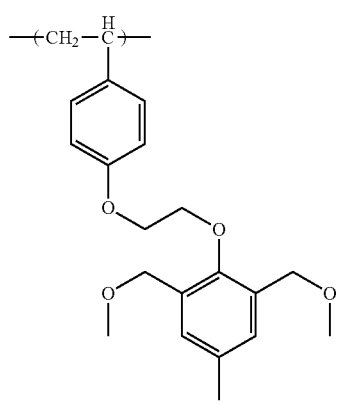

(Q-1)

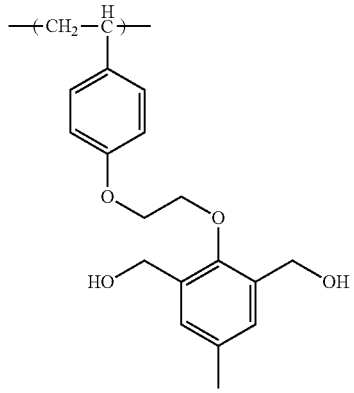

(Q-2)

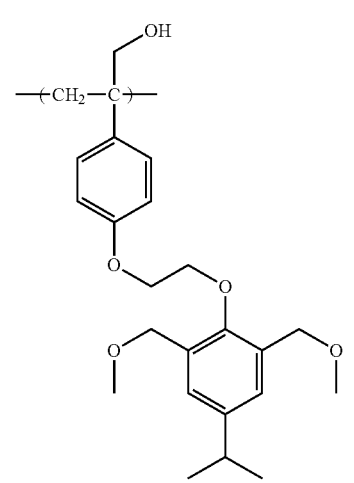

(Q-3)

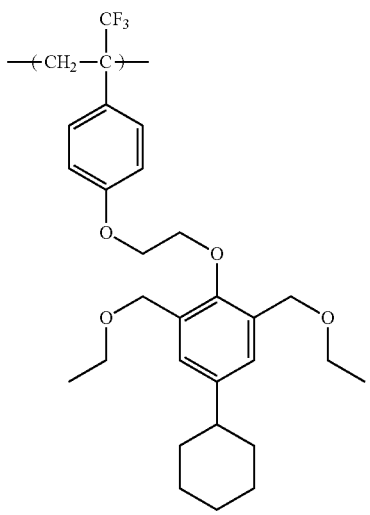

(Q-4)

(Q-5) 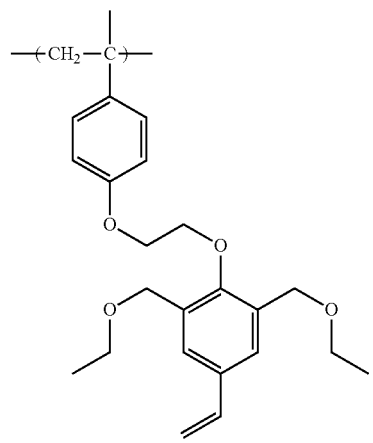
(Q-8) 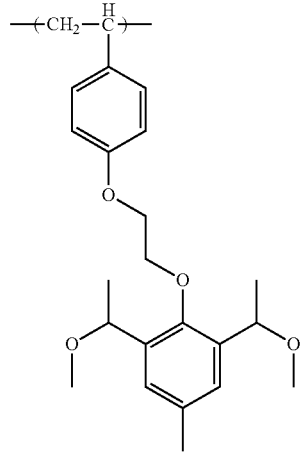
(Q-6) 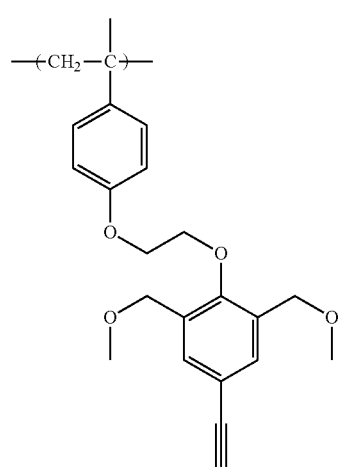
(Q-9) 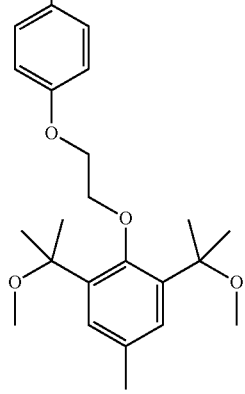
(Q-7) 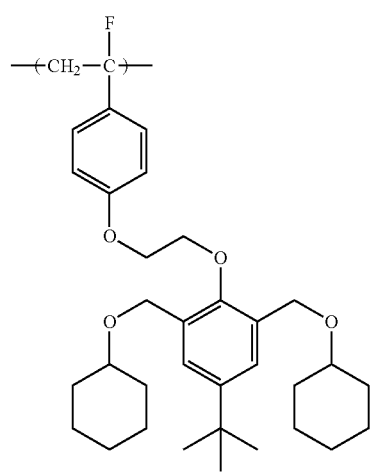
(Q-10) 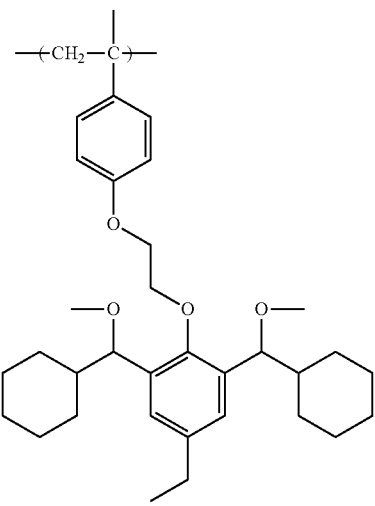

(Q-11) 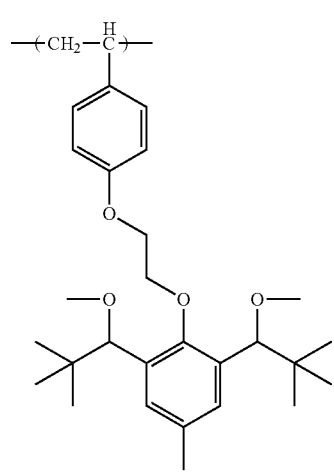
(Q-12) 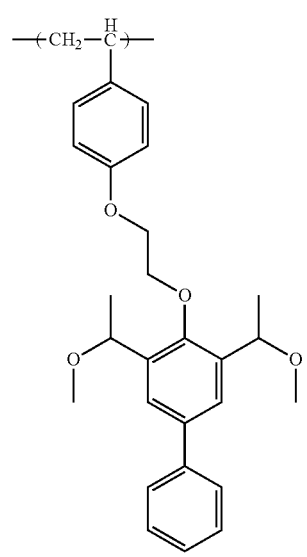
(Q-13) 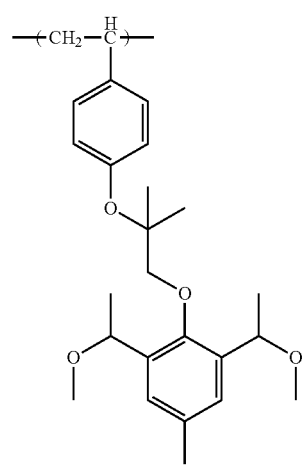
(Q-14) 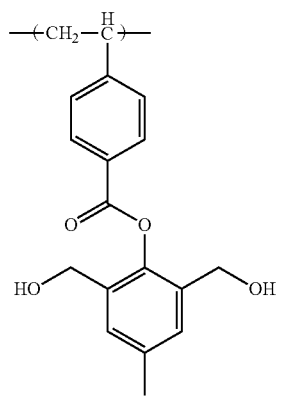
(Q-15) 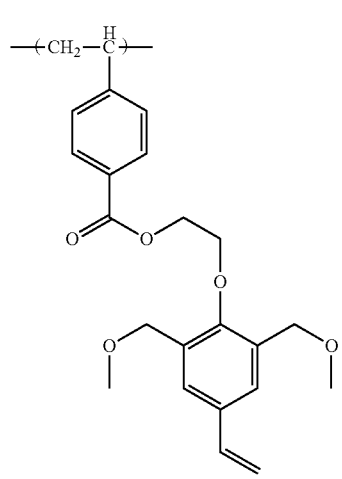
(Q-16) 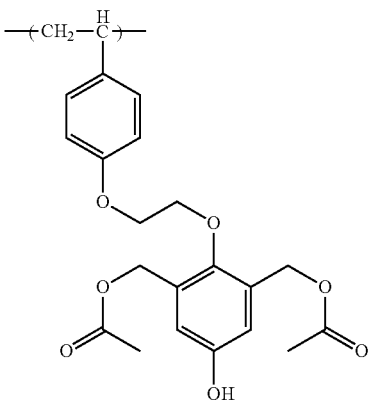

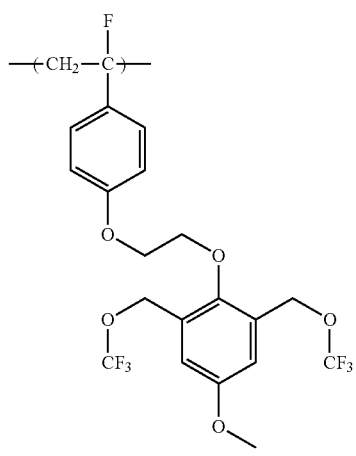
(Q-17)
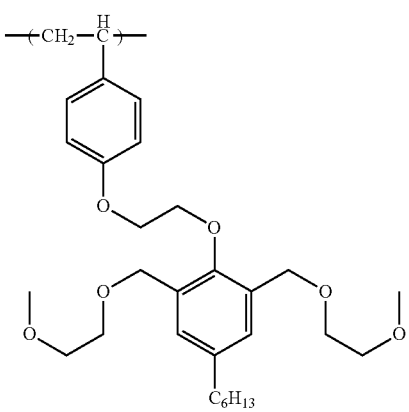
(Q-20)
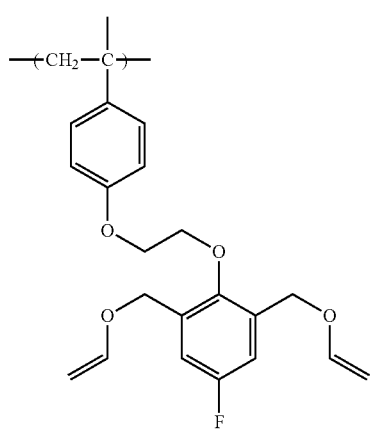
(Q-18)
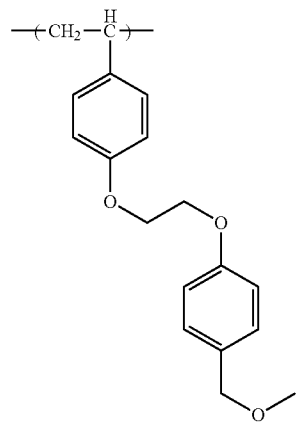
(Q-21)
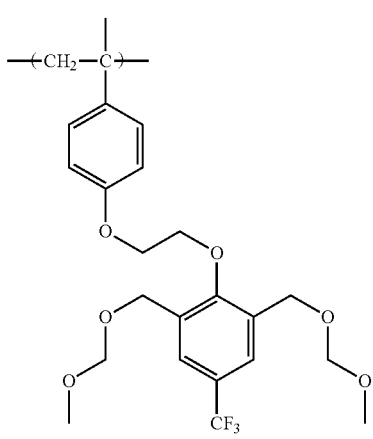
(Q-19)
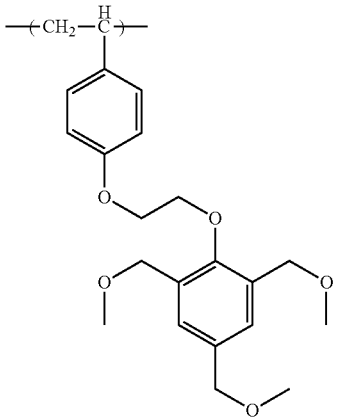
(Q-22)

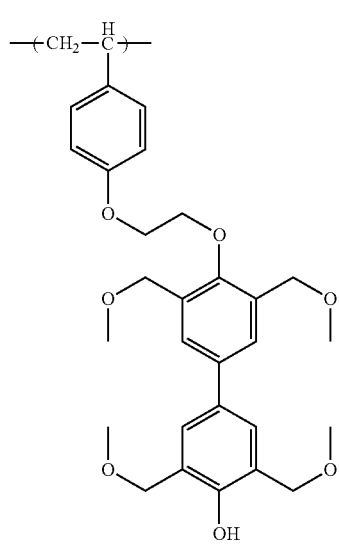
(Q-23)
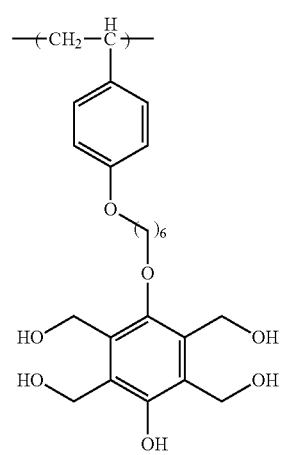
(Q-26)
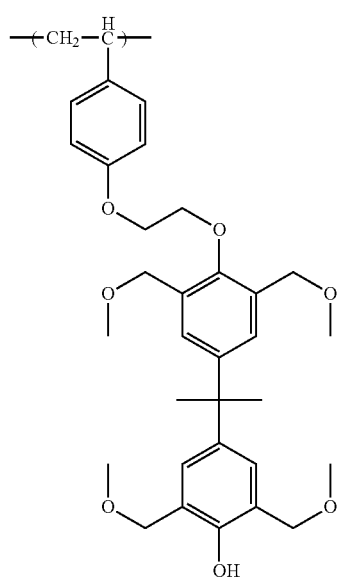
(Q-24)
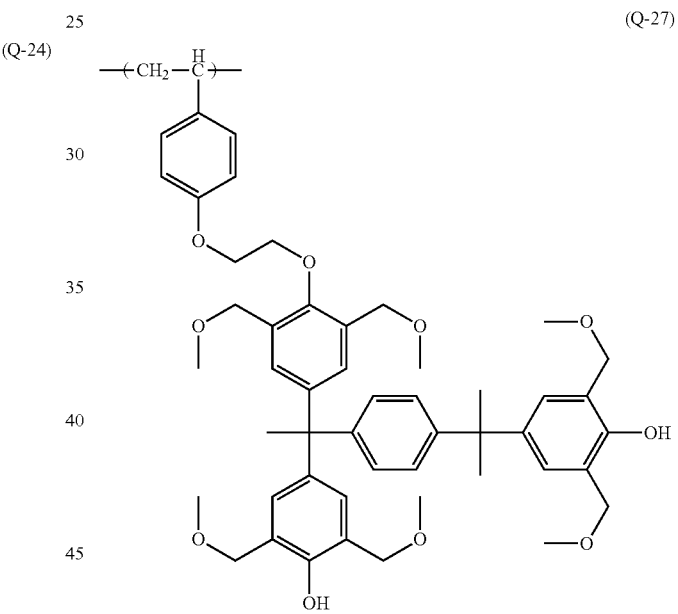
(Q-27)
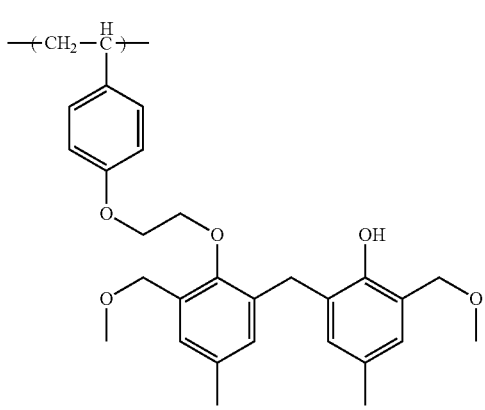
(Q-25)
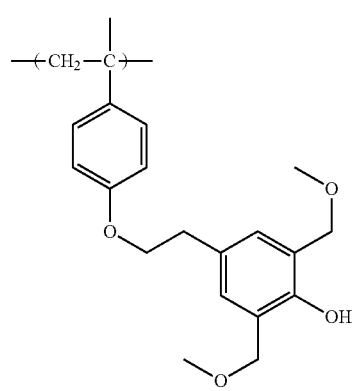
(Q-28)

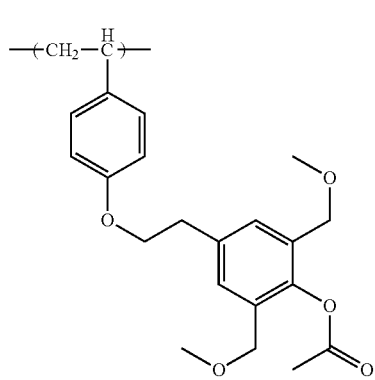
(Q-29)
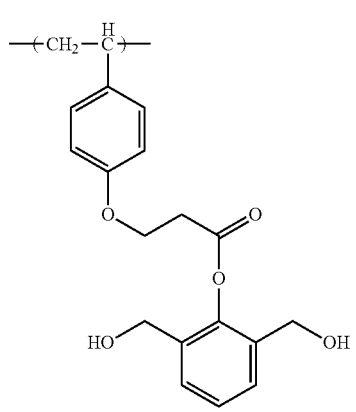
(Q-33)
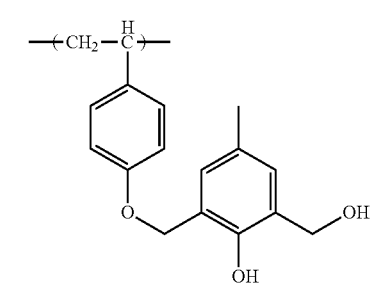
(Q-30)
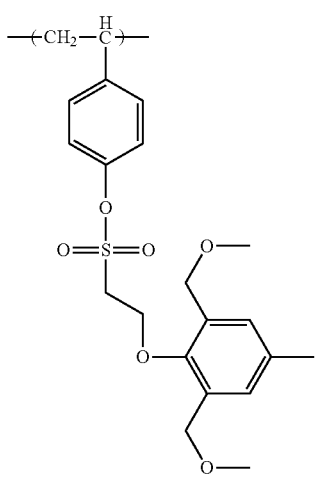
(Q-34)
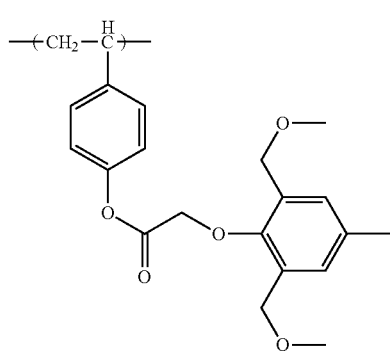
(Q-31)
(Q-32)
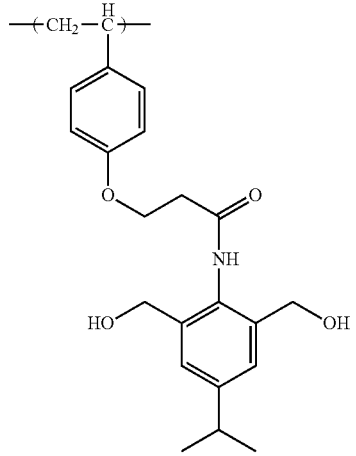
(Q-35)
(Q-36)

(Q-37)
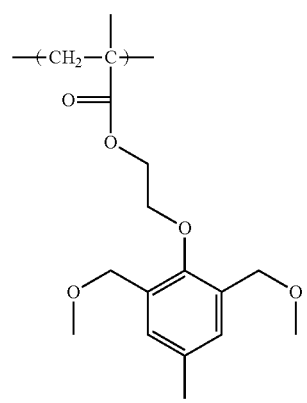
(Q-38)
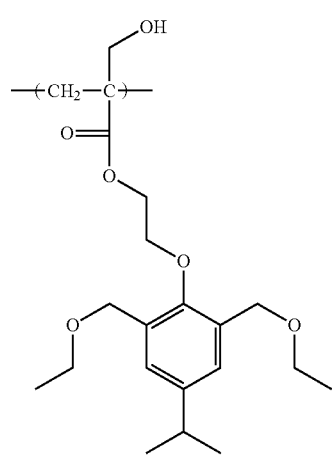
(Q-39)
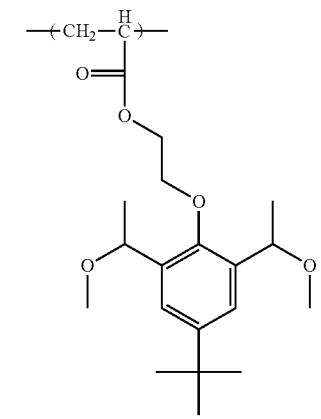
(Q-40)
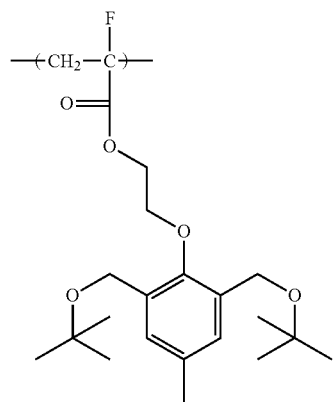
(Q-41)
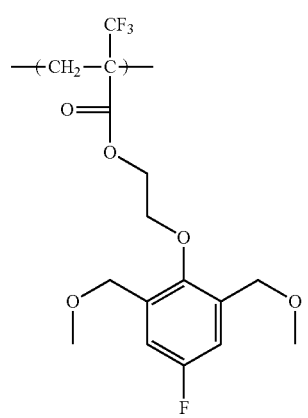
(Q-42)
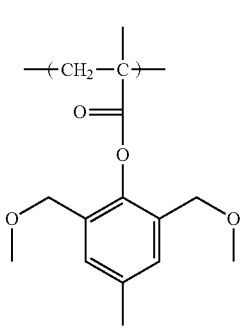
(Q-43)
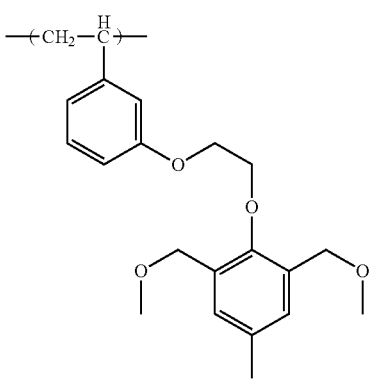

(Q-44) 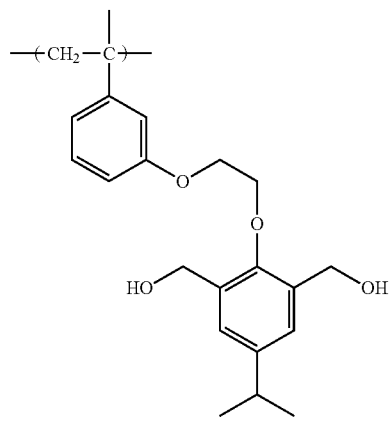
(Q-45) 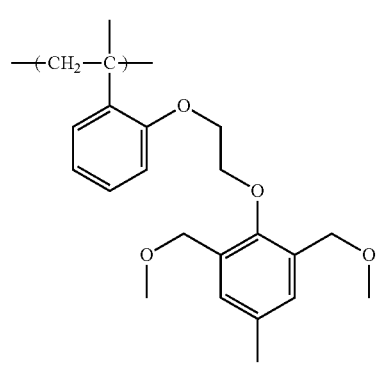
(Q-46) 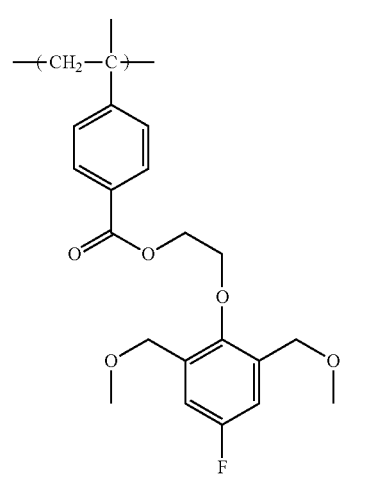
(Q-47) 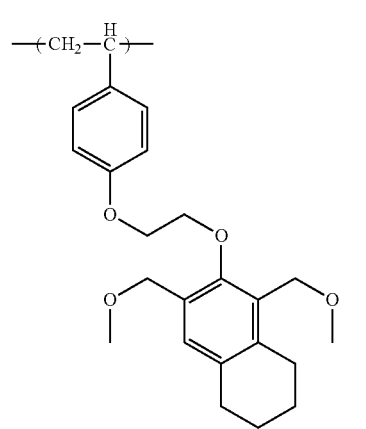
(Q-48) 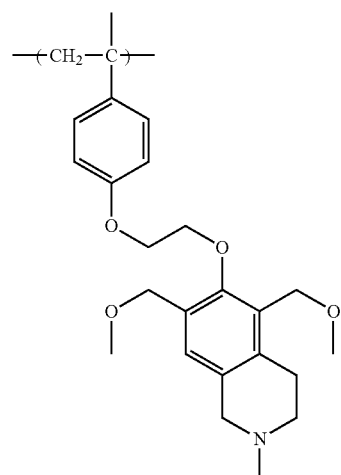
(Q-49) 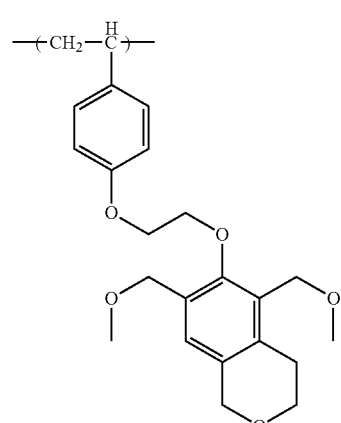
(Q-50) 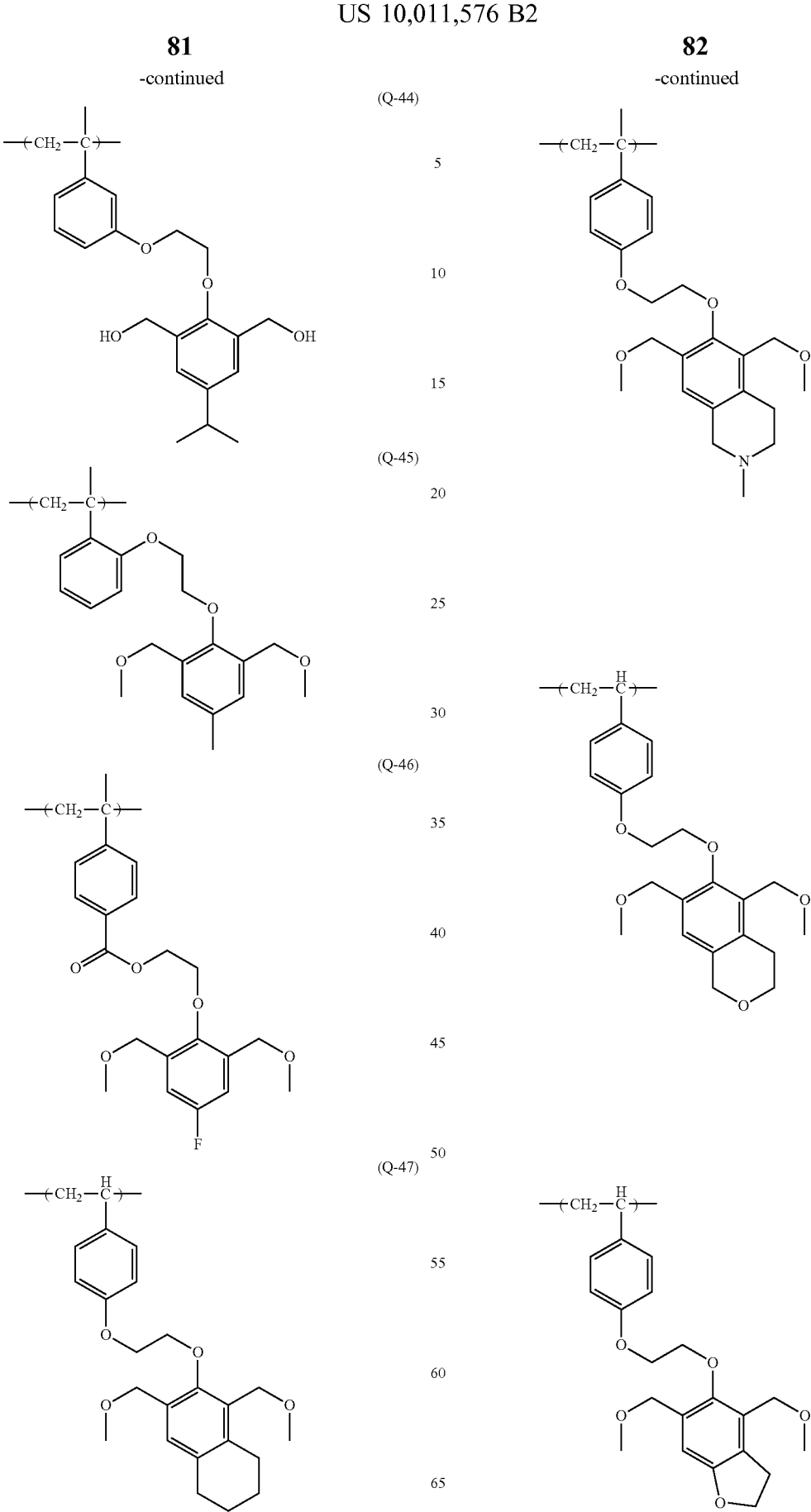

(Q-51) 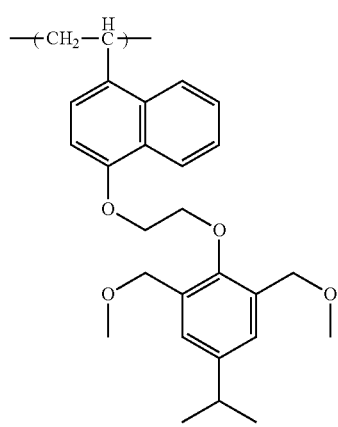
(Q-52) 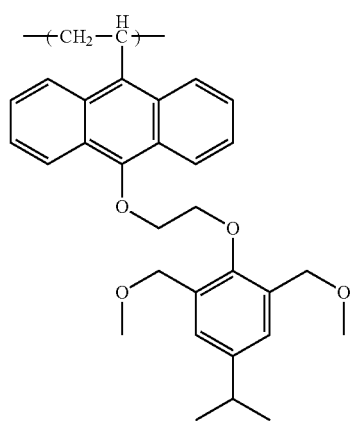
(Q-53) 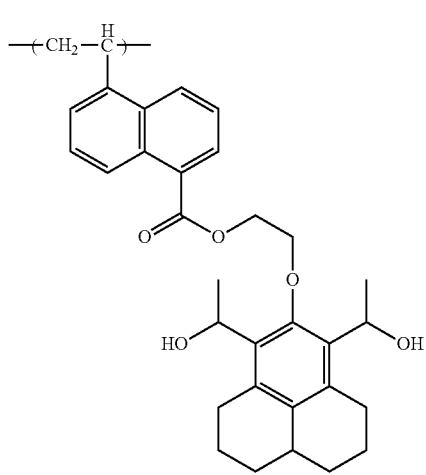
(Q-54) 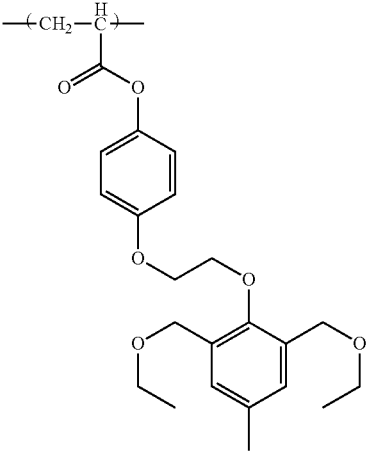
(Q-55) 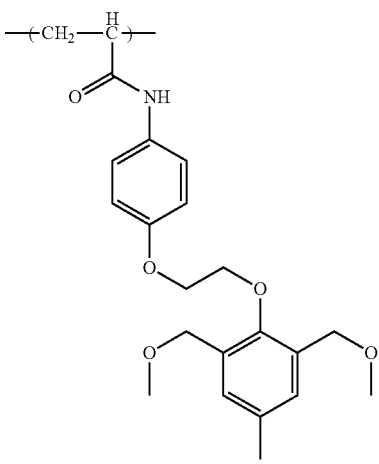
(Q-56) 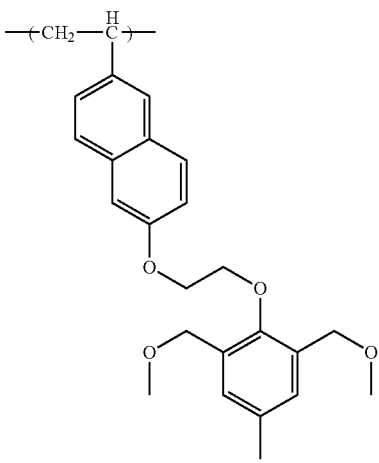

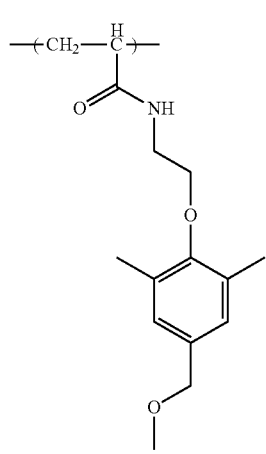
(Q-57)
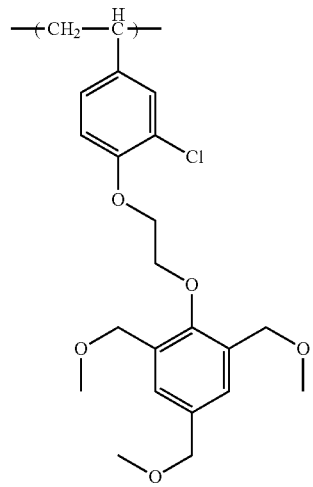
(Q-58)
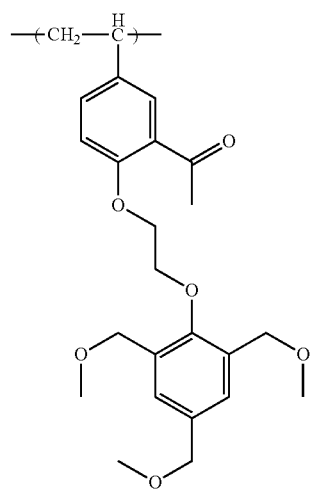
(Q-59)
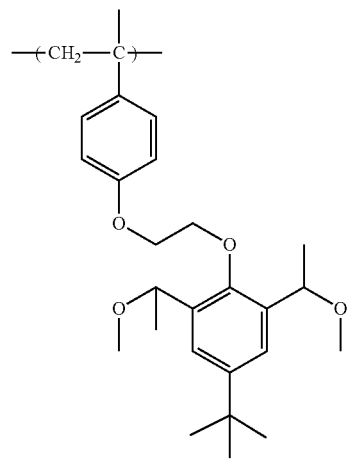
(Q-60)
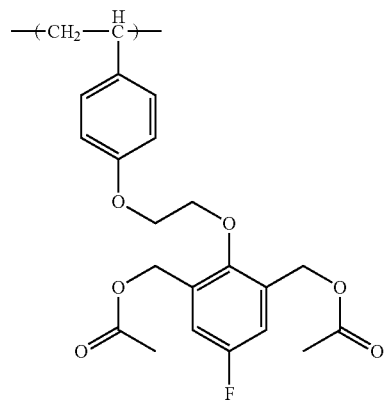
(Q-61)
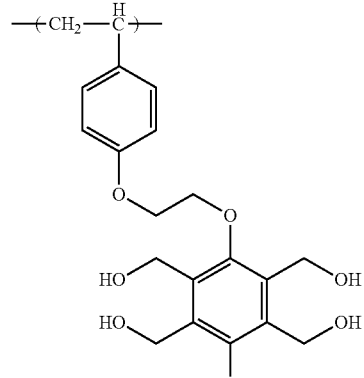
(Q-62)

(Q-63)
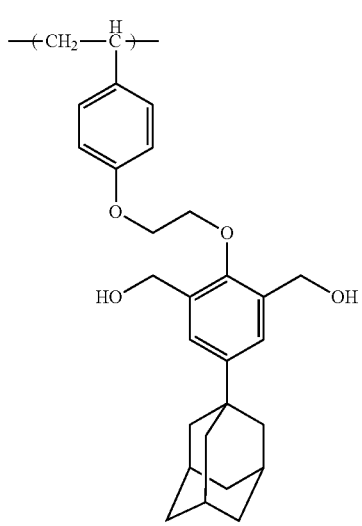
(Q-64)
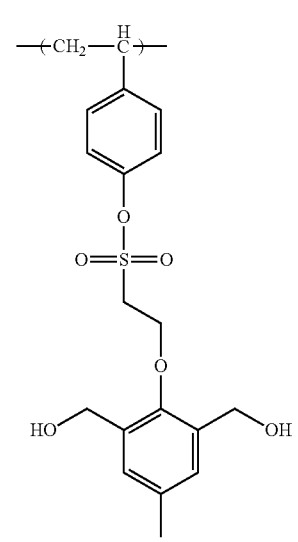
(Q-65)
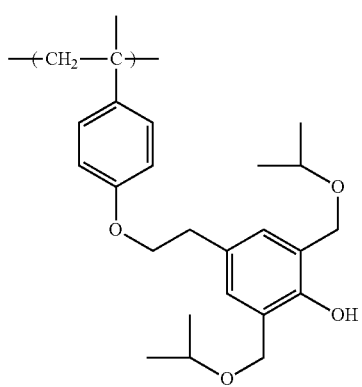
(Q-66)
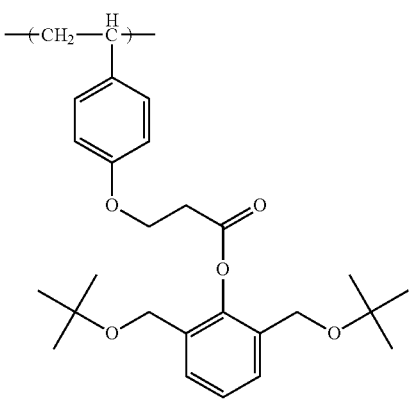
(Q-67)
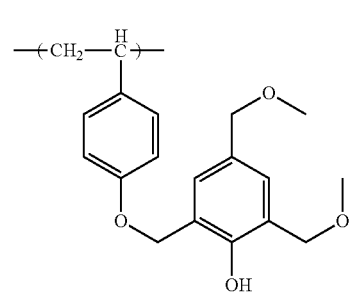
(Q-68)
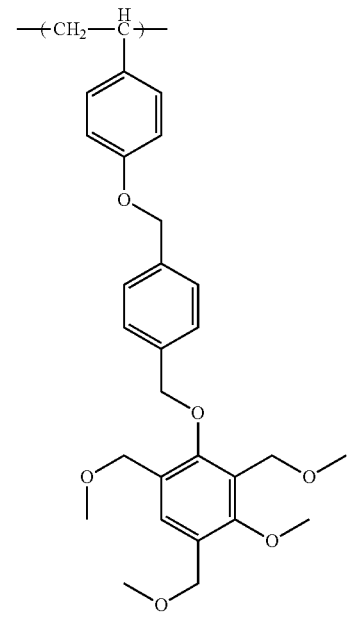

(Q-69)
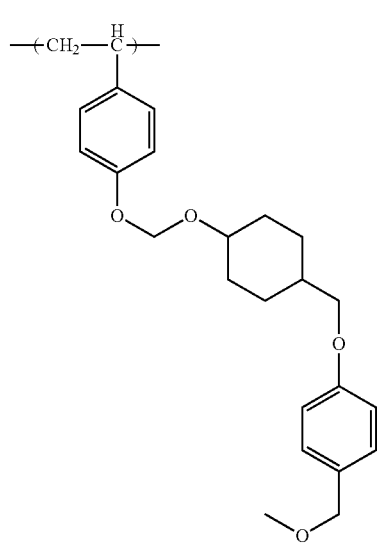
(Q-70)
(Q-71)
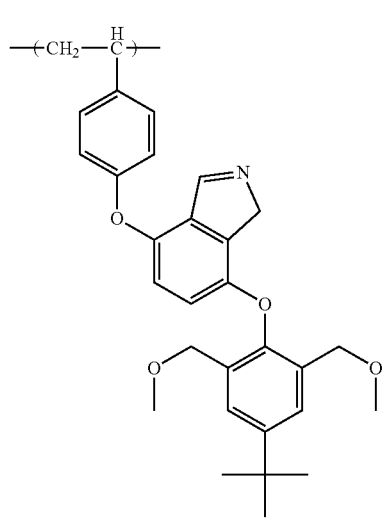
(Q-72)
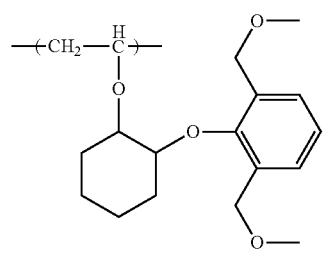
(Q-73)
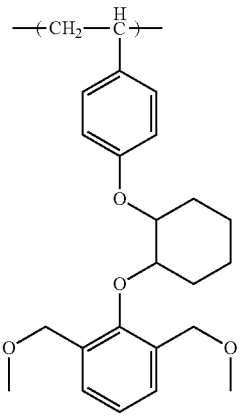
(Q-74)
(Q-75)
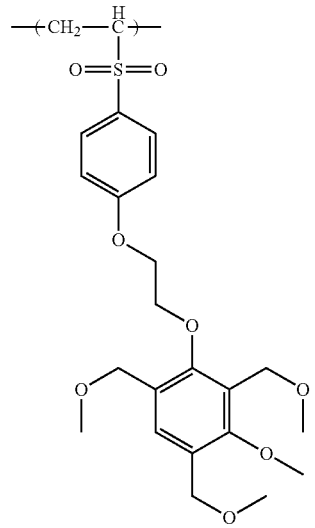

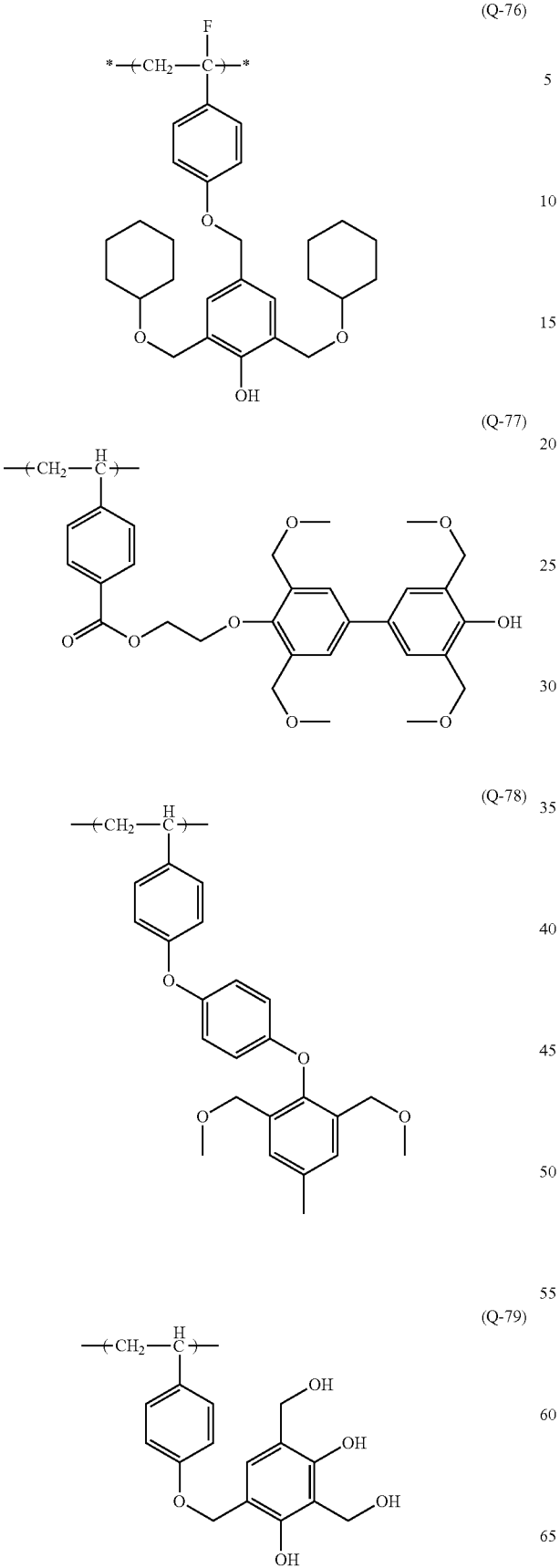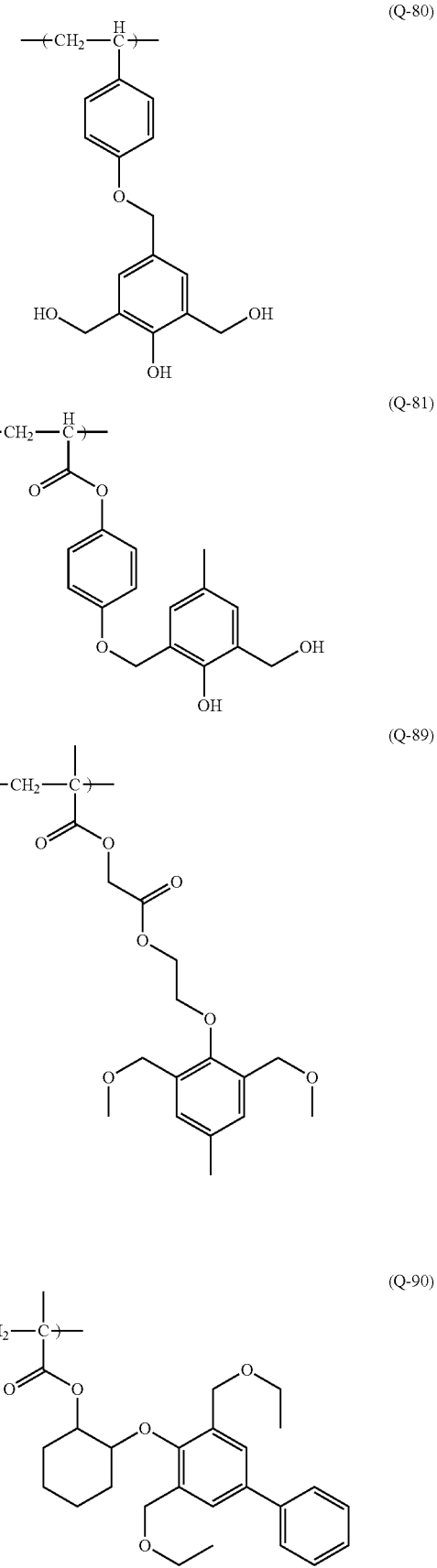

(Q-91)
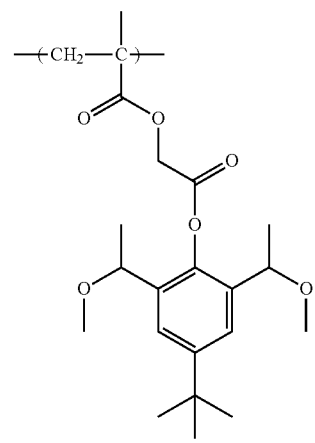
(Q-95)
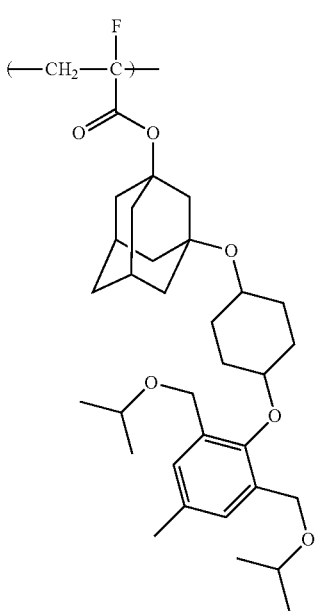
(Q-92)
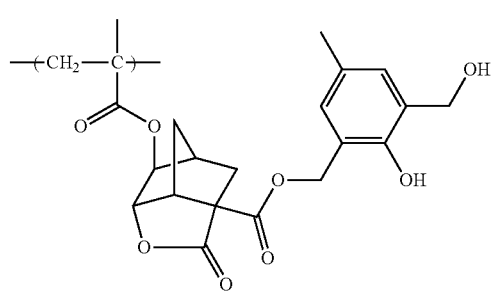
(Q-96)
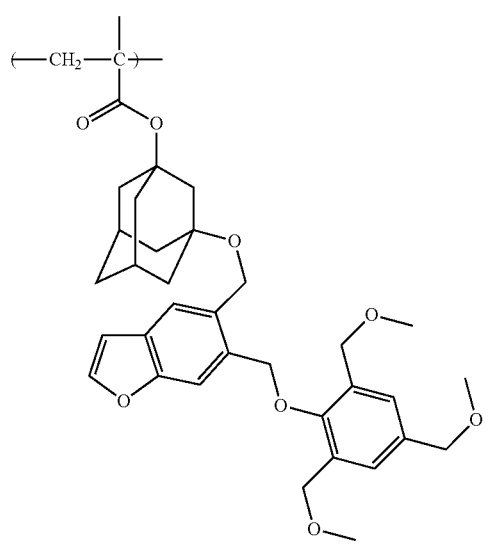
(Q-93)
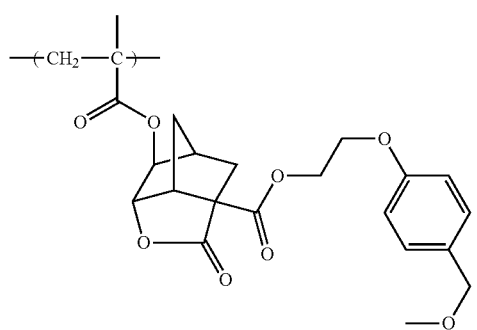
(Q-94)
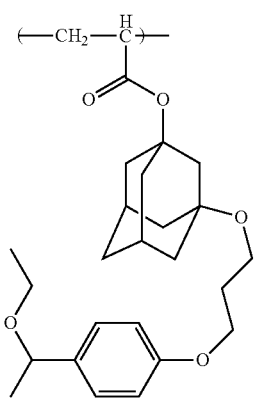
(Q-97)
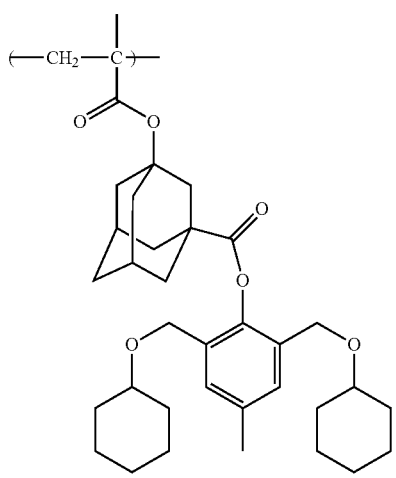

(Q-98) 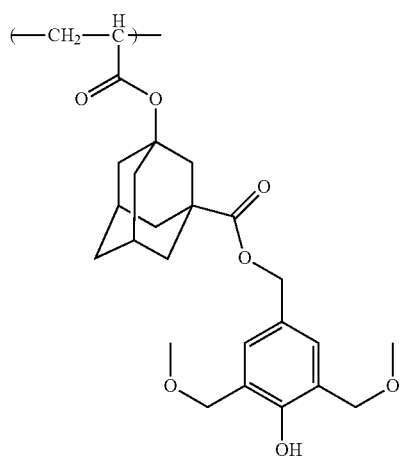
(Q-99) 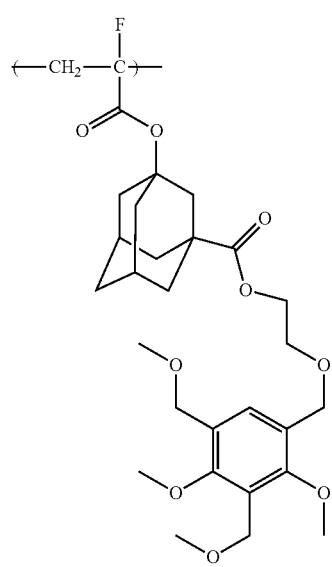
(Q-100) 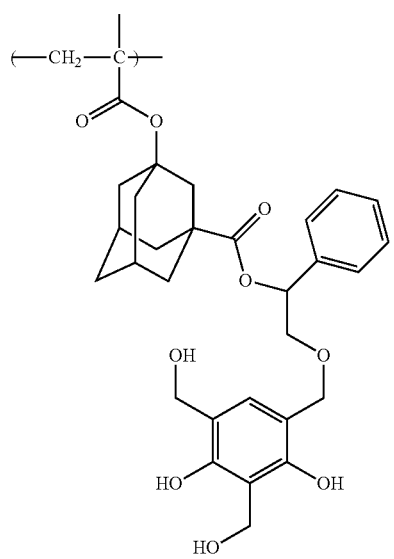
(Q-101) 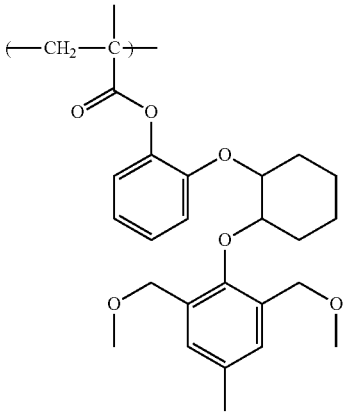
(Q-102) 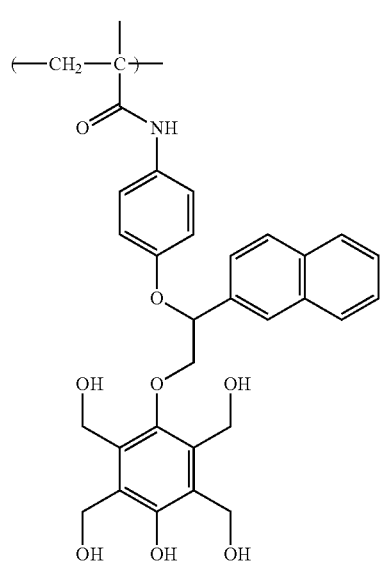
(Q-103) 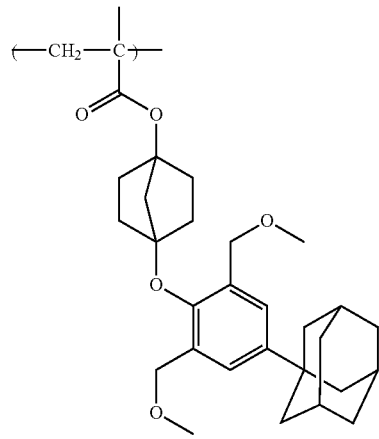

(Q-104)
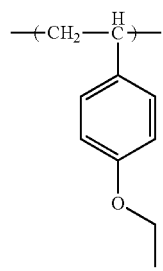
(Q-105)
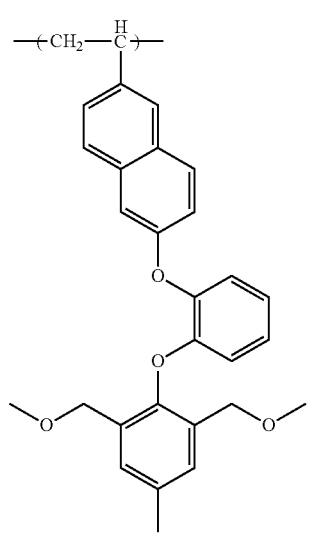
(A-106)
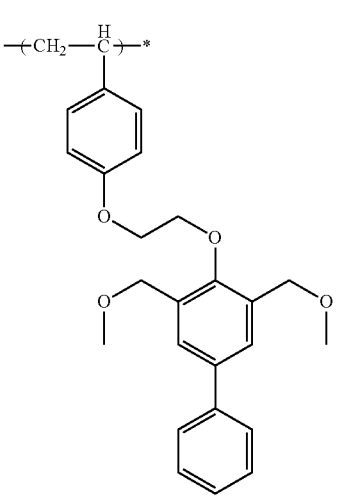
(A-107)
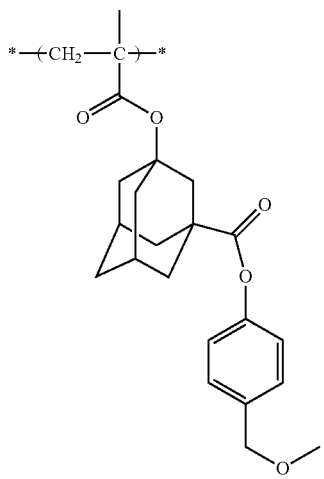
(A-108)
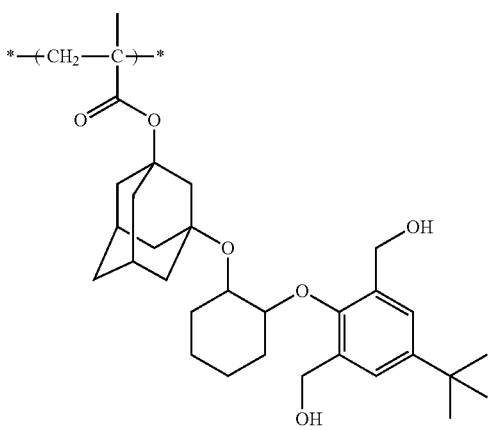
(A-109)
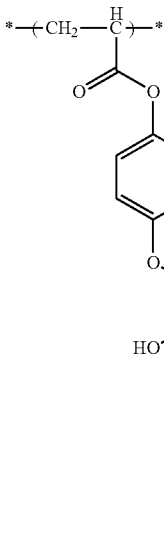

-continued

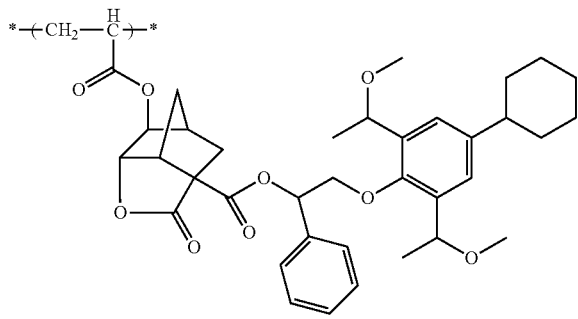
(A-110)

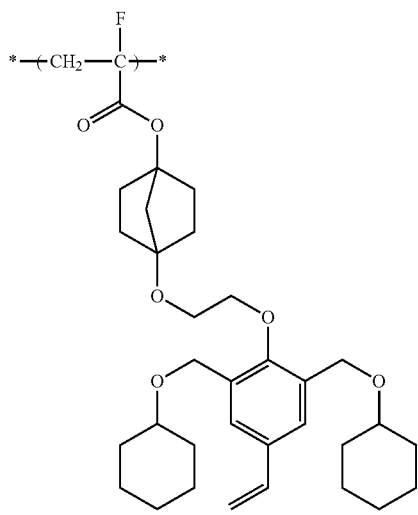
(A-111)

<Basic Compound>

The composition of the present invention preferably contains a basic compound, in addition to the components described above, as an acid scavenger. By using the basic compound, the change of performance with aging from exposure to post bake may be reduced. The basic compound is preferably an organic basic compound, and more specific examples thereof include aliphatic amines, aromatic amines, heterocyclic amines, a nitrogen-containing compound having a carboxyl group, a nitrogen-containing compound having a sulfonyl group, a nitrogen-containing compound having a hydroxyl group, a nitrogen-containing compound having a hydroxyphenyl group, an alcoholic nitrogen-containing compound, amido derivatives, and imide derivatives. An amine oxide compound (described in JP2008-102383A) and an ammonium salt (preferably a hydroxide or a carboxylate; more specifically, a tetraalkylammonium hydroxide typified by tetrabutylammonium hydroxide is preferred in view of LER) may also be appropriately used.

Furthermore, a compound whose basicity is increased by the action of an acid may also be used as a kind of the basic compound.

Specific examples of the amines may include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, didecylamine, methyloctadecylamine, dimethylundecylamine, N,N-dimethyldodecylamine, methyldioctadecylamine, N,N-dibutylaniline, N,N-dihexylaniline, 2,6-diisopropylaniline, 2,4,6-tri(t-butyl)aniline, triethanolamine, N,N-dihydroxyethylaniline, tris(methoxyethoxyethyl)amine, the compounds exemplified in column 3, line 60 et seq. of U.S. Pat. No. 6,040,112A, 2-[2-{2-(2,2-dimethoxy-phenoxyethoxy)ethyl}-bis-(2-methoxyethyl)]-amine, and compounds (C1-1) to (C3-3) exemplified in paragraph "0066" of US2007/0224539A1. Examples of the compound having a nitrogen-containing heterocyclic structure may include 2-phenylbenzimidazole, 2,4,5-triphenylimidazole, N-hydroxyethylpiperidine, bis(1,2,2,6,6-pentamethyl-4-piperidyl) sebacate, 4-dimethylaminopyridine, antipyrine, hydroxyantipyrine, 1,5-diazabicyclo[4.3.0]nona-5-ene, 1,8-diazabicyclo[5.4.0]-undeca-7-ene, and tetrabutylammonium hydroxide.

In addition, a photodecomposable basic compound (a compound which initially exhibits basicity due to the action of the basic nitrogen atom as a base but decomposes upon irradiation with actinic rays or radiation to generate a zwitterionic compound having a basic nitrogen atom and an organic acid moiety and resulting from neutralization thereof in the molecule, is reduced in or deprived of the basicity; for example, onium salts described in JP3577743B, JP2001-215689A, JP2001-166476A, and JP2008-102383A), and a photobase generator (for example, compounds described in JP2010-243773A) may also be appropriately used.

Among these basic compounds, an ammonium salt is preferred in view of improving resolution.

The content of the basic compound in the present invention is preferably 0.01 mass % to 10 mass %, more preferably 0.03 mass % to 5 mass %, and particularly preferably 0.05 mass % to 3 mass %, based on the total solid content of the composition.

In one embodiment of the present invention, the basic compound is more preferably an onium salt compound containing a nitrogen atom in a cation moiety which will be described below (hereinafter, referred to also as "compound (D)").

Examples of the onium salt compound include a diazonium salt compound, a phosphonium salt compound, a sulfonium salt compound, and an iodonium salt compound. Of these, a sulfonium salt compound or an iodonium salt compound is preferred, and a sulfonium salt compound is more preferred.

The onium salt compound typically includes a basic moiety containing a nitrogen atom in a cation moiety. Herein, the "basic moiety" refers to the portion of the cation moiety of the compound (D) whose conjugate acid exhibits a pKa value of −3 or higher. This pKa value is preferably in the range of −3 to 15, and more preferably in the range of 0 to 15. The pKa value refers to a value calculated by ACD/ChemSketch (ACD/Labs 8.00 Release Product Version: 8.08).

This basic moiety includes a structure selected from the group consisting of, for example, an amino group (a group resulting from the removal of one hydrogen atom from ammonia, a primary amine, or a secondary amine; same hereinafter) and a nitrogen-containing heterocyclic group. The amino group is preferably an aliphatic amino group. As used herein, the term "aliphatic amino group" means a group formed by removing one hydrogen atom from an aliphatic amine.

In the structure thereof, it is preferred for all the atoms adjacent to the nitrogen atom contained in the structure to be carbon or hydrogen atoms from the viewpoint of increasing basicity. Also, from the viewpoint of basicity increase, it is preferred that no electron withdrawing functional group (a carbonyl group, a sulfonyl group, a cyano group, a halogen atom, and the like) is directly bonded to the nitrogen atom.

The onium salt compound may include two or more basic moieties.

In the case where the cation moiety of the compound (D) contains an amino group, the cation moiety is preferably include a partial structure represented by the following General Formula (N-I).

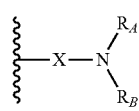

(N-I)

In the formula, each of $R_A$ and $R_B$ independently represents a hydrogen atom or an organic group.

X represents a single bond or a linking group.

At least two of $R_A$, $R_B$, and X may be bonded to each other to form a ring.

Examples of the organic group represented by $R_A$ or $R_B$ may include an alkyl group, a cycloalkyl group, an alkenyl group, an aryl group, a heterocyclic hydrocarbon group, an alkoxycarbonyl group, a lactone group, and a sultone group.

These groups may have a substituent, and examples of the substituent include an alkyl group, a cycloalkyl group, an alkoxy group, an alkoxycarbonyl group, a carboxyl group, a halogen atom, a hydroxyl group, and a cyano group.

The alkyl group represented by $R_A$ or $R_B$ may be linear or branched. The number of carbon atoms of the alkyl group is preferably 1 to 50, more preferably 1 to 30, and still more preferably 1 to 20. Examples of such an alkyl group may include a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group, and a 2-ethylhexyl group.

The cycloalkyl group represented by $R_A$ or $R_B$ may be monocyclic or polycyclic. The cycloalkyl group is preferably, for example, a monocyclic cycloalkyl group having 3 to 8 carbon atoms, such as a cyclopropyl group, a cyclopentyl group, or a cyclohexyl group.

The alkenyl group represented by $R_A$ or $R_B$ may be linear or branched. The number of carbon atoms of the alkenyl group is preferably 2 to 50, more preferably 2 to 30, and more preferably 3 to 20. Examples of such an alkenyl group include a vinyl group, an allyl group, and a styryl group.

The aryl group represented by $R_A$ or $R_B$ is preferably an aryl group having 6 to 14 carbon atoms. Examples of the aryl group include a phenyl group and a naphthyl group.

The heterocyclic hydrocarbon group represented by $R_A$ or $R_B$ is preferably a heterocyclic hydrocarbon group having 5 to 20 carbon atoms, and more preferably a heterocyclic hydrocarbon group having 6 to 15 carbon atoms. The heterocyclic hydrocarbon group may have aromaticity or may not have aromaticity. The heterocyclic hydrocarbon group preferably has aromaticity.

The heterocycle included in the above groups may be monocyclic or polycyclic. Examples of such a heterocycle may include an imidazole ring, a pyridine ring, a pyrazine ring, a pyrimidine ring, a pyridazine ring, a 2H-pyrrole ring, a 3H-indole ring, a 1H-indazole ring, a purine ring, an isoquinoline ring, a 4H-quinolizine ring, a quinoline ring, a phthalazine ring, a naphthyridine ring, quinoxaline ring, a quinazoline ring, a cinnoline ring, a pteridine ring, a phenanthridine ring, an acridine ring, a phenanthroline ring, a phenazine ring, a perimidine ring, a triazine ring, a benziso-quinoline ring, a thiazole ring, a thiadiazine ring, an azepine ring, an azocine ring, an isothiazole ring, an isoxazole ring or a benzothiazole ring.

The lactone group represented by $R_A$ or $R_B$ is, for example, a 5- to 7-membered ring lactone group, and may also be one in which a bicycle structure and a spiro structure are formed in a 5- to 7-membered ring lactone group and another cyclic structure is condensed thereto.

The sultone groups represented by $R_A$ or $R_B$ is, for example, a 5- to 7-membered ring sultone group, and may also be one in which a bicycle structure and a spiro structure are formed in a 5- to 7-membered ring sultone group and another cyclic structure is condensed thereto.

Specifically, preferred is a group having the structure shown below.

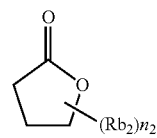

LC1-1

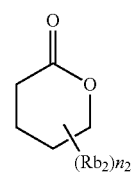

LC1-2

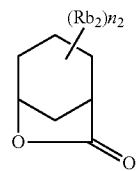

LC1-3

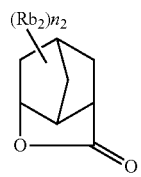

LC1-4

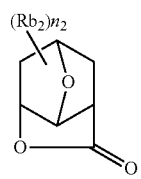

LC1-5

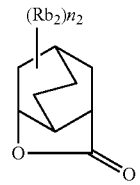

LC1-6

-continued

LC1-7 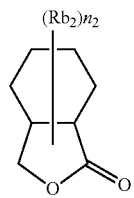

LC1-8 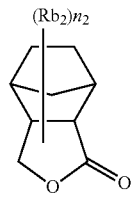

LC1-9 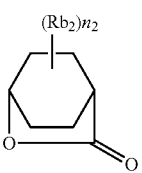

LC1-10 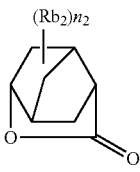

LC1-11 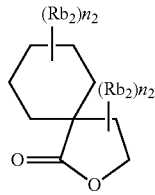

LC1-12 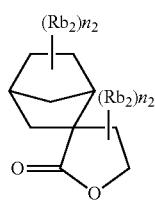

LC1-13 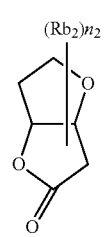

LC1-14 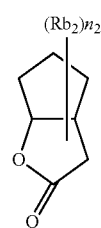

-continued

LC1-15 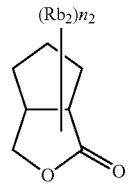

LC1-16 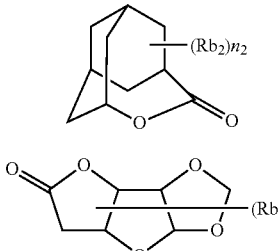

LC1-17 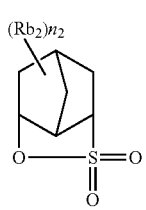

SL1-1 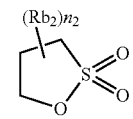

SL1-2

SL1-3 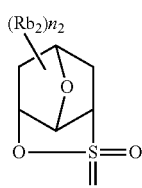

The lactone group and the sultone group may have or may not have a substituent ($Rb_2$). Preferred examples of the substituent ($Rb_2$) include the same substituents as those listed for the substituent of $R_A$ and $R_B$ above. When $n_2$ is 2 or more, plural substituents ($Rb_2$'s) may be the same or different. Also, plural substituents ($Rb_2$'s) may be bonded to each other to form a ring.

Examples of the linking group represented by X include a linear or branched alkylene group, a cycloalkylene group, an ether bond, an ester bond, an amido bond, a urethane bond, a urea bond, and a group formed by combining two or more of these groups. X more preferably represents a single bond, an alkylene group, a group formed by combining an alkylene group and an ether bond, or a group formed by combining an alkylene group and an ester bond. The number of atoms of the linking group represented by X is preferably 20 or less, and more preferably 15 or less. The linear or branched alkylene group and cycloalkylene group preferably contain 8 or less carbon atoms, and may have a substituent. The substituent preferably contains 8 or less carbon atoms, and example thereof include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms).

At least two of $R_A$, $R_B$, and X may be bonded to each other to form a ring. The number of carbon atoms forming the ring is preferably 4 to 20. The ring may be monocyclic or polycyclic, and may contain an oxygen atom, a sulfur atom, a nitrogen atom, an ester bond, an amido bond, or a carbonyl group in the ring.

When the cation moiety of the compound (D) contains a nitrogen-containing heterocyclic group, the nitrogen-containing heterocyclic group may have aromaticity or may not have aromaticity. Moreover, the nitrogen-containing heterocyclic group may be monocyclic or polycyclic. The nitrogen-containing heterocyclic group is preferably, for example, a group containing a piperidine ring, a morpholine ring, a pyridine ring, an imidazole ring, a pyrazine ring, pyrrole ring, or a pyrimidine ring.

The onium salt compound (D) is preferably a compound represented by the following General Formula (N-II).

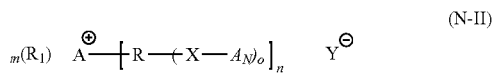

(N-II)

In the formula,

A represents a sulfur atom or an iodine atom.

$R_1$ represents a hydrogen atom or an organic group, and in the case where a plurality of $R_1$'s are present, $R_1$'s may be the same or different.

R represents a (o+1)-valent organic group, and in the case where a plurality of R's are present, R's may be the same or different.

X represents a single bond or a linking group, and in the case where a plurality of X's are present, X's may be the same or different.

$A_N$ represents a basic moiety containing a nitrogen atom, and in the case where a plurality of $A_N$'s are present, $A_N$'s may be the same or different.

In the case where A is a sulfur atom, n is an integer of 1 to 3, and m is an integer satisfying a relathionship of m+n=3.

In the case where A is an iodine atom, n is 1 or 2, and m is an integer satisfying a relationship of m+n=2.

o represents an integer of 1 to 10.

$Y^-$ represents an anion (details are as described below as the anion moiety of the compound (D1)).

At least two of $R_1$, X, R, and $A_N$ may be bonded to each other to form a ring.

The (o+1)-valent organic group represented by R may be, for example, a chain-like (linear or branched) or cyclic aliphatic hydrocarbon group, a heterocyclic hydrocarbon group, and aromatic hydrocarbon group, and preferably an aromatic hydrocarbon group. In the case where R is an aromatic hydrocarbon group, it is preferred to be bonded at the para-position (1,4-position) of an aromatic hydrocarbon group.

The linking group represented by X has the same definition as the linking group represented by X in General Formula (N-I), and may include the same specific examples.

The basic moiety represented by $A_N$ has the same definition as the "basic moiety" in the cation moiety of the compound (D) and may contain, for example, an amino group or a nitrogen-containing heterocyclic group. In the case where a basic moiety includes an amino group, the amino group may be, for example, a —N($R_A$)($R_B$) group in General Formula (N-I).

Examples of the organic group represented by $R_1$ may include an alkyl group, an alkenyl group, an alicyclic group, an aromatic hydrocarbon group, or a heterocyclic hydrocarbon group. In the case of m=2, two $R_1$'s may be bonded to each other to form a ring. These groups or rings may further have a substituent.

The alkyl group represented by $R_1$ may be linear or branched. The number of carbon atoms of the alkyl group is preferably 1 to 50, more preferably 1 to 30, and still more preferably 1 to 20. Examples of such an alkyl group may include a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group, and a 2-ethylhexyl group.

The alkenyl group represented by $R_1$ may be linear or branched. The number of carbon atoms of the alkenyl group is preferably 2 to 50, more preferably 2 to 30, and still more preferably 3 to 20. Examples of the alkenyl group may include a vinyl group, an allyl group, and a styryl group.

The alicyclic group represented by $R_1$ is, for example, a cycloalkyl group. The cycloalkyl group may be monocyclic or polycyclic. This alicyclic group is preferably a monocyclic cycloalkyl group having 3 to 8 carbon atoms, such as a cyclopropyl group, a cyclopentyl group, or a cyclohexyl group.

The aromatic hydrocarbon group represented by $R_1$ preferably has 6 to 14 carbon atoms. Examples of such a group may include an aryl group, such as a phenyl group or a naphthyl group. The aromatic hydrocarbon group represented by $R_1$ is preferably a phenyl group.

The heterocyclic hydrocarbon group represented by $R_1$ may have aromaticity or may not have aromaticity. The heterocyclic hydrocarbon group preferably has aromaticity.

The heterocycle included in the above groups may be monocyclic or polycyclic. Examples of such a heterocycle may include an imidazole ring, a pyridine ring, a pyrazine ring, a pyrimidine ring, a pyridazine ring, a 2H-pyrrole ring, a 3H-indole ring, a 1H-indazole ring, a purine ring, an isoquinoline ring, a 4H-quinolizine ring, a quinoline ring, a phthalazine ring, a naphthyridine ring, quinoxaline ring, a quinazoline ring, a cinnoline ring, a pteridine ring, a phenanthridine ring, an acridine ring, a phenanthroline ring, a phenazine ring, a perimidine ring, a triazine ring, a benzisoquinoline ring, a thiazole ring, a thiadiazine ring, an azepine ring, an azocine ring, an isothiazole ring, an isoxazole ring, and a benzothiazole ring.

Preferably, $R_1$ is an aromatic hydrocarbon group, or two $R_1$'s are bonded to each other to form a ring.

The ring which may be formed by bonding of at least two of $R_1$, X, R, or $A_N$ with each other is preferably a 4- to 7-membered ring, more preferably a 5- or 6-membered ring, and particularly preferably a 5-membered ring. Moreover, the ring skeleton may contain a heteroatom such as an oxygen atom, a sulfur atom, or a nitrogen atom.

In the case where the group represented by $R_1$ or the ring formed by bonding of two $R_1$'s to each other further includes a substituent, examples of the substituent may include the following substituents. That is, examples of the substituent may include a halogen atom (—F, —Br, —Cl, or —I), a hydroxyl group, an alkoxy group, an aryloxy group, a mercapto group, an alkylthio group, an arylthio group, an amino group, an acyloxy group, a carbamoyloxy group, an alkylsulfoxy group, an arylsulfoxy group, an acylthio group, an acylamino group, a ureido group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group, an N-aryl-N-aryloxycarbonylamino group, a formyl group, an acyl group, a carboxyl group, a carbamoyl group, an alkylsulfinyl group, an arylsulfinyl group, an alkylsulfonyl group, an arylsulfonyl group, a sulfo group (—$SO_3H$) or its conjugate base group (referred to as a sulfonato group), an alkoxysulfonyl group, an aryloxysulfonyl group, a sulfinamoyl group, a phosphono group (—PO₃H₂) or its conjugate base group (referred to as a phosphonato group), a phosphonooxy group (—OPO₃H₂) or its conjugate base group (referred to as a phosphonatooxy group), a cyano group, a nitro group, an aryl group, an alkenyl group, an alkynyl group, a heterocyclic group, a silyl group, and an alkyl group.

Among these substituents, preferred are a hydroxyl group, an alkoxy group, a cyano group, an aryl group, an alkenyl group, an alkynyl group, an alkyl group, and the like.

In General Formula (N-II), o is preferably an integer of 1 to 4, more preferably 1 or 2, and still more preferably 1.

The compound (D) represented by General Formula (N-II), in one embodiment, is preferably a compound in which at least one R of the n number of R's in the formula is an aromatic hydrocarbon group and in which the X of at least one of the o number of —(X-A$_N$) groups bonding to at least one of the aromatic hydrocarbon groups is a linking group in which the binding site to the aromatic hydrocarbon group is a carbon atom.

Namely, in this compound (D) in this embodiment, the basic moiety represented by A$_N$ is bonded via the carbon atom directly to the aromatic hydrocarbon group represented by R to the aromatic hydrocarbon group.

The aromatic hydrocarbon group represented by R may contain a heterocycle as the aromatic ring in the aromatic hydrocarbon group. Further, the aromatic ring may be monocyclic or polycyclic.

This aromatic ring group preferably contains 6 to 14 carbon atoms. Examples of such a group may include an aryl group, such as a phenyl group, a naphthyl group, or an anthryl group. In the case where the aromatic ring group contains a heterocycle, examples of the heterocycle may include a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, or a thiazole ring.

The aromatic hydrocarbon group represented by R is preferably a phenyl group or a naphthyl group, and particularly preferably a phenyl group.

The aromatic hydrocarbon group represented by R may further include a substituent in addition to the groups of —(X-A$_N$) to be described hereinafter. As the substituent, use can be made of, for example, any of those set forth above in connection with R$_1$.

Further, in this embodiment, the linking group represented by X appearing in at least one —(X-A$_N$) group as a substituent of the aromatic ring R is not particularly limited as long as the portion of bonding to the aromatic hydrocarbon group represented by R is a carbon atom. The linking group includes, for example, an alkylene group, a cycloalkylene group, an arylene group, —COO—, —CO—, or a combination thereof. The linking group may include a combination of any of these groups with at least one member selected from the group consisting of —O—, —S—, —OCO—, —S(=O)—, —S(=O)₂—, —OS(=O)₂—, and —NR'—, in which R' represents, for example, a hydrogen atom, an alkyl group, a cycloalkyl group, or an aryl group.

The alkylene group containable in the linking group represented by X may be linear or branched. The alkylene group preferably contains 1 to 20 carbon atoms, and more preferably 1 to 10 carbon atoms. Examples of such an alkylene group may include a methylene group, an ethylene group, a propylene group, and a butylene group.

The cycloalkylene group containable in the linking group represented by X may be monocyclic or polycyclic. The cycloalkylene group preferably contains 3 to 20 carbon atoms, and more preferably 3 to 10 carbon atoms. The cycloalkylene group may be, for example, a 1,4-cyclohexylene group.

The arylene group containable in the linking group represented by X preferably contains 6 to 20 carbon atoms, and more preferably 6 to 10 carbon atoms. Examples of such an arylene group may include a phenylene group or a naphthylene group.

At least one of X's is preferably represented by the following General Formula (N-III) or (N-IV).

(N-III)

In the formula,

R$_2$ and R$_3$ represent a hydrogen atom, an alkyl group, an alkenyl group, an alicyclic group, an aromatic hydrocarbon group, or a heterocyclic hydrocarbon group. R$_2$ and R$_3$ may be bonded to each other to form a ring. At least one of R$_2$ or R$_3$ may be bonded to E to form a ring.

E represents a linking group or a single bond.

(N-IV)

In the formula,

J represents an oxygen atom or a sulfur atom.

E represents a linking group or a single bond.

Examples of the respective groups represented by R$_2$ and R$_3$ and substituents that may be further introduced in these groups are the same as those mentioned above in connection with R$_1$. Each of the ring which can be formed by bonding of R$_2$ and R$_3$ and the ring which can be formed by bonding of at least one of R$_2$ or R$_3$ to E is preferably a 4- to 7-membered ring, and more preferably a 5- or 6-membered ring. Preferably, each of R$_2$ and R$_3$ is independently a hydrogen atom or an alkyl group.

The linking group represented by E includes, for example, an alkylene group, a cycloalkylene group, an arylene group, —COO—, —CO—, —O—, —S—, —OCO—, —S(=O)—, —S(=O)₂—, —OS(=O)₂—, —NR—, or a combination thereof. In —NR—, R represents, for example, a hydrogen atom, an alkyl group, a cycloalkyl group, or an aryl group.

The linking group represented by E is at least one member selected from the group consisting of an alkylene bond, an ester bond, an ether bond, a thioether bond, a urethane bond (a group represented by

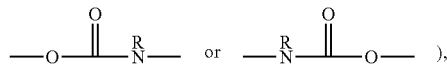

a urea bond
(a group represented by

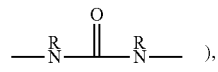

an amido bond and a sulfonamido bond. The linking group represented by E is more preferably an alkylene bond, an ester bond, or an ether bond.

Further, the compound (D) may be a compound having a plurality of moieties each containing a nitrogen atom. For example, the compound (D) may be a compound having the structure of General Formula (N-II) in which at least one $R_1$ is represented by General Formula (N-I).

The compound (D) of General Formula (N-II), in one embodiment thereof, is represented by the following General Formula (N-V).

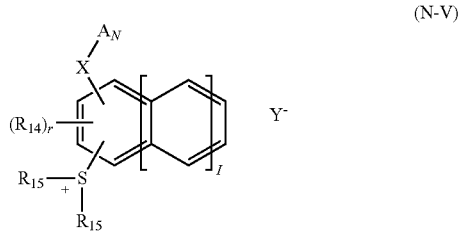

In the formula, X, $A_N$, and $Y^-$ have the same definitions as the groups in General Formula (N-II), respectively, and specific examples and preferred examples thereof are also the same.

$R_{14}$, $R_{15}$, r, and l have the same definitions as the groups and indices in General Formula (ZI-4) that represents one embodiment of a later-described photoacid generator (B), respectively, and specific examples and preferred examples thereof are also the same.

Further, the compound (D) represented by General Formula (N-II), in one embodiment, is represented by the following General Formula (N-VI).

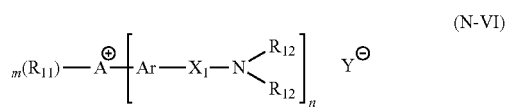

In General Formula (N-VI),

A represents a sulfur atom or an iodine atom.

Each $R_{11}$ independently represents an alkyl group, an alkenyl group, an alicyclic group, an aromatic hydrocarbon group, or a heterocyclic hydrocarbon group. In the case of m=2, two $R_{11}$'s may be bonded to each other to form a ring.

Each Ar independently represents an aromatic hydrocarbon group.

Each $X_1$ independently represents a divalent linking group.

Each $R_{12}$ independently represents a hydrogen atom or an organic group.

In the case where the A is a sulfur atom, m is an integer of 1 to 3, and n is an integer satisfying the relationship of m+n=3.

In the case where the A is an iodine atom, m is an integer of 1 or 2, and n is an integer satisfying the relationship of m+n=2.

$Y^-$ represents an anion (details are as described below as the anion moiety of the compound (D)).

Specific examples and preferred examples of the alkyl group, alkenyl group, alicyclic group, aromatic hydrocarbon group, and heterocyclic hydrocarbon group as $R_{11}$ are the same as specific examples and preferred examples of the alkyl group, alkenyl group, alicyclic group, aromatic hydrocarbon group, and heterocyclic hydrocarbon group as $R_1$ in General Formula (N-II).

Specific examples and preferred examples of the aromatic hydrocarbon group as Ar are the same as the specific examples and preferred examples of the aromatic hydrocarbon group as R in General Formula (N-II).

Specific examples and preferred examples of the divalent linking group as $X_1$ are the same as the specific examples and preferred examples of the linking group as X in General Formula (N-II).

Specific examples and preferred examples of the organic group as $R_{12}$ are the same as the specific examples and preferred examples of the organic group as $R_A$ and $R_B$ in General Formula (N-I).

An embodiment where X is an alkylene group (for example, a methylene group), and two $R_{12}$'s are bonded to each other to form a ring is particularly preferred from the viewpoints of post exposure bake (PEB) temperature dependency and post exposure line width (PED) stability.

The anion moiety of the compound (D) is not particularly limited. The anion contained in the compound (D) is preferably a non-nucleophilic anion. Here, the non-nucleophilic anion is an anion having an extremely low ability of causing a nucleophilic reaction and capable of suppressing the decomposition with aging due to the intramolecular nucleophilic reaction. Thus, aging stability of the composition according to the present invention is improved.

Examples of the non-nucleophilic anion may include a sulfonate anion, a carboxylate anion, a sulfonylimide anion, a bis(alkylsulfonyl)imide anion, and a tris(alkylsulfonyl)methide anion.

Examples of the sulfonate anion may include an aliphatic sulfonate anion, an aromatic sulfonate anion, and a camphorsulfonate anion.

Examples of the carboxylate anion may include an aliphatic carboxylate anion, an aromatic carboxylate anion, and an aralkylcarboxylate anion.

The aliphatic moiety in the aliphatic sulfonate anion may be an alkyl group or an cycloalkyl group, and is preferably an alkyl group having 1 to 30 carbon atoms and a cycloalkyl group having 3 to 30 carbon atoms, such as a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, and a bornyl group.

The aromatic group in the aromatic sulfonate anion is preferably an aryl group having 6 to 14 carbon atoms, and examples thereof may include a phenyl group, a tolyl group, and a naphthyl group.

The alkyl group, cycloalkyl group, and aryl group in the aliphatic sulfonate anion and aromatic sulfonate anion may have a substituent. Examples of the substituent for the alkyl group, cycloalkyl group, and aryl group in the aliphatic sulfonate anion and aromatic sulfonate anion may include a nitro group, a halogen atom (a fluorine atom, a chlorine atom, a bromine atom, an iodine atom), a carboxy group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), and a cycloalkylalkyloxyalkyloxy group (preferably having 8 to 20 carbon atoms). For the aryl group and ring structure in each group, an alkyl group (preferably having 1 to 15 carbon atoms) as a substituent may be further exemplified.

Examples of the aliphatic moiety in the aliphatic carboxylate anion may include the same alkyl group and cycloalkyl group as in the aliphatic sulfonate anion.

Examples of the aromatic group in the aromatic carboxylate anion are the same aryl group as in the aromatic sulfonate anion.

The aralkyl group in the aralkylcarboxylate anion is preferably an aralkyl group having 6 to 12 carbon atoms, and examples thereof may include a benzyl group, a phenethyl group, a naphthylmethyl group, a naphthylethyl group, and a naphthylbutyl group.

The alkyl group, cycloalkyl group, aryl group, and aralkyl group in the aliphatic carboxylate anion, aromatic carboxylate anion, and aralkyl carboxylate anion may have a substituent. Examples of the substituent for the alkyl group, cycloalkyl group, aryl group, and aralkyl group in the aliphatic carboxylate anion, aromatic carboxylate anion, and aralkyl carboxylate anion may include the same halogen atom, alkyl group, cycloalkyl group, alkoxy group, and alkylthio group as in the aromatic sulfonate anion.

The sulfonylimide anion may be, for example, a saccharin anion.

The alkyl group in the bis(alkylsulfonyl)imide anion and tris(alkylsulfonyl)methide anion is preferably an alkyl group having 1 to 5 carbon atoms, and examples thereof may include a methyl group, an ethyl group, a propyl group, an isopropyl group, an n-butyl group, an isobutyl group, a sec-butyl group, a pentyl group, and a neopentyl group. Examples of the substituent for these alkyl groups may include a halogen atom, an alkyl group substituted with a halogen atom, an alkoxy group, an alkylthio group, an alkyloxysulfonyl group, an aryloxysulfonyl group, and a cycloalkylaryloxysulfonyl group. Preferred is an alkyl group substituted with a fluorine atom. Moreover, also preferred is an embodiment in which two alkyl groups in the bis(alkylsulfonyl)imide anion are bonded to each other to form a cyclic structure. In this case, it is preferred that the ring structure formed is a 5- to 7-membered ring.

Examples of the other non-nucleophilic anion may include fluorinated phosphorus, fluorinated boron, and fluorinated antimony.

The non-nucleophilic anion is preferably an aliphatic sulfonate anion in which the α-position of sulfonic acid is substituted with a fluorine atom, an aromatic sulfonate anion substituted with a fluorine atom or a group having a fluorine atom, a bis(alkylsulfonyl)imide anion in which the alkyl group is substituted with a fluorine atom, or a tris(alkylsulfonyl)methide anion in which the alkyl group is substituted with a fluorine atom. The non-nucleophilic anion is more preferably a perfluoro aliphatic sulfonate anion having 4 to 8 carbon atoms, or a benzenesulfonate anion having a fluorine atom, and still more preferably a nonafluorobutanesulfonate anion, a perfluorooctanesulfonate anion, a pentafluorobenzenesulfonate anion, or a 3,5-bis(trifluoromethyl)benzenesulfonate anion.

Further, the non-nucleophilic anion is preferably, for example, represented by the following General Formula (LD1).

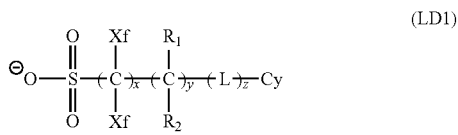

(LD1)

In the formula, each Xf independently represents a fluorine atom or an alkyl group substituted with at least one fluorine atom.

Each of $R_1$ and $R_2$ independently represents a hydrogen atom, a fluorine atom, or an alkyl group.

Each L independently represents a divalent linking group.

Cy represents a cyclic organic group.

x represents an integer of 1 to 20.

y represents an integer of 0 to 10.

z represents an integer of 0 to 10.

Xf is a fluorine atom or an alkyl group which is substituted with at least one fluorine atom. This alkyl group preferably has 1 to 10 carbon atoms, and more preferably 1 to 4. The alkyl group substituted with at least one fluorine atom is preferably a perfluoroalkyl group.

Xf is preferably a fluorine atom or a perfluoroalkyl group having 1 to 4 carbon atoms. More specifically, Xf is preferably a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, or $CH_2CH_2C_4F_9$.

Each of $R_1$ and $R_2$ is independently a hydrogen atom, a fluorine atom, or an alkyl group. The alkyl group may have a substituent (preferably a fluorine atom) and preferably has 1 to 4 carbon atoms. More preferred is a perfluoroalkyl group having 1 to 4 carbon atoms. Specific examples of the alkyl group having a substituent as $R_1$ and $R_2$ include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$. Among these, preferred is $CF_3$.

L represents a divalent linking group. Examples of the divalent linking group may include —COO—, —OCO—, —CONH—, —CO—, —O—, —S—, —SO—, —SO₂—, an alkylene group, a cycloalkylene group, and an alkenylene group. Among these, preferred is —CONH—, —CO—, or —SO₂— and more preferred is —CONH— or —SO₂—.

Cy represents a cyclic organic group. Examples of the cyclic organic group may include an alicyclic group, an aryl group, and a heterocyclic group.

The alicyclic group may be monocyclic or polycyclic. The monocyclic alicyclic group may be a monocyclic cycloalkyl group such as a cyclopentyl group, a cyclohexyl group, or a cyclooctyl group. The polycyclic alicyclic group may be a polycyclic cycloalkyl group such as a norbornyl group, a tricyclodecanyl group, a tetracyclodecanyl group, a tetracyclododecanyl group, or an adamantyl group. Among them, an alicyclic group with a bulky structure having 7 or more carbon atoms such as a norbornyl group, a tricyclodecanyl group, a tetracyclodecanyl group, a tetracyclododecanyl group, or an adamantyl group is preferred from the viewpoints of inhibiting diffusivity into the film during post exposure baking (PEB) process and improving a mask error enhancement factor (MEEF).

The aryl group may be monocyclic or polycyclic. Examples of the aryl group may include a phenyl group, a naphthyl group, a phenanthryl group, and an anthryl group. Among them, a naphthyl group showing a relatively low light absorbance at 193 nm is preferred.

The heterocyclic group may be monocyclic or polycyclic, but a polycyclic heterocyclic group may further inhibit diffusion of an acid. Also, the heterocyclic group may have aromaticity or may not have aromaticity. Examples of the heterocycle having aromaticity may include a furan ring, a thiophene ring, a benzofuran ring, a benzothiophene ring, a dibenzofuran ring, a dibenzothiophene ring, and a pyridine ring. Examples of the heterocycle having no aromaticity may include a tetrahydropyran ring, a lactone ring, and a decahydroisoquinoline ring. As the heterocycle in the heterocyclic group, a furan ring, a thiophene ring, a pyridine ring, or a decahydroisoquinoline ring is particularly preferred. Also, examples of the lactone ring may include lactone rings illustrated in connection with $R_A$ and $R_B$ in General Formula (N-I).

The cyclic organic group may have a substituent. Examples of the substituent may include an alkyl group, a cycloalkyl group, an aryl group, a hydroxy group, an alkoxy group, an ester group, an amido group, a urethane group, an ureido group, a thioether group, a sulfonamido group, and a sulfonic acid ester group. The alkyl group may be linear or branched. In addition, the alkyl group preferably contains 1 to 12 carbon atoms. The cycloalkyl group may be monocyclic or polycyclic. Also, the cycloalkyl group preferably contains 3 to 12 carbon atoms. The aryl group preferably contains 6 to 14 carbon atoms.

x is preferably 1 to 8, more preferably 1 to 4, and particularly preferably 1. y is preferably 0 to 4, and more preferably 0. z is preferably 0 to 8, and more preferably 0 to 4.

Further, the non-nucleophilic anion is also preferably represented, for example, by the following General Formula (LD2).

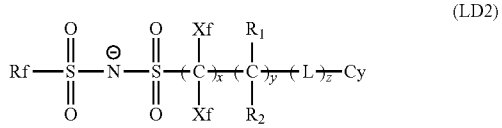

(LD2)

In General Formula (LD2), Xf, $R_1$, $R_2$, L, Cy, x, y, and z have the same definitions as those in General Formula (LD1), respectively. Rf is a group containing a fluorine atom.

Examples of the fluorine atom-containing group represented by Rf may include an alkyl group having at least one fluorine atom, a cycloalkyl group having at least one fluorine atom, and an aryl group having at least one fluorine atom.

These alkyl group, cycloalkyl group, and aryl group may be substituted by a fluorine atom or may be substituted by another fluorine atom-containing substituent. In the case where Rf is a cycloalkyl group having at least one fluorine atom or an aryl group having at least one fluorine atom, examples of the another fluorine-containing substituent include an alkyl group substituted with at least one fluorine atom.

Also, these alkyl group, cycloalkyl group, and aryl group may be further substituted by a fluorine atom-free substituent. Examples of this substituent include those not containing a fluorine atom out of those described above for Cy.

Examples of the alkyl group having at least one fluorine atom represented by Rf are the same as those described above as the alkyl group substituted with at least one fluorine atom represented by Xf. Examples of the cycloalkyl group having at least one fluorine atom represented by Rf include a perfluorocyclopentyl group and a perfluorocyclohexyl group. Examples of the aryl group having at least one fluorine atom represented by Rf include a perfluorophenyl group.

A preferred embodiment of the anion moiety of the compound (D) may be, for example, a structure illustrated as the preferred anion structure of the photoacid generator (B), in addition to the structures represented by General Formulae (LD1) and (LD2).

Further, the fluorine content of the compound (D), as expressed in terms of (total mass of all fluorine atoms in compound)/(total mass of all atoms in compound), is preferably 0.30 or less, more preferably 0.25 or less, still more preferably 0.20 or less, particularly preferably 0.15 or less, and most preferably 0.10 or less.

Hereinafter, specific examples of the compound (D) are shown, but are not limited thereto.

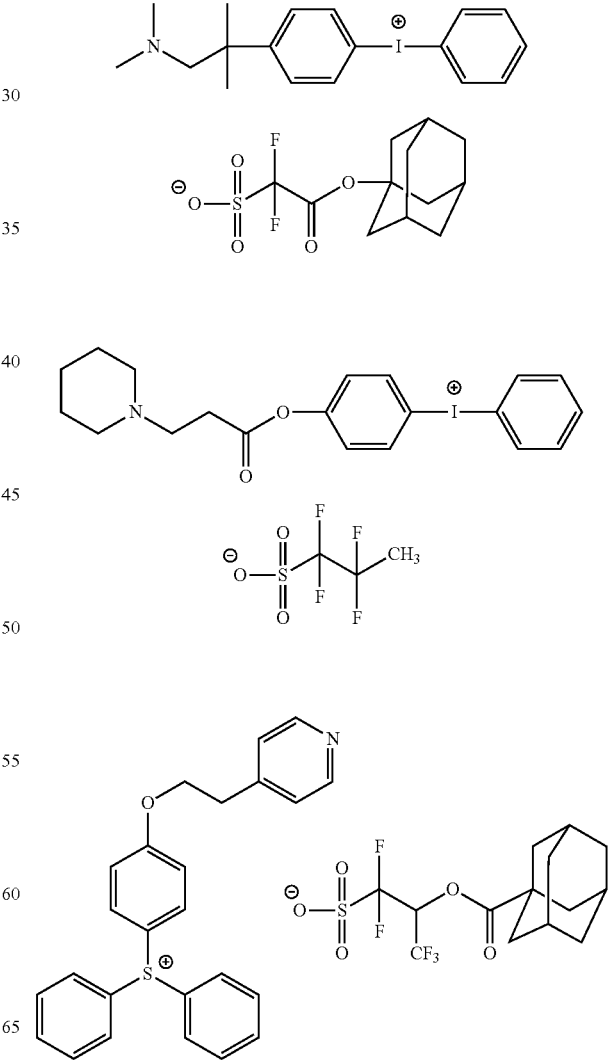

115
-continued
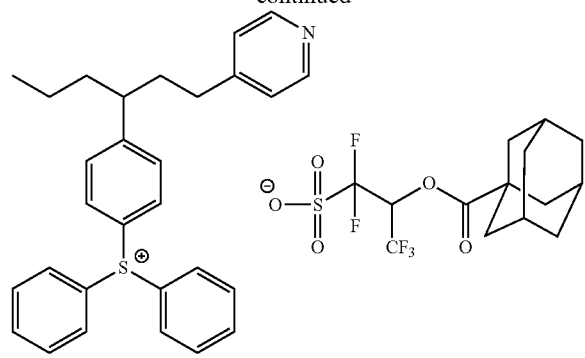
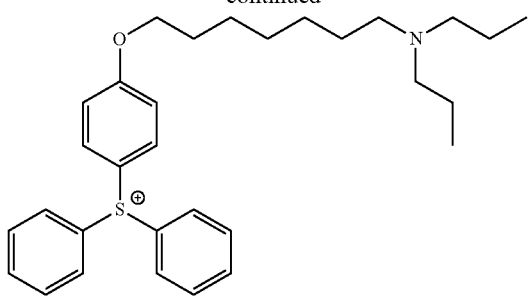
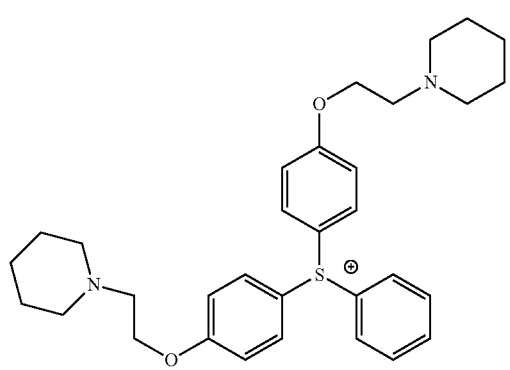
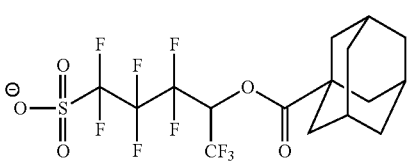
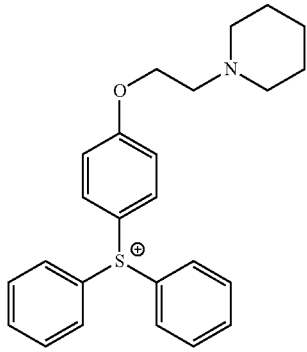
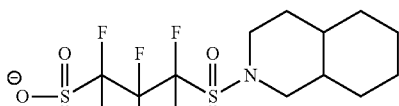
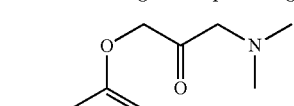
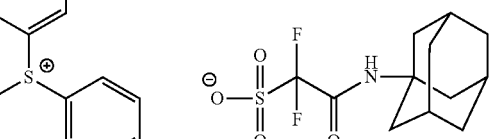
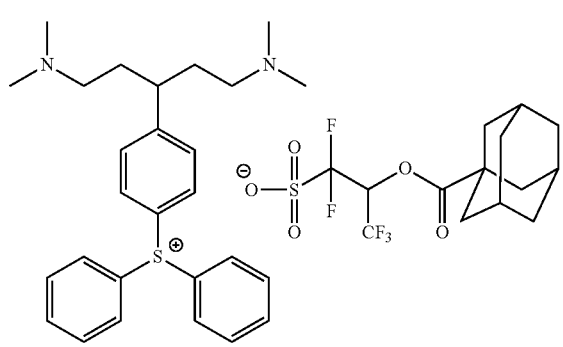
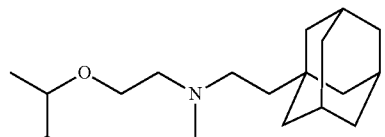
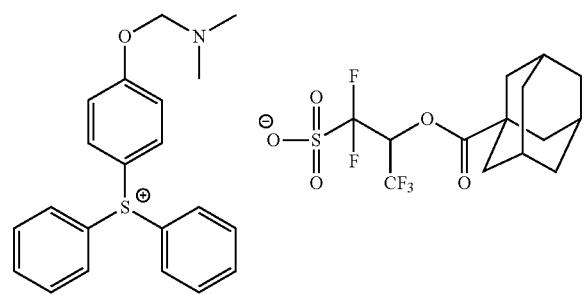
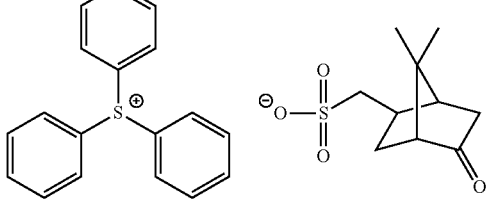
116
-continued

117 -continued
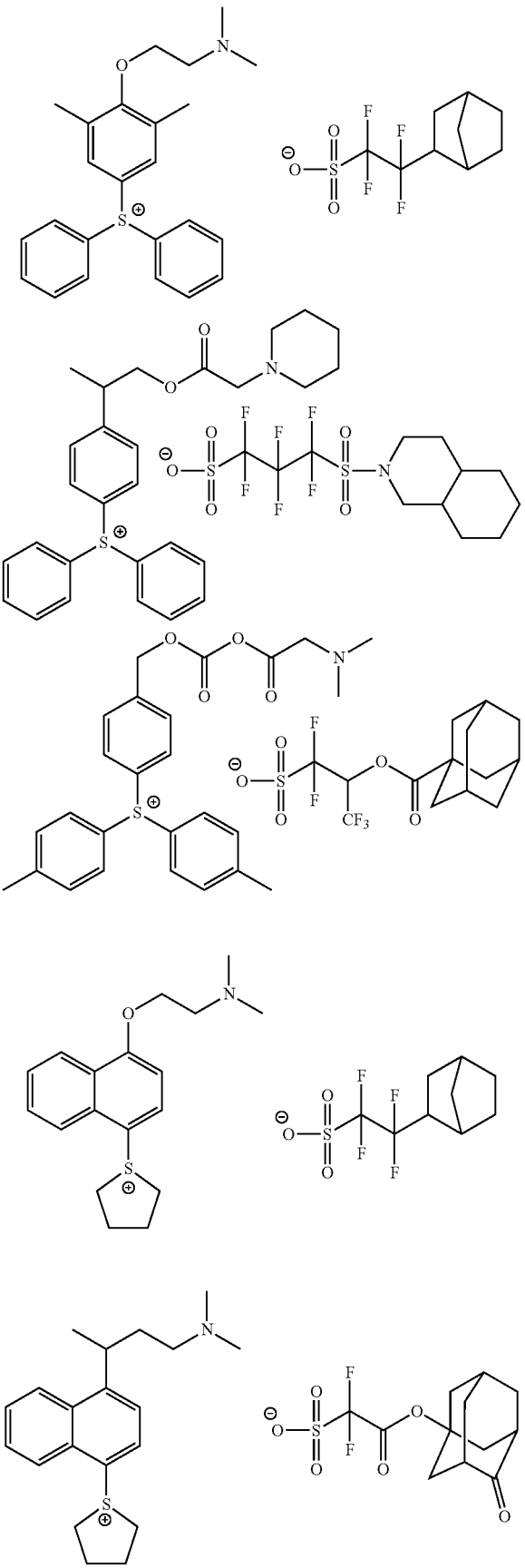
118 -continued
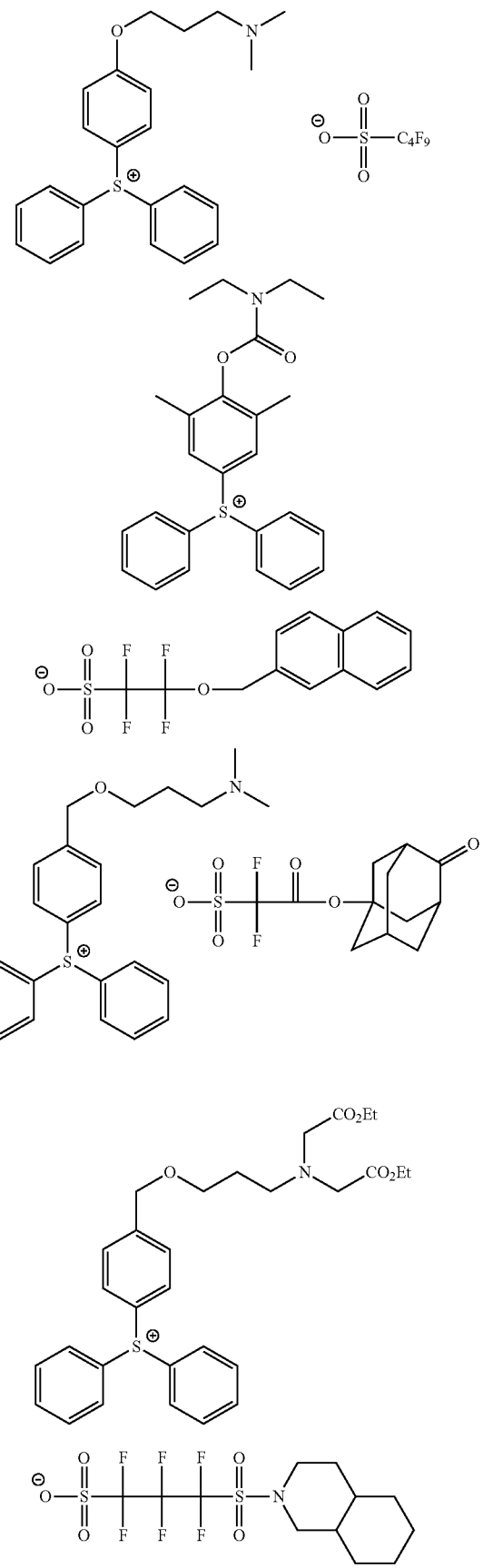

119
-continued
120
-continued
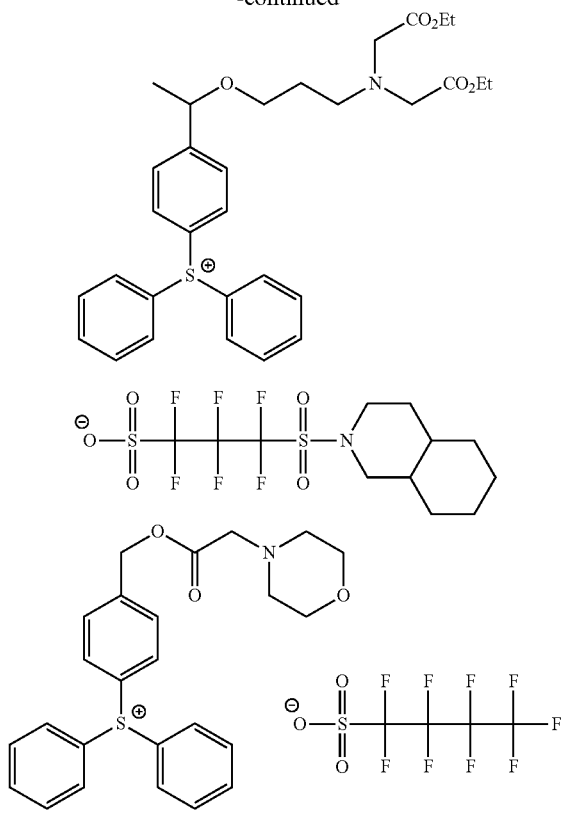
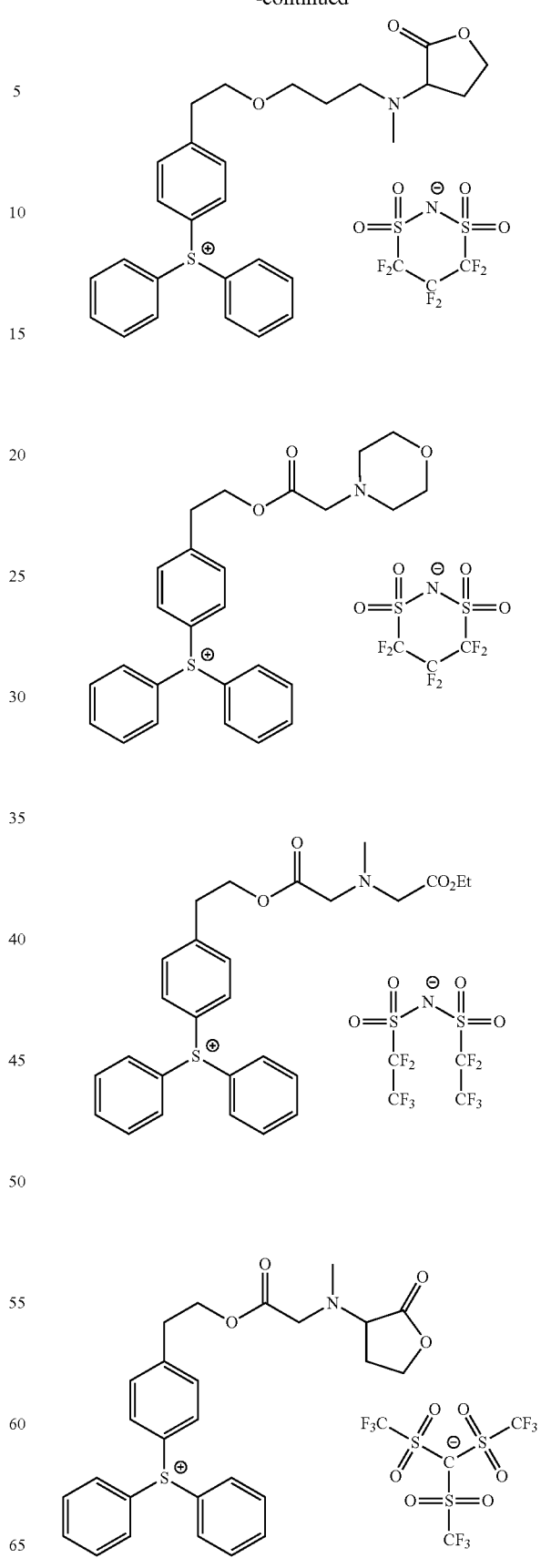

121
-continued
122
-continued
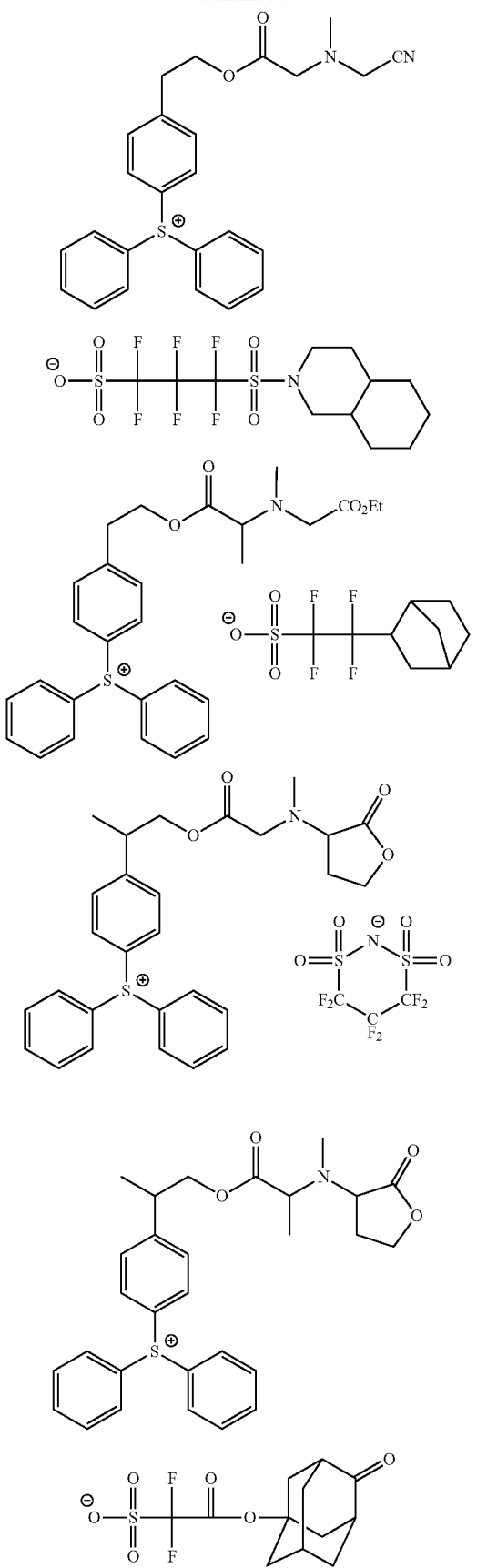
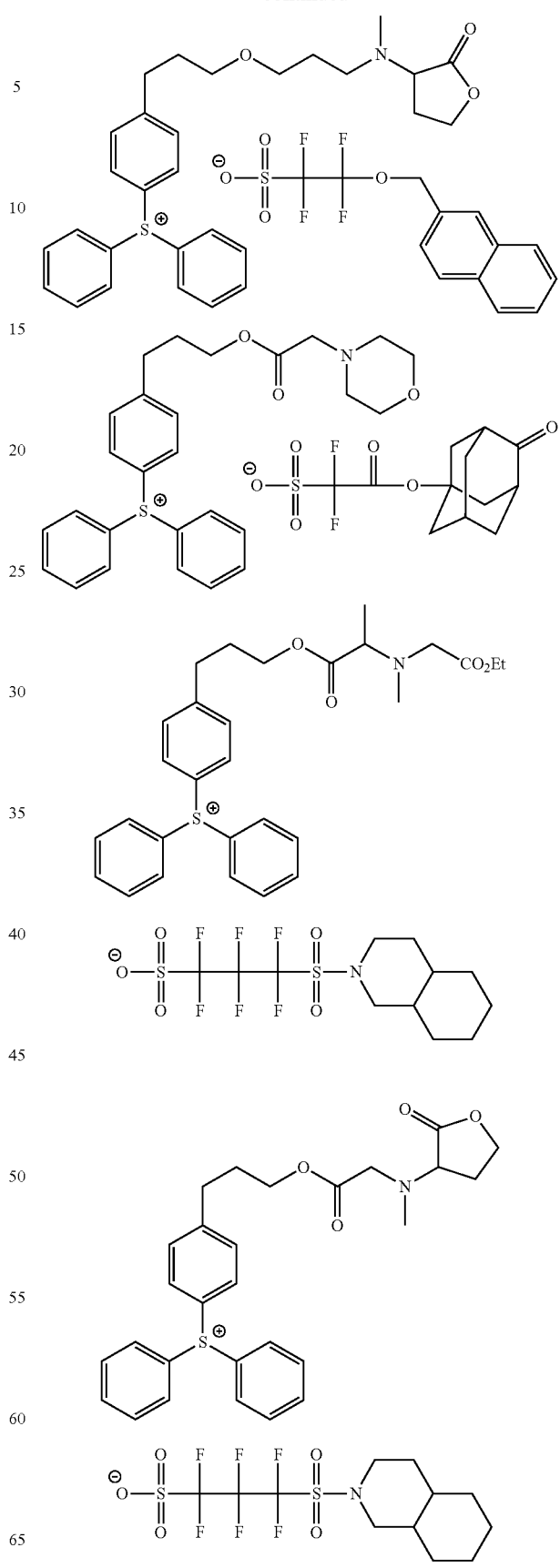

123
-continued
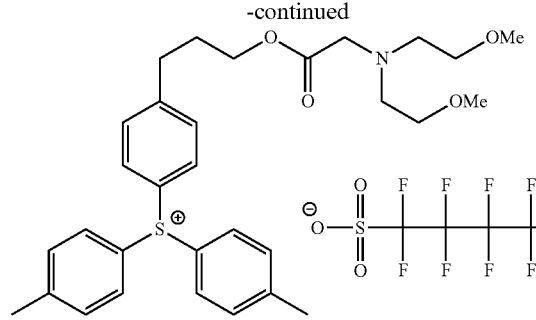
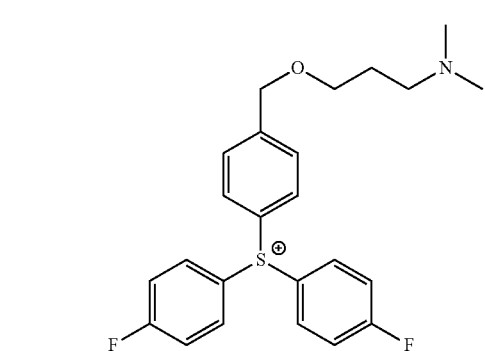
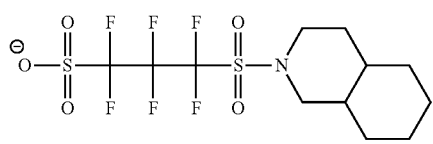
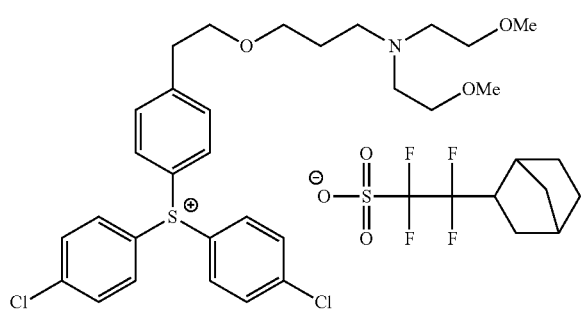
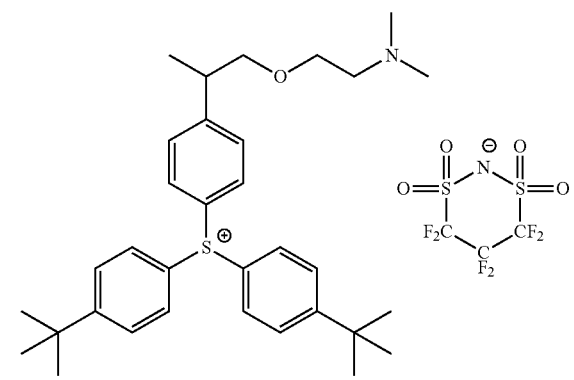
124
-continued
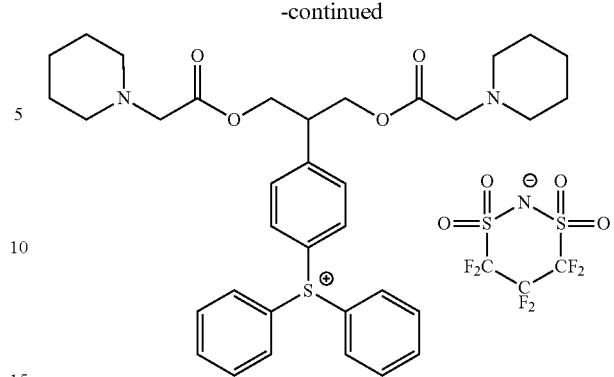
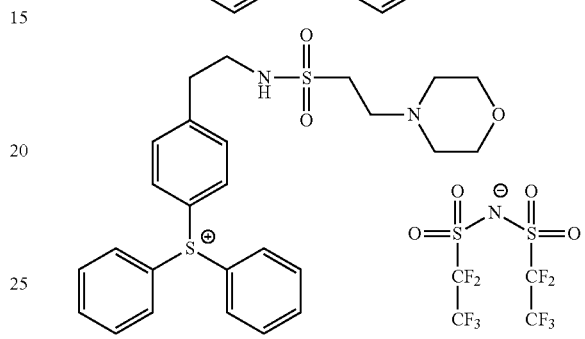
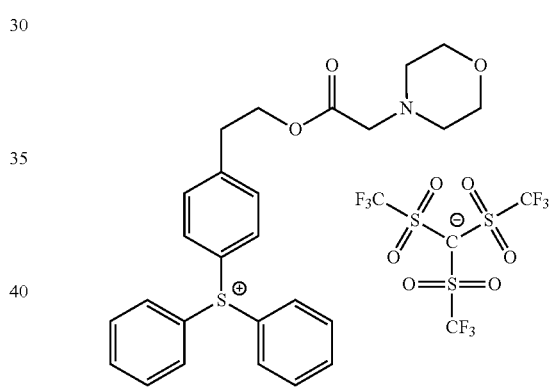
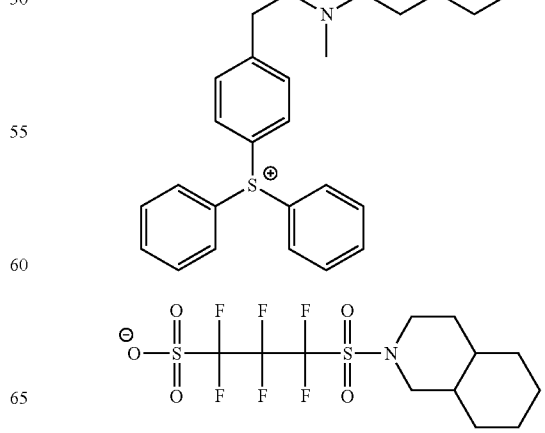

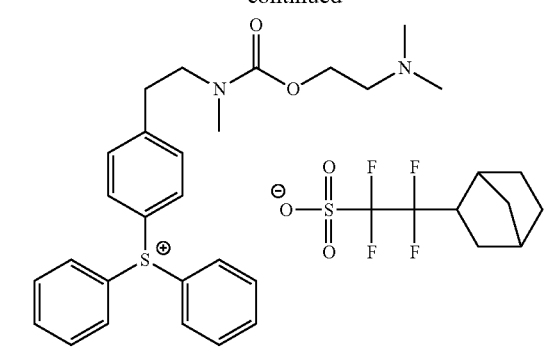
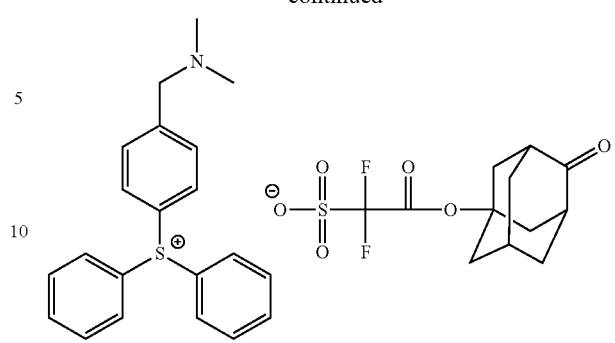
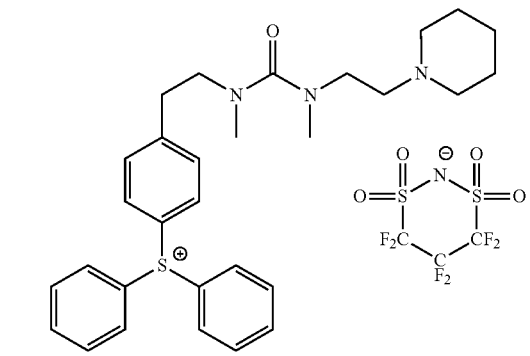
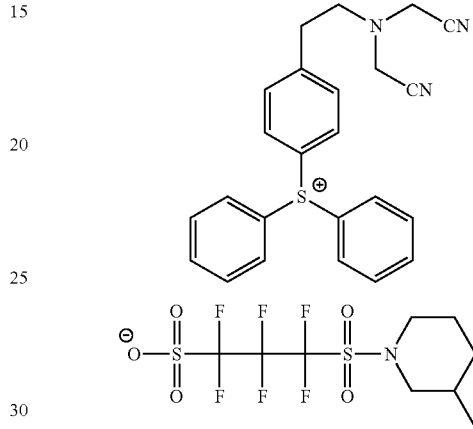
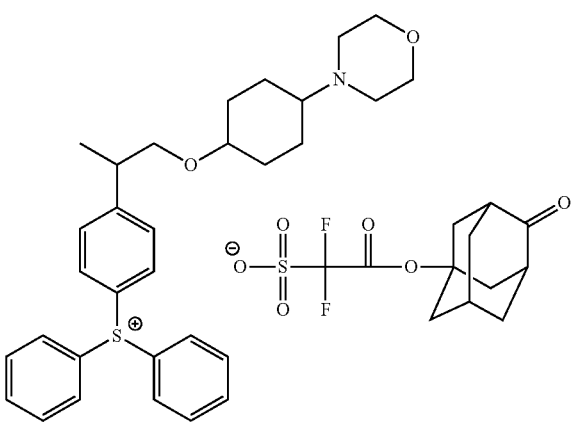
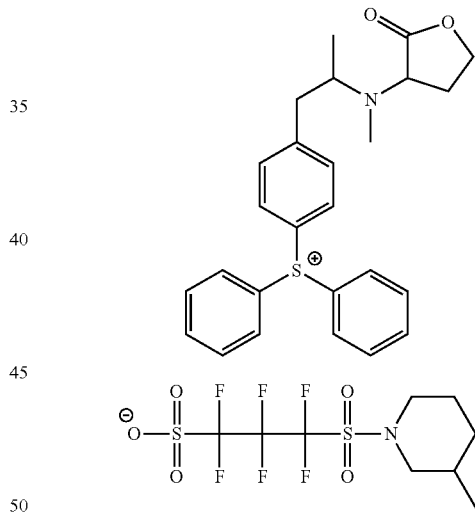
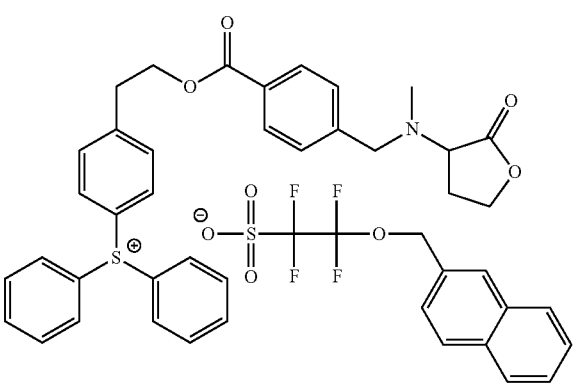
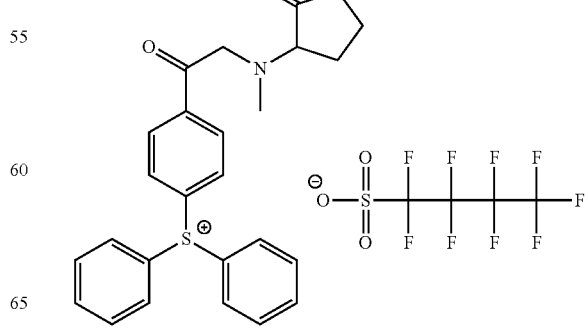

127
-continued
128
-continued
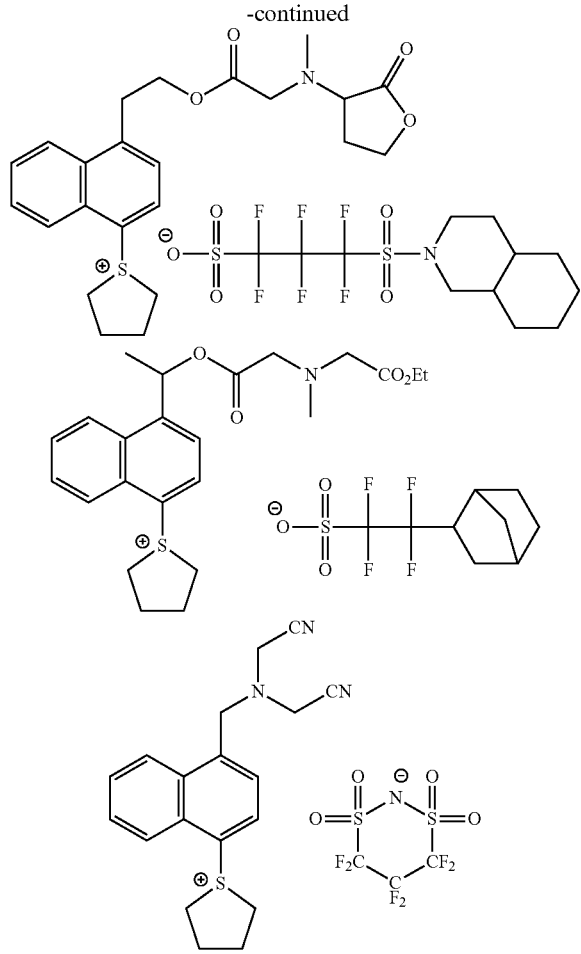
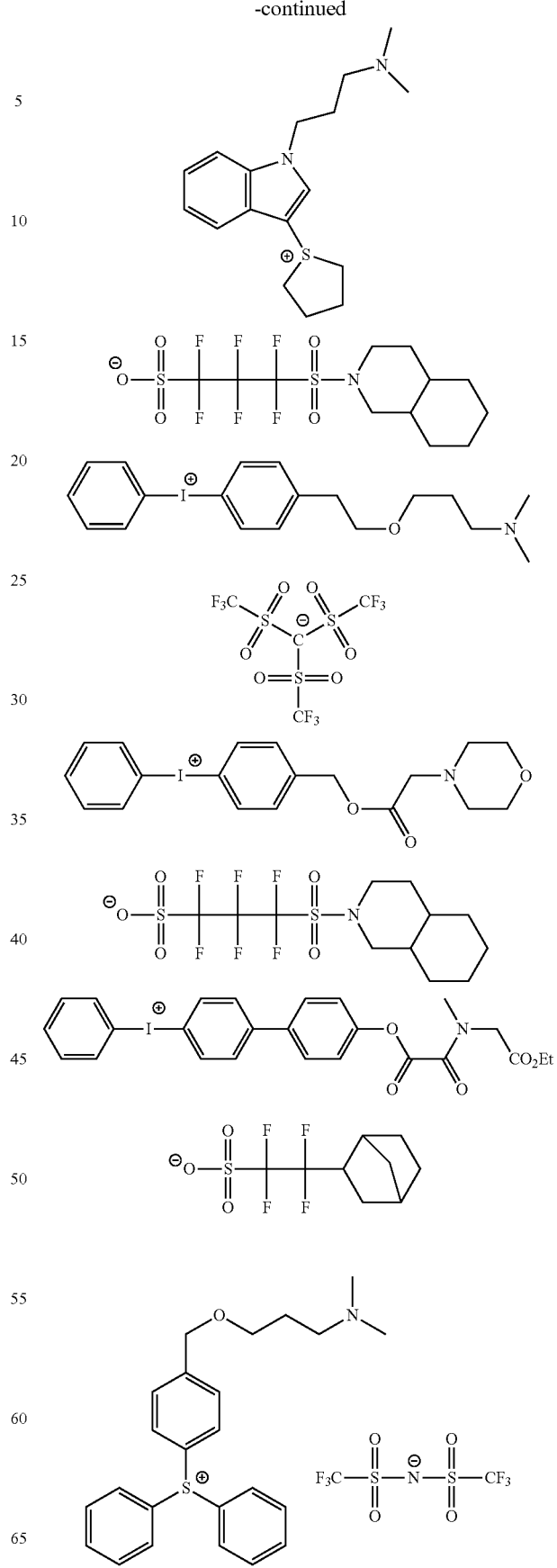

129
-continued
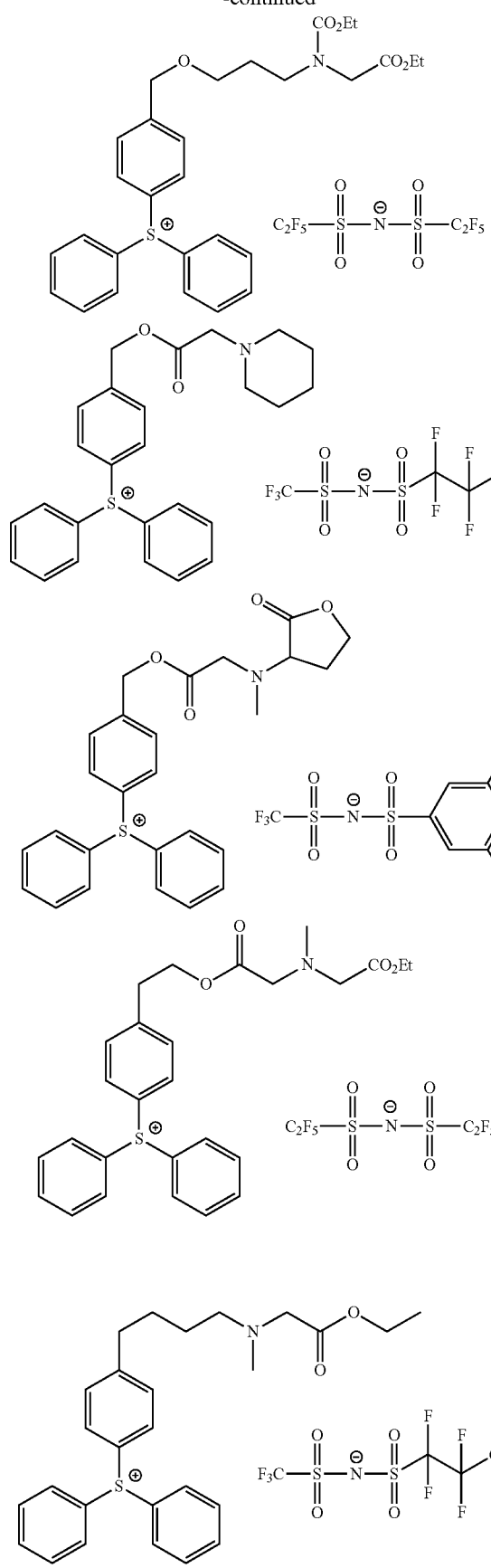
130
-continued
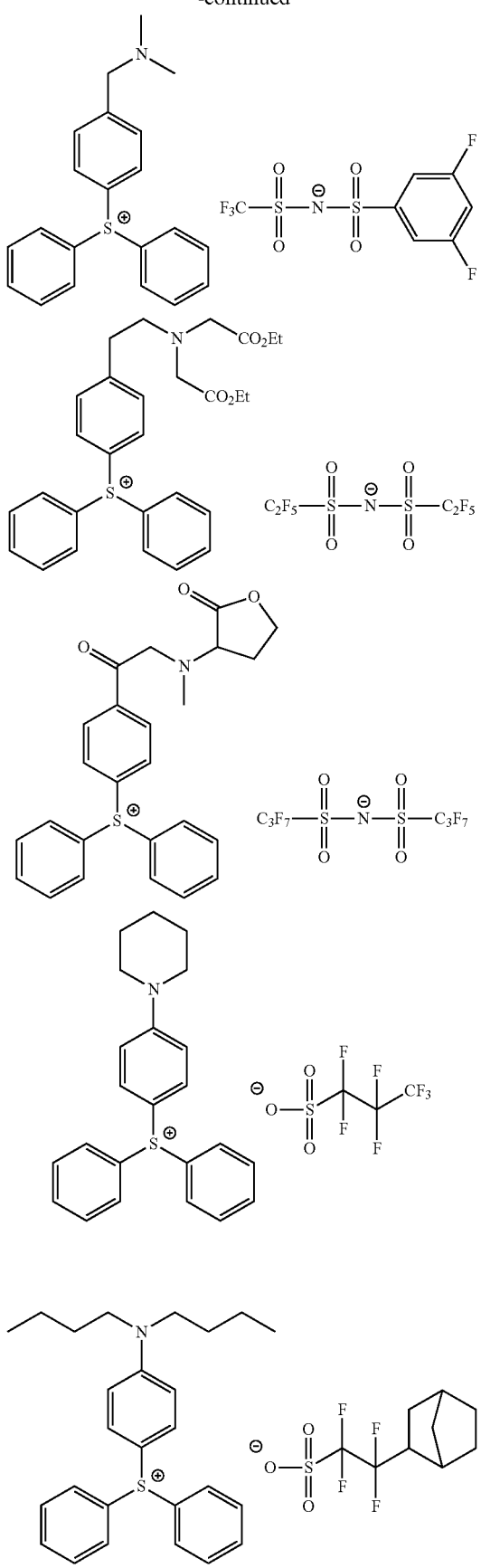

131
-continued
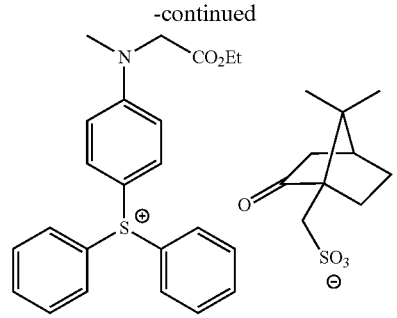
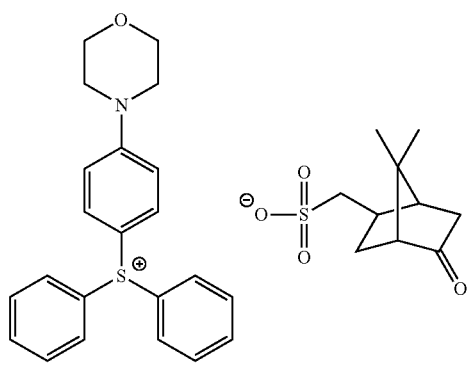
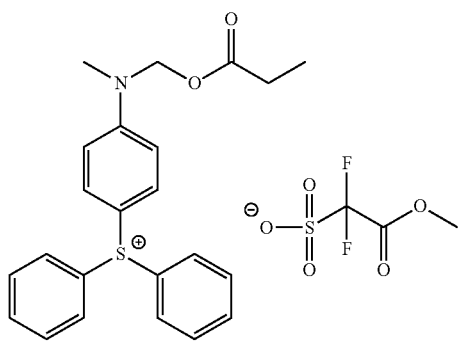
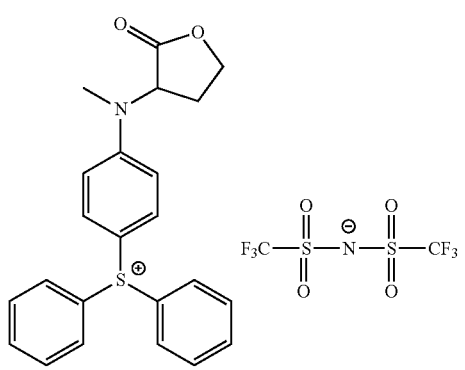
132
-continued
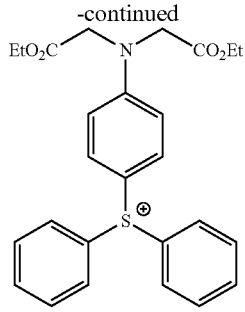
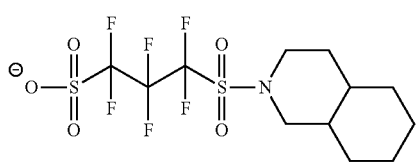
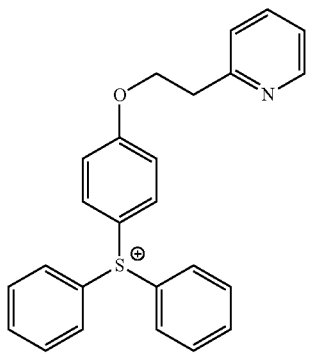
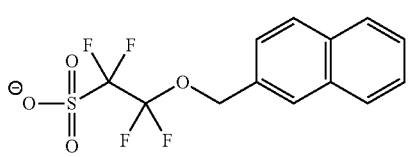
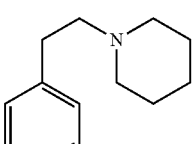
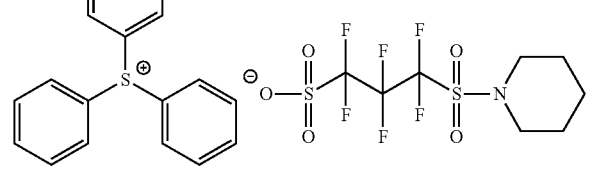
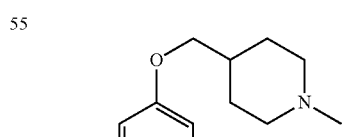
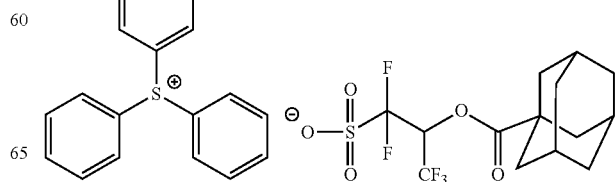

133
-continued
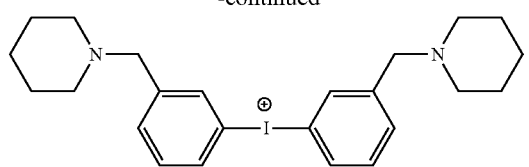
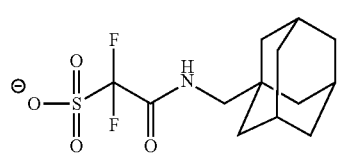
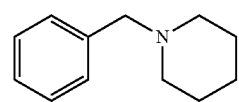
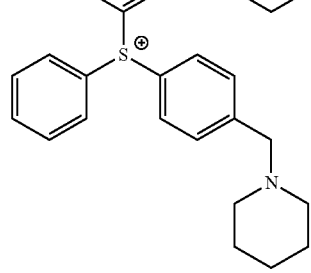
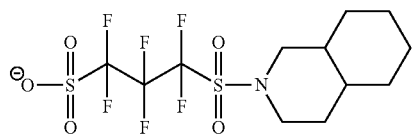
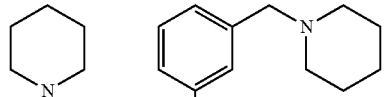
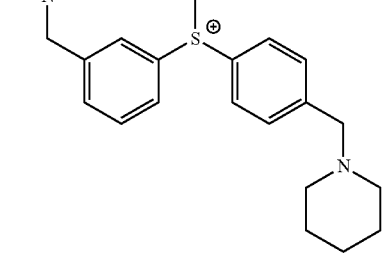
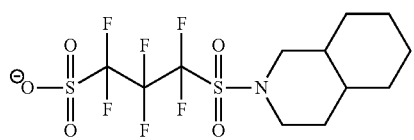
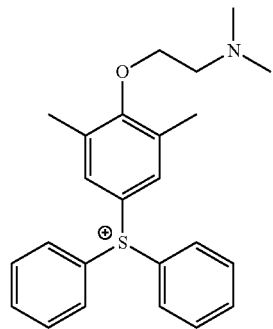
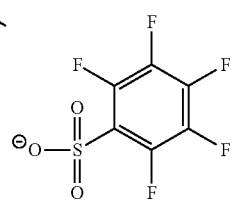
134
-continued
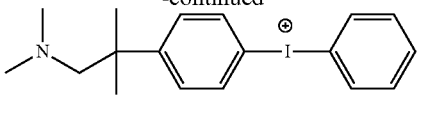
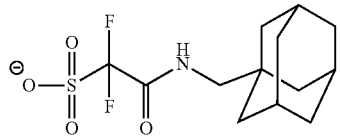
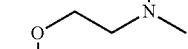
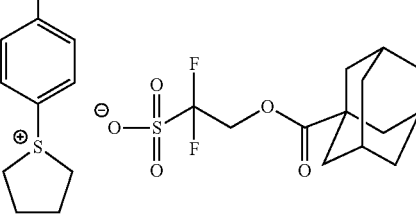
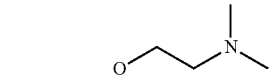
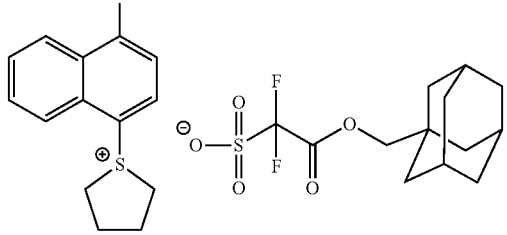
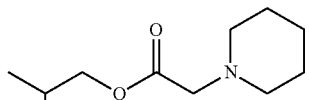
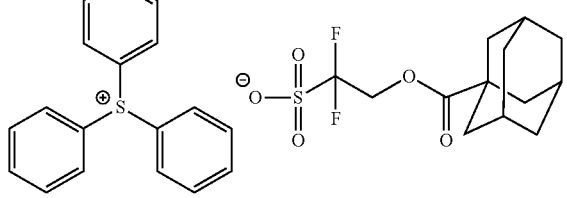
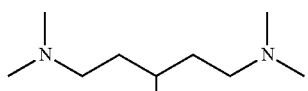
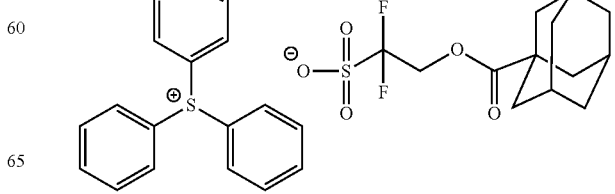

-continued

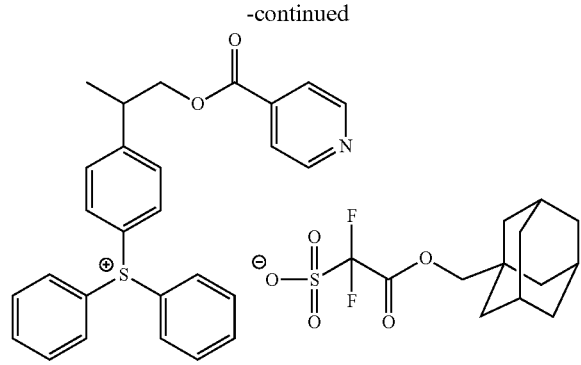

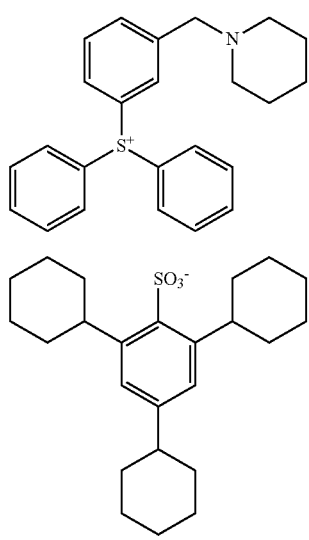

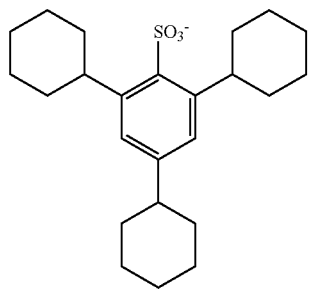

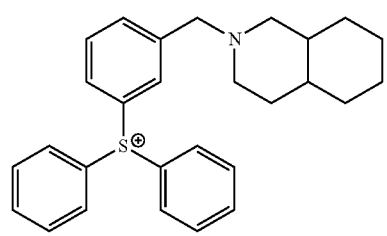

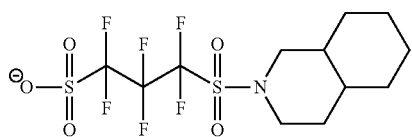

-continued

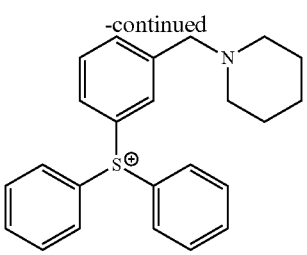

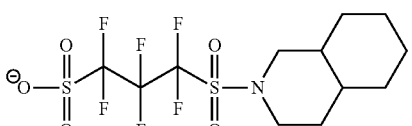

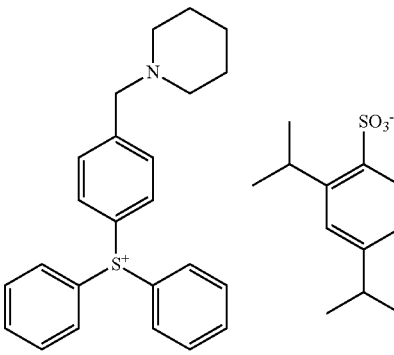

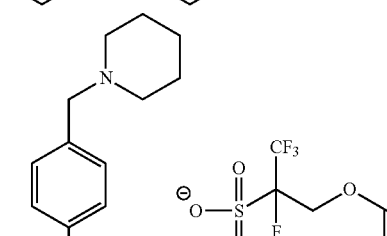

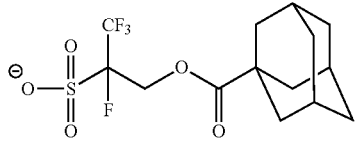

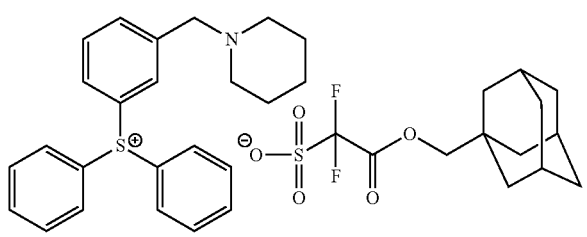

The compound (D) may be used alone or in combination of two or more thereof.

The content of the compound (D) is usually in the range of 0.001 mass % to 10 mass %, preferably 0.1 mass % to 10 mass %, and more preferably 1 mass % to 10 mass %, based on the total solid content of the composition.

In addition, a larger volume of an acid generated from the compound (D) is preferred from the viewpoint of enhancing the resolution.

<Surfactant>

The composition of the present invention may further contain a surfactant in order to improve the coatability. The surfactant is not particularly limited, but examples thereof may include a nonionic surfactant such as polyoxyethylene alkyl ethers, polyoxyethylene alkylallyl ethers, polyoxyethylene-polyoxypropylene block copolymers, sorbitan fatty acid esters, and polyoxyethylene sorbitan fatty acid esters, a fluorine-based surfactant such as MEGAFACE F171 and MEGAFACE F176 (manufactured by DIC Corporation), FLORAD FC430 (manufactured by Sumitomo 3M Limited), SURFYNOL E1004 (manufactured by Asahi Glass Co., Ltd.), and PF656 and PF6320 manufactured by OMNOVA Solutions Inc., an organosiloxane polymer, and a polysiloxane polymer.

In the case where the composition of the present invention contains a surfactant, the content of the surfactant is preferably 0.0001 mass % to 2 mass %, and more preferably 0.0005 mass % to 1 mass %, based on the total amount of the composition (excluding the solvent).

<Organic Carboxylic Acid>

The composition of the present invention preferably contains an organic carboxylic acid, in addition to the components described above. Examples of the organic carboxylic acid compound may include an aliphatic carboxylic acid, an alicyclic carboxylic acid, an unsaturated aliphatic carboxylic acid, an oxycarboxylic acid, an alkoxycarboxylic acid, a ketocarboxylic acid, a benzoic acid derivative, a phthalic acid, a terephthalic acid, an isophthalic acid, a 2-naphthoic acid, a 1-hydroxy-2-naphthoic acid, and a 2-hydroxy-3-naphthoic acid. However, when the electron beam exposure is performed in vacuum, the organic carboxylic acid may vaporize from the resist film surface to contaminate the inside of a lithography chamber. Thus, a preferred compound is an aromatic organic carboxylic acid, and above all, for example, a benzoic acid, a 1-hydroxy-2-naphthoic acid, and a 2-hydroxy-3-naphthoic acid are preferred.

The blending amount of the organic carboxylic acid is preferably 0.5 mass % to 15 mass %, and more preferably 2 mass % to 10 mass %, based on the total amount of the composition.

The composition of the present invention, as necessary, may further contain a dye, a plasticizer, and an acid amplifier (described in WO95/29968A, WO98/24000A, JP1996-305262A (JP-H08-305262A), JP1997-34106A (JP-H09-34106A), JP1996-248561A (JP-H08-248561A), JP1996-503082A (JP-H08-503082A), U.S. Pat. No. 5,445,917A, JP1996-503081A (JP-H08-503081A), U.S. Pat. No. 5,534,393A, U.S. Pat. No. 5,395,736A, U.S. Pat. No. 5,741,630A, U.S. Pat. No. 5,334,489A, U.S. Pat. No. 5,582,956A, U.S. Pat. No. 5,578,424A, U.S. Pat. No. 5,453,345A, EP665960B, EP757628B, EP665961B, U.S. Pat. No. 5,667,943A, JP1998-1508A (JP-H10-1508A), JP1998-282642A (JP-H10-282642A), JP1997-512498A (JP-H09-512498A), JP2000-62337A, JP2005-17730A, and JP2008-209889A). As for these compounds, respective compounds described in JP2008-268935A may be exemplified.

<Onium Carboxylate>

The composition of the present invention may contain an onium carboxylate. Examples of the onium carboxylate may include sulfonium carboxylate, iodonium carboxylate, and ammonium carboxylate. Particularly, as for the onium carboxylate, sulfonium carboxylate or iodonium carboxylate is preferred. Also, in the present invention, it is preferred that the carboxylate residue of the onium carboxylate does not contain an aromatic group and a carbon-carbon double bond. The anion moiety is particularly preferably a linear or branched, monocyclic or polycyclic alkylcarboxylate anion having 1 to 30 carbon atoms, and more preferably the carboxylate anion above in which the alkyl group is partially or completely fluorine-substituted. Also, the alkyl chain may contain an oxygen atom. Accordingly, the transparency to light at 220 nm or less is ensured, and thus the sensitivity and resolution are enhanced, and the iso/dense bias and exposure margin are improved.

The blending amount of the onium carboxylate is preferably 1 mass % to 15 mass %, and more preferably 2 mass % to 10 mass %, based on the total solid content of the composition.

<Acid Amplifier>

The actinic ray-sensitive or radiation-sensitive composition of the present invention may further include one or two or more of compounds (hereinafter also referred to as acid amplifiers) capable of decomposing by the action of an acid to generate acids. It is preferred for the acid generated by each acid amplifier to be a sulfonic acid, a methide acid, or an imidic acid. The content of the acid amplifier is preferably 0.1 mass % to 50 mass %, more preferably 0.5 mass % to 30 mass %, and still more preferably 1.0 mass % to 20 mass %, based on the total solid content of the composition.

The ratio of the acid amplifier to the acid generator added (solid content of the acid amplifier based on the total solid content of the composition/solid content of the acid generator based on the total solid content of the composition) is not particularly limited. However, the ratio is preferably 0.01 to 50, more preferably 0.1 to 20, and particularly preferably 0.2 to 1.0.

Hereinafter, examples of the acid amplifier that can be used in the present invention are shown, but are not limited thereto.

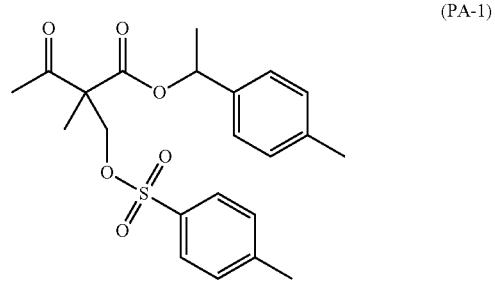

(PA-1)

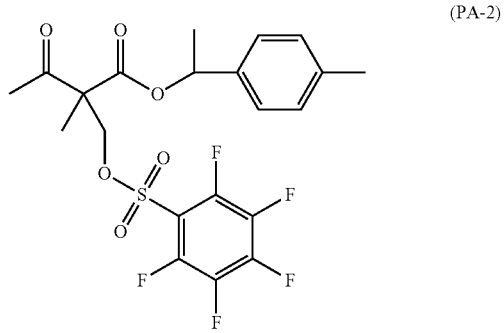

(PA-2)

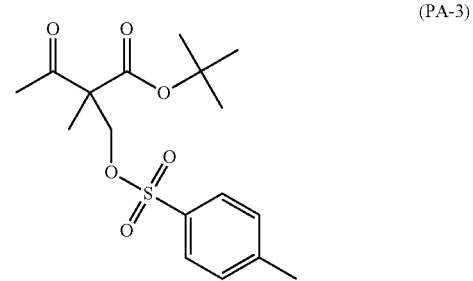

(PA-3)

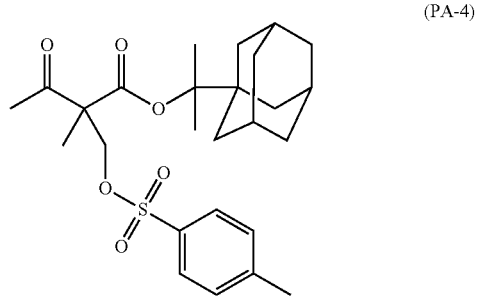

(PA-4)

-continued
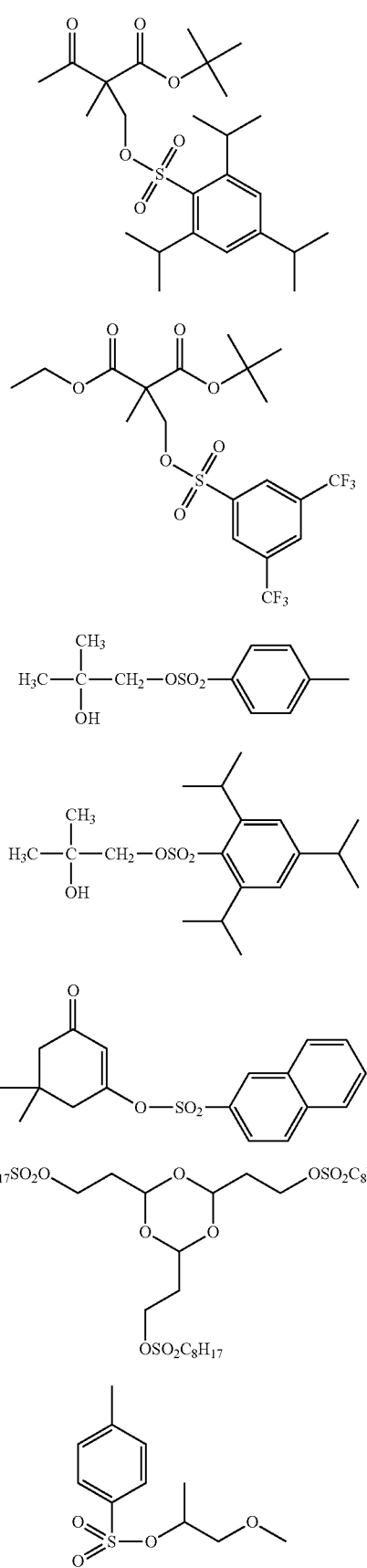
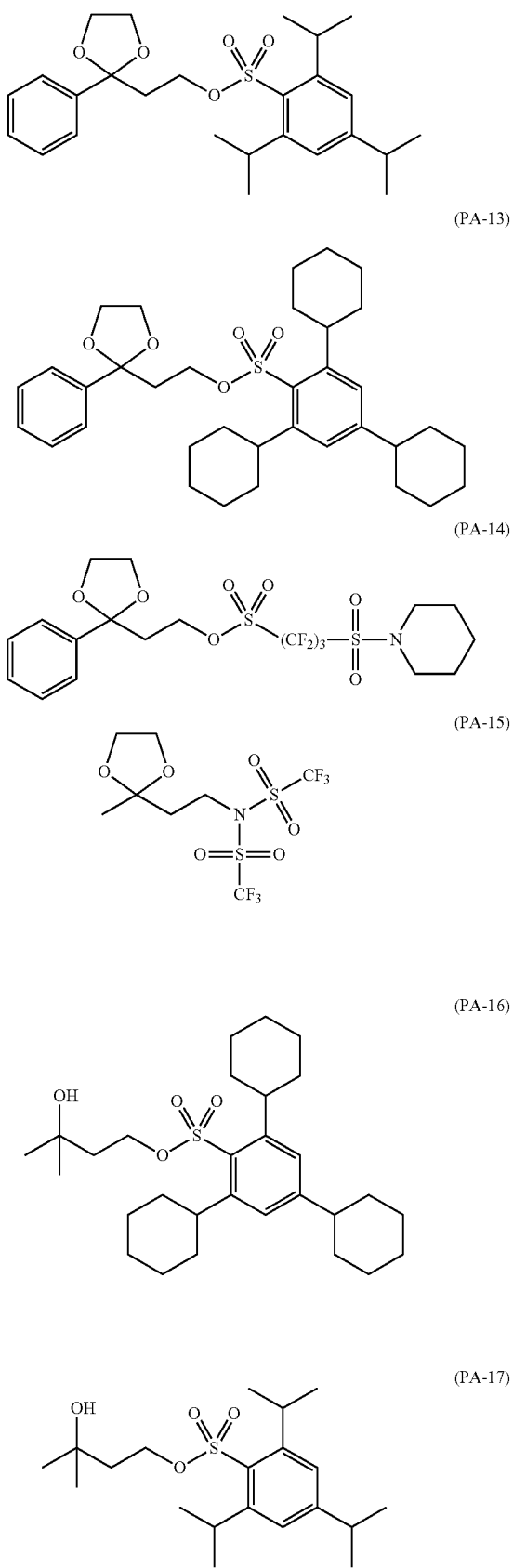

(PA-18)

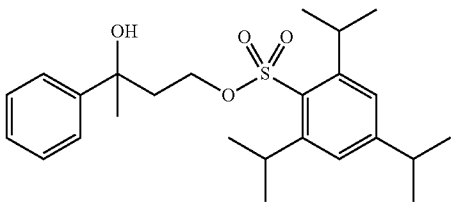

<Solvent>

The composition of the present invention may contain a solvent, and preferred examples of the solvent include ethylene glycol monoethyl ether acetate, cyclohexanone, 2-heptanone, propylene glycol monomethyl ether (PGME, another name: 1-methoxy-2-propanol), propylene glycol monomethyl ether acetate (PGMEA, another name: 1-methoxy-2-acetoxypropane), propylene glycol monomethyl ether propionate, propylene glycol monoethyl ether acetate, methyl 3-methoxypropionate, ethyl 3-ethoxypropionate, methyl β-methoxyisobutyrate, ethyl butyrate, propyl butyrate, methyl isobutyl ketone, ethyl acetate, isoamyl acetate, ethyl lactate, toluene, xylene, cyclohexyl acetate, diacetone alcohol, N-methylpyrrolidone, N,N-dimethylformamido, γ-butyrolactone, N,N-dimethylacetamido, propylene carbonate, and ethylene carbonate. These solvents are used alone or in combination thereof.

The solid content of the composition of the present invention is dissolved in the solvent, and is dissolved at a solid content concentration of preferably 1 mass % to 40 mass %, more preferably 1 mass % to 30 mass %, and still more preferably 3 mass % to 20 mass %.

<Actinic Ray-Sensitive or Radiation-Sensitive Film and Mask Blank>

The present invention also relates to an actinic ray-sensitive or radiation-sensitive film including the composition of the present invention, and such a film is formed, for example, by applying the composition of the present invention on a support such as a substrate. The thickness of the film is preferably 0.02 μm to 0.1 μm. As for the method of coating the composition on the substrate, an appropriate coating method such as spin coating, roll coating, flow coating, dip coating, spray coating, and doctor coating may be used. The spin-coating is preferred, and the spinning speed preferably is 1,000 rpm to 3,000 rpm. The coating film is pre-baked at 60° C. to 150° C. for 1 minute to 20 minutes, and preferably at 80° C. to 120° C. for 1 minute to 10 minutes to form a thin film.

As for a material which constitutes a substrate to be processed and its outermost layer, for example, in the case of a wafer for a semiconductor, a silicon wafer may be used, and as an example of a material used as the outermost layer, Si, $SiO_2$, SiN, SiON, TiN, WSi, BPSG, SOG, and an organic antireflection film may be exemplified.

Further, the present invention also relates to mask blank provided with the actinic ray-sensitive or radiation-sensitive film obtained as described above.

The photomask blank has a substrate, and is used, for example, for manufacturing a photomask. The substrate for photomask blank is, for example, a transparent substrate such as quartz or calcium fluoride. In general, a light-shielding film, an antireflection film, further a phase shift film, and additionally a required functional film, such as an etching stopper film and an etching mask film, are stacked on the substrate. As for the material of the functional film, a film containing silicon or a transition metal such as chromium, molybdenum, zirconium, tantalum, tungsten, titanium, and niobium is stacked. As the material used for the outermost layer, a material containing, as a main constituent component, a material which contains silicon or contains silicon and oxygen and/or nitrogen; a silicon compound material containing, as a main constituent component, the material described above which further contains a transition metal; and a transition metal compound material containing, as a main constituent component, a material which contains a transition metal, particularly, one or more transition metals selected from chromium, molybdenum, zirconium, tantalum, tungsten, titanium, and niobium, or further contains one or more elements selected from oxygen, nitrogen, and carbon are further exemplified.

The light-shielding film may have a single-layer structure, but more preferably has a multilayer structure where a plurality of materials are applied one on another. In the case of a multilayer structure, the film thickness per layer is not particularly limited, but is preferably 5 nm to 100 nm, and more preferably 10 nm to 80 nm. The thickness of the whole light-shielding film is not particularly limited, but is preferably 5 nm to 200 nm, and more preferably 10 nm to 150 nm.

In the case where the pattern formation is performed using a composition on the photomask blank having the material containing chromium and oxygen or nitrogen in the outermost layer thereof among the materials described above, a so-called undercut shape having a waisted shape near the substrate is likely to be formed in general. However, in the case of using the present invention, the undercut problem may be improved as compared with the conventional mask blank.

This actinic ray-sensitive or radiation-sensitive film is irradiated with actinic rays or radiation (for example, an electron beam) (hereinafter, also referred to as "exposure"), then preferably baked (usually at 80° C. to 150° C., more preferably 90° C. to 130° C.), and subsequently developed with water. In this manner, a good pattern may be obtained. A photomask is prepared using this pattern as a mask. Further, after subjecting to appropriate etching, ion implantation, or the like, mask blank may also be used to produce, for example, a semiconductor fine circuit, or an imprint mold structure.

Meanwhile, the process for preparing an imprint mold by using the composition of the present invention is described, for example, in JP4109085B, JP2008-162101A, and "Basic and Technology Expansion-Application Development of Nanoimprint-Substrate Technology of Nanoimprint and Latest Technology Expansion-edited: Yoshihiko Hirai (Frontier Publishing)".

<Pattern Forming Method>

The composition of the present invention can be appropriately used in the following negative pattern forming process. That is, the composition of the present invention can be preferably used in a process including applying the composition onto a substrate to thereby form a resist film, irradiating the resist film with actinic rays or radiation (namely, exposure to light), and developing the exposed film with a developer to thereby obtain a negative pattern. As this process, use can be made of any of processes described in, for example, JP2008-292975A and JP2010-217884A.

The present invention also relates to a pattern forming method which includes exposing the above resist film or the mask blank provided with the film to light and developing the exposed resist film or the exposed mask blank provided with the film to light. In the present invention, the exposure is preferably performed using an electron beam or extreme ultraviolet rays.

In the manufacturing of a precision integrated circuit element, at the exposure on the resist film (a pattern forming step), first, it is preferred to perform patternwise irradiation of an electron beam or extreme ultraviolet rays (EUV) on the resist film of the present invention. The exposure is performed at an exposure dose ranging from about 0.1 µC/cm² to 20 µC/cm² and preferably about 3 µC/cm² to 10 µC/cm² in a case of an electron beam, and an exposure dose ranging from about 0.1 mJ/cm² to 20 mJ/cm² and preferably from about 3 mJ/cm² to 15 mJ/cm² in a case of extreme ultraviolet rays. Then, on a hot plate, the film is subjected to post-exposure baking (PEB) at 60° C. to 150° C. for 1 minute to 20 minutes, preferably at 80° C. to 120° C. for 1 minute to 10 minutes, and then is developed, rinsed and dried to form a pattern. The development is performed using a developer through a conventional method such as a dip method, a puddle method, or a spraying method for 0.1 minutes to 3 minutes, and preferably 0.5 minutes to 2 minutes.

The developer used in the step of developing the actinic ray-sensitive or radiation-sensitive film formed using the composition of the present invention is not particularly limited, and for example, a developer containing an alkali developer or an organic solvent (hereinafter, also referred to as organic developer) may be used.

As the alkali developer, use can be made of an alkaline aqueous solution of the followings: inorganic alkalis such as sodium hydroxide, potassium hydroxide, sodium carbonate, sodium silicate, sodium metasilicate, and aqueous ammonia; primary amines such as ethylamine and n-propylamine; secondary amines such as diethylamine and di-n-butylamine; tertiary amines such as triethylamine and methyldiethylamine; alcohol amines such as dimethylethanolamine and triethanolamine; tetraalkylammonium hydroxides such as tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, ethyltrimethylammonium hydroxide, butyltrimethylammonium hydroxide, methyltriamylammonium hydroxide, and dibutyldipentylammonium hydroxide; quaternary ammonium salts such as trimethylphenylammonium hydroxide, trimethylbenzylammonium hydroxide, and triethylbenzylammonium hydroxide; or cyclic amines such as pyrrole and piperidine. Furthermore, to the above alkaline aqueous solution, alcohols or a surfactant may be added in an appropriate amount. The alkali concentration of the alkali developer is usually 0.1 mass % to 20 mass %. The pH of the alkali developer is usually 10.0 to 15.0. The alkali developer may be used after appropriate adjustment of the alkali concentration and pH thereof. Alkali developer may be used with addition of a surfactant or an organic solvent.

As the organic developer, use can be made of not only a polar solvent, such as an ester-based solvent (butyl acetate, ethyl acetate, and the like), a ketone-based solvent (2-heptanone, cyclohexanone, and the like), an alcohol-based solvent, an amido-based solvent, or an ether-based solvent, but also a hydrocarbon solvent. The content of water in the organic developer as a whole is preferably less than 10 mass %. More preferably, the organic developer contains substantially no trace of water.

A quaternary ammonium salt whose representative is tetramethylammonium hydroxide is generally used in the alkali developer. Besides this, use can be made of an alkaline aqueous solution of an inorganic alkali, a primary amine, a secondary amine, a tertiary amine, an alcohol amine, a cyclic amine, or the like. Appropriate amounts of alcohols or a surfactant can be added to the above alkali developer before use. The alkali concentration of the alkali developer is generally 0.1 mass % to 20 mass %. The pH value of the alkali developer is generally 10.0 to 15.0.

Furthermore, alcohols or a surfactant may be added in an appropriate amount to the above alkaline aqueous solution.

The composition of the present invention is a negative resist composition for use in the formation of a negative pattern, so that the film therefrom at unexposed areas is dissolved while the film therefrom at exposed areas has less tendency to be dissolved in the developer due to the cross-linking of compounds. Utilizing this, a desired pattern can be formed on substrates.

The pattern forming method of the present invention can also be used for guide pattern formation in Directed Self-Assembly (DSA) (see, for example, ACS Nano Vol. 4, No. 8, pp. 4815-4823).

The resist pattern formed according to the aforementioned method may also be used as a core material (core) in the spacer process disclosed in JP1991-270227A (JP-H03-270227A), and JP2013-164509A.

Furthermore, the present invention also relates to a method for manufacturing an electronic device in which the above-described pattern forming method of the present invention is included, and an electronic device manufactured by the manufacturing method.

The electronic device of the present invention is appropriately mounted in electrical and electronic devices (for example, home appliances, OA/media-related devices, optical devices, and communication devices).

EXAMPLES

Hereinafter, the present invention will be described in more detail with reference to examples, but is not limited thereto.

(Synthesis Example) Synthesis of Crosslinking Agent (C-1)

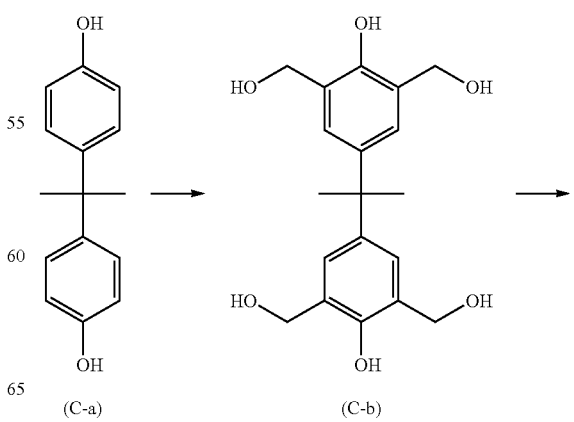

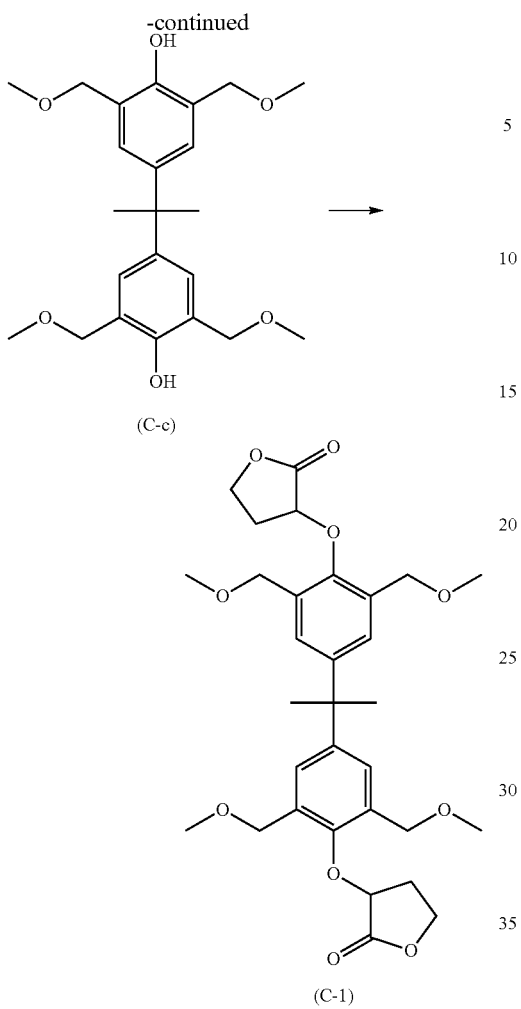

(C-c)

(C-1)

20 g of a commercially available compound (C-a) was mixed with 20 g of methanol, 100 g of water, and 12.3 g of potassium hydroxide in a 500 ml recovery flask. 26 g of paraformaldehyde was added to the mixture, followed by stirring at 50° C. for 6 hours to obtain a reaction solution. The resulting reaction solution was cooled to room temperature, and adjusted to about pH 5 by neutralization using 3N HCl (aq). Then, 120 g of ethyl acetate was added to carry out liquid separation. The resulting organic layer was washed with 120 g of water and concentrated to give 17.4 g of a compound (C-b).

Next, 17.4 g of the obtained compound (C-b) was dissolved in 170 g of methanol, and 1 g of sulfuric acid was added thereto, followed by heating to reflux for 4 hours to obtain a reaction solution. The resulting reaction solution was poured into 170 g of an aqueous saturated sodium bicarbonate solution, to which 200 g of ethyl acetate was then added to carry out liquid separation. The organic layer was washed three times with 200 g of water to give 15.2 g of a compound (C-c).

15.2 g of the compound (C-c) was dissolved in 75 g of methyl ethyl ketone. To the solution were added 15.5 g of α-bromo-γ-butyrolactone and 13.0 g of potassium carbonate, followed by stirring at 80° C. for 4 hours to obtain a reaction solution. Then, 100 g of water and 10 g of ethyl acetate were added to the reaction solution to carry out liquid separation. The organic layer was washed three times with 100 g of water and then concentrated to obtain a crude product. This crude product was purified by column chromatography to give 10.1 g of a crosslinking agent (C-1). FIG. 1 is a $^1$H-NMR (acetone-d6) chart of the crosslinking agent (C-1).

(Synthesis Example) Synthesis of Crosslinking Agent (C-2)

Figure 2:
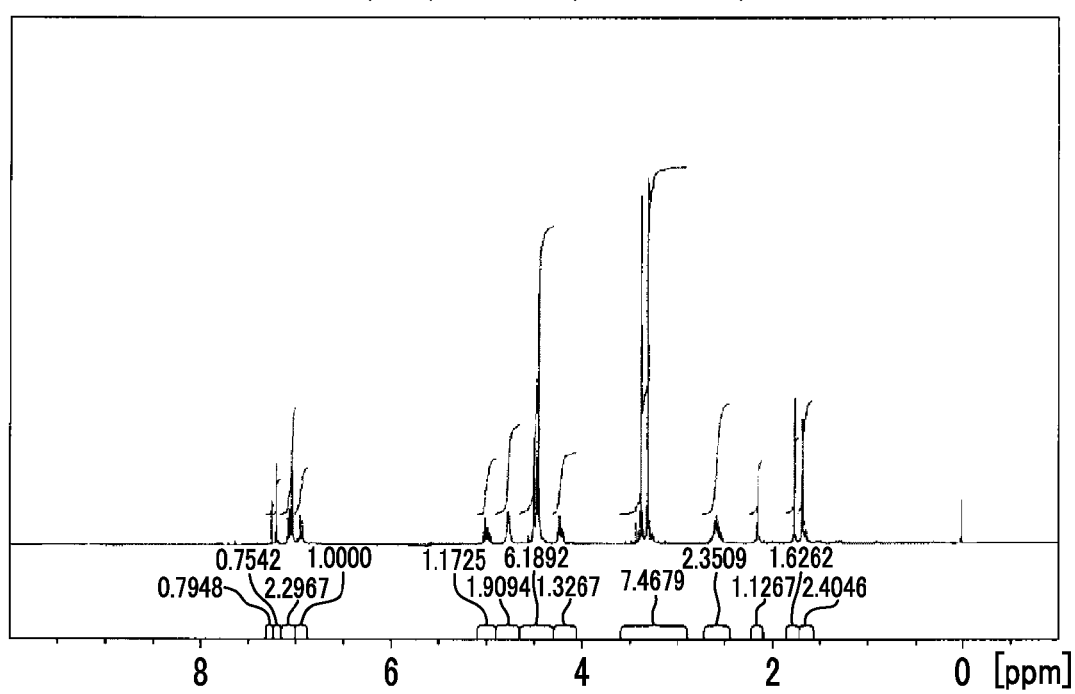
FIG. 2 shows an NMR chart ($^1$HNMR, acetone-d6) of a crosslinking agent (C-2) synthesized in Examples.

The crosslinking agent (C-2) given below was synthesized in the same manner as in the synthesis method of the crosslinking agent (C-1). FIG. 2 is a $^1$H-NMR (acetone-d6) chart of the crosslinking agent (C-2).

Crosslinking agents to be shown hereinafter other than the crosslinking agents (C-1) and (C-2) were also synthesized in the same manner as in the synthesis method of the crosslinking agent (C-1).

<Crosslinking Agent>

(C-1)

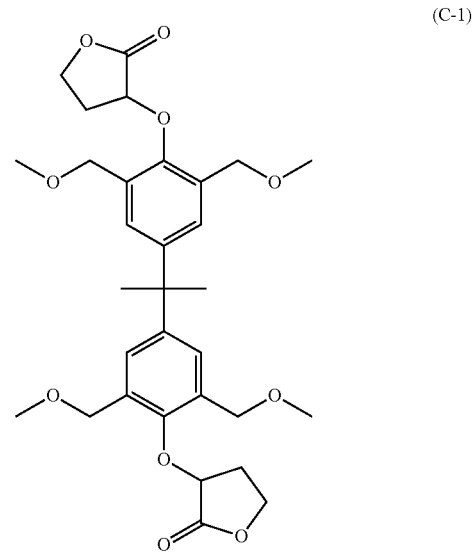

(C-2)

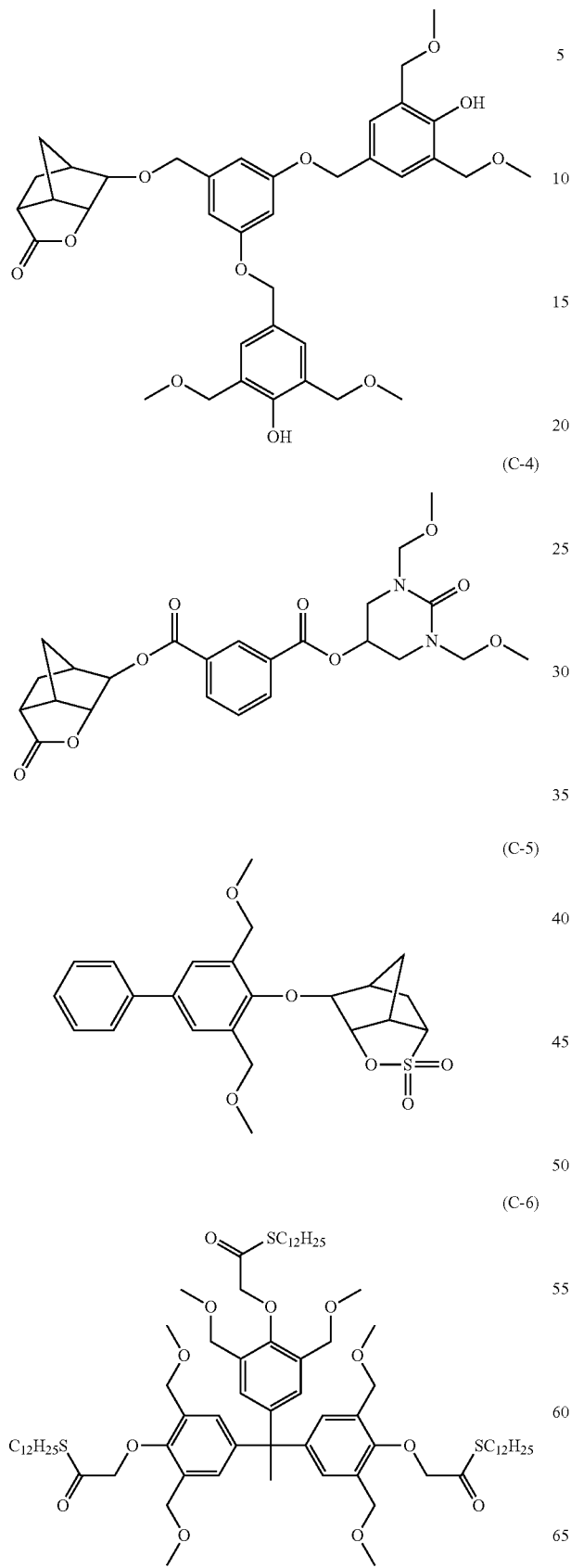
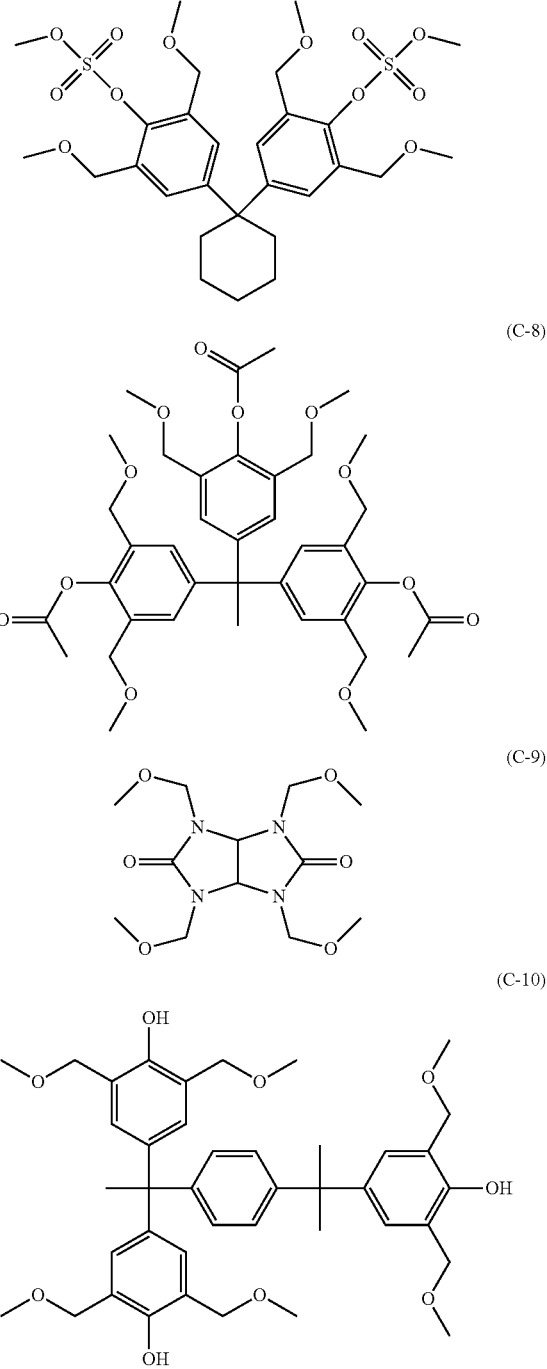

<Alkali-Soluble Resin>

As the alkali-soluble resin, resins (P-1) to (P-7) given below were used. The composition ratio (molar ratio), weight average molecular weight Mw, and polydispersity Mw/Mn are given therewith. Here, the weight average molecular weight Mw (in terms of polystyrene), number average molecular weight Mn (in terms of polystyrene), and polydispersity Mw/Mn were calculated by GPC (solvent: THF) measurement. In addition, the composition ratio (molar ratio) was calculated by $^1$H-NMR measurement.

| | | | |
|---|---|---|---|
| (P-1) | 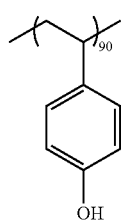 | 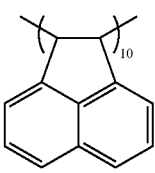 | Mw = 11700<br>Mw/Mn = 1.2 |
| (P-2) | 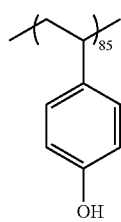 | 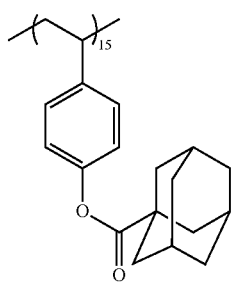 | Mw = 4600<br>Mw/Mn = 1.3 |
| (P-3) | 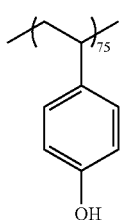 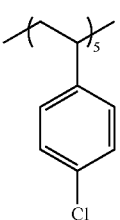 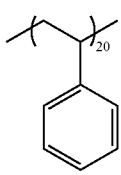 | | Mw = 5400<br>Mw/Mn = 1.6 |
| (P-4) | 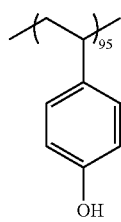 | 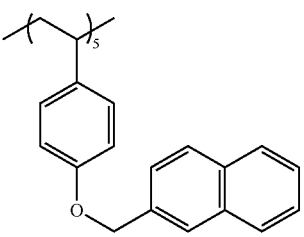 | Mw = 12000<br>Mw/Mn = 1.2 |
| (P-5) | 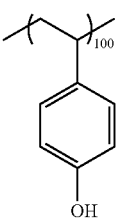 | | Mw = 9200<br>Mw/Mn = 1.1 |
| (P-6) | 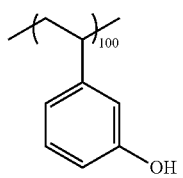 | | Mw = 4500<br>Mw/Mn = 1.1 |

-continued
(P-7) 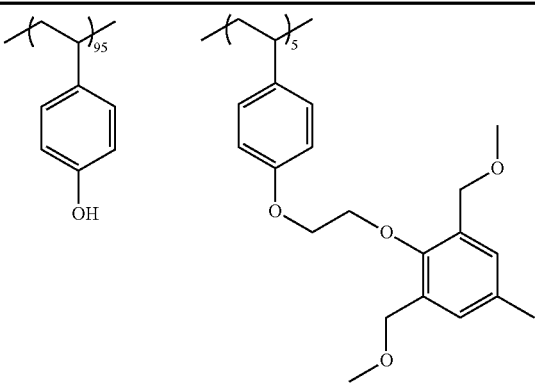
Mw = 4000
Mw/Mn = 1.1
<Acid Generator>
As the acid generator, compounds PAG-1 to PAG-5 given below were used.
(PAG-1)
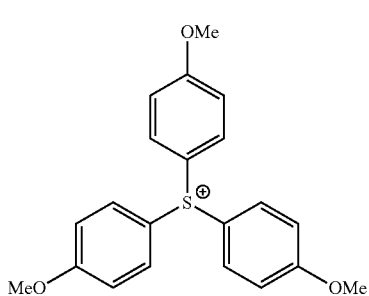
(PAG-2)
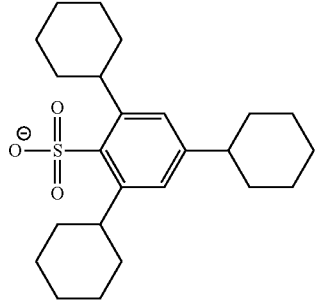
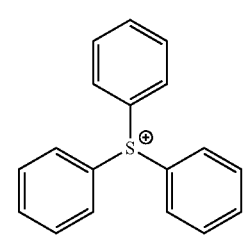
(PAG-3)
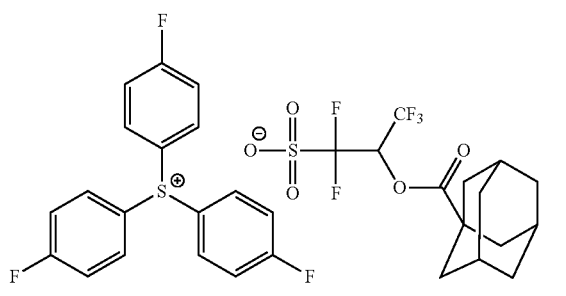
(PAG-4)
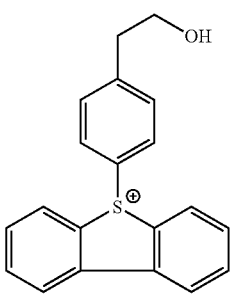
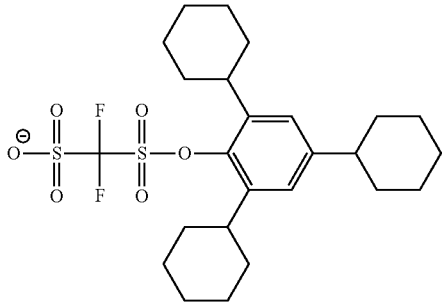
(PAG-5)
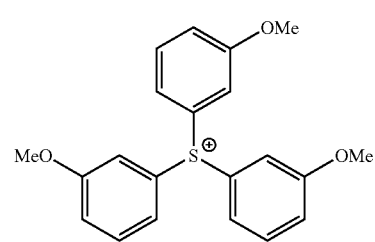
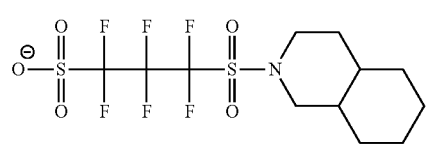

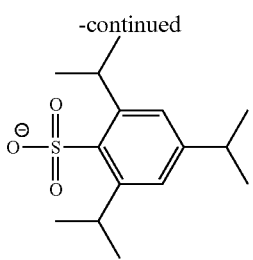

<Basic Compound>
As the basic compound, compounds D-1 to D-5 given below were used.

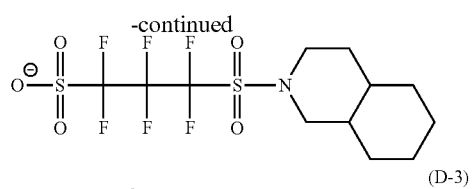

(D-3)

(D-4)

(D-5)

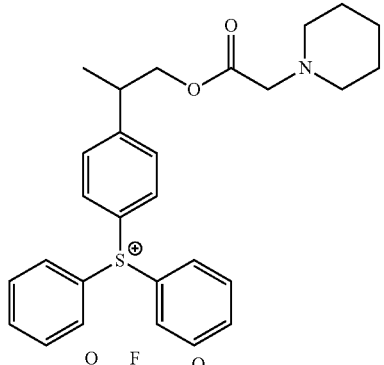
(D-1)

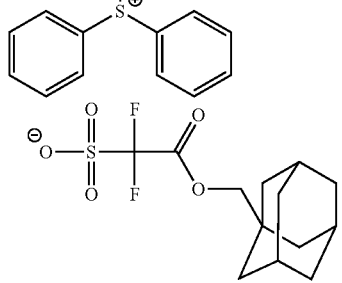
(D-2)

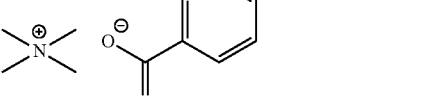

<Additives>
E1: 2-Hydroxy-3-naphthoic acid
E2: 2-Naphthoic acid
E3: Benzoic acid <Surfactant>
W-1: PF6320 (manufactured by OMNOVA Solutions Inc.)
W-2: MEGAFACE F176 (manufactured by DIC Corporation; fluorine-based)
W-3: Polysiloxane polymer KP-341 (Shin-Etsu Chemical Co., Ltd.; silicon-based)

<Solvent>
SL-1: Propylene glycol monomethyl ether (1-methoxy-2-propanol)
SL-2: Propylene glycol monomethyl ether acetate (1-methoxy-2-acetoxypropane)
SL-3: 2-Heptanone
SL-4: Ethyl lactate
SL-5: Cyclohexanone
SL-6: γ-Butyrolactone
SL-7: Propylene carbonate

TABLE 1

| Resist compo- sition | Alkali- soluble resin | Acid (g) generator | Basic (g) compound | Cross- linking (g) agent | (g) | Addi- tive | (g) | Surfac- tant | (g) | Solvent | (Mass ratio) | Solid content concen- tration (mass %) |
|---|---|---|---|---|---|---|---|---|---|---|---|---|
| R-1 | P-1 | 10 PAG-1 | 2.3 D-2 | 0.5 C-7 | 4.2 | | | W-3 | 0.05 | SL-3/SL-6 | 70/30 | 4.0 |
| R-2 | P-2 | 10 PAG-5 | 2.9 D-5 | 0.5 C-1 | 4.2 | E-1 | 0.2 | W-3 | 0.05 | SL-1/SL-6 | 80/20 | 4.0 |
| R-3 | P-3 | 10 PAG-5 | 2.5 D-3 | 0.5 C-2 | 4.1 | | | W-1 | 0.05 | SL-1/SL-7 | 90/10 | 4.0 |
| R-4 | P-4 | 10 PAG-3 | 2.4 D-1 | 0.4 C-1/C-9 | 2.1/2.1 | | | W-2 | 0.05 | SL-1/SL-5 | 60/40 | 4.0 |
| R-5 | P-5 | 10 PAG-4 | 3 D-4 | 0.5 C-3 | 4.3 | E-2 | 0.3 | W-3 | 0.05 | SL-2/SL-7 | 90/10 | 4.0 |
| R-6 | P-6 | 10 PAG-2 | 2.3 D-1 | 0.5 C-4 | 4.3 | | | W-2 | 0.05 | SL-1/SL-5/SL-7 | 70/20/10 | 4.0 |
| R-7 | P-7 | 10 PAG-4 | 2.7 D-3 | 0.4 C-6 | 4.2 | | | W-1 | 0.05 | SL-3/SL-6 | 90/10 | 4.0 |
| R-8 | P-1 | 10 PAG-2 | 2.6 D-4 | 0.5 C-3 | 4.3 | E-3 | 0.3 | W-2 | 0.05 | SL-1/SL-5 | 60/40 | 4.0 |
| R-9 | P-2 | 10 PAG-3 | 2.8 D-5 | 0.2 C-3 | 4.1 | | | W-1 | 0.05 | SL-1/SL-5 | 80/20 | 4.0 |
| R-10 | P-3 | 10 PAG-5 | 2.4 D-5 | 0.4 C-5 | 4.8 | | | W-1 | 0.05 | SL-1/SL-5 | 80/20 | 4.0 |
| R-11 | P-5/P-6 | 8/2 PAG-3 | 2.1 D-2 | 0.5 C-2/C-4 | 3/1.2 | E-3 | 0.3 | W-3 | 0.05 | SL-1/SL-5 | 70/30 | 4.0 |
| R-12 | P-4 | 10 PAG-4 | 1.9 D-3 | 0.2 C-2/C-10 | 3.0/1.0 | E-2 | 0.3 | W-1 | 0.05 | SL-3/SL-4 | 80/20 | 4.0 |
| R-13 | P-2/P-7 | 5/5 PAG-1 | 2.7 D-4 | 0.3 C-4 | 4.2 | | | W-3 | 0.05 | SL-1/SL-5 | 60/40 | 4.0 |

TABLE 1-continued

| Resist compo-sition | Alkali-soluble resin | Acid generator | (g) | Basic compound | (g) | Cross-linking agent | (g) | Addi-tive | Surfac-tant | (g) | Solvent | (Mass ratio) | Solid content concen-tration (mass %) |
|---|---|---|---|---|---|---|---|---|---|---|---|---|---|
| R-14 | P-1 | PAG-1 | 10 | D-2 | 2.3 | C-8 | 0.5 | 4.2 | W-3 | 0.05 | SL-3/SL-6 | 70/30 | 4.0 |
| R-15 | P-5 | PAG-4 | 10 | D-4 | 3 | C-9 | 0.5 | 4.3 E-2 | 0.3 W-3 | 0.05 | SL-2/SL-7 | 90/10 | 4.0 |
| R-16 | P-2 | PAG-3 | 10 | D-5 | 2.8 | C-10 | 0.2 | 4.1 | W-1 | 0.05 | SL-1/SL-5 | 80/20 | 4.0 |

<EB Exposure; Negative; Alkali Developing>

[Preparation of Support]

A Cr oxide-deposited 6-inch wafer (a wafer subjected to a treatment of forming a shielding film, which is used for conventional photomask blank) was prepared as a support.

[Preparation of Resist Coating Solution]

The components shown in Table 1 were dissolved in a solvent to prepare a solution having a total solid content concentration of 4.0 mass % for each case. This solution was filtered through a polytetrafluoroethylene filter having a pore size of 0.04 μm to prepare a resist solution.

[Preparation of Resist Film]

The resist coating solution was coated on the above-described Cr oxide-deposited 6-inch wafer by using a spin coater, MARK 8, manufactured by Tokyo Electron Ltd., and dried on a hot plate at 110° C. for 90 seconds to obtain a resist film having a thickness of 50 nm. That is, a resist-coated mask blank was obtained.

[Production of Negative Resist Pattern]

This resist film was patternwise irradiated by using an electron beam lithography device (ELS-7500 manufactured by ELIONIX INC., accelerating voltage: 50 KeV). After the irradiation, the resist film was heated on a hot plate at 110° C. for 90 seconds, dipped in a 2.38 mass % aqueous tetramethylammonium hydroxide (TMAH) solution for 60 seconds, rinsed with water for 30 seconds and then dried.

[Evaluation of Resist Pattern]

The obtained pattern was evaluated for sensitivity, resolution, bridging margin, scum, and line edge roughness (LER) according to the following methods.

[Sensitivity]

The cross-sectional profile of the pattern obtained was observed using a scanning electron microscope (S-4300, manufactured by Hitachi, Ltd.). An exposure dose when resolving a 1:1 line and space resist pattern with a line width of 50 nm was taken as the sensitivity. A smaller value indicates higher sensitivity.

[L/S Resolution]

The limiting resolution (the minimum line width when the line and the space (line:space=1:1) were separated and resolved) at the exposure dose giving the sensitivity above was taken as the L/S resolution (nm).

[Bridging Margin]

At exposure of a line pattern having a line width of 50 nm, when the irradiation dose from the above sensitivity increasing, a space width beginning to exhibit occurrence of bridging between spaces was taken as an index of "bridging margin". A smaller value indicates a better performance.

[Isolated Space Pattern Resolution]

The limiting resolution (minimum space width permitting the separation and resolution of a line and a space) of isolated space (line:space=100:1) was determined at the above sensitivity. This value was denoted as the "isolated space pattern resolution (nm)". A smaller value indicates a better performance.

[Scum Evaluation]

In connection with the isolated space pattern resolution evaluation, the scum was evaluated in accordance with the following criteria.

A: No scum was observed.

B: Scum was observed in line width in the vicinity of limiting resolution.

C: Scum was observed in broader line width than limiting resolution.

[Line Edge Roughness (LER)]

A 1:1 line and space resist pattern having a line width of 50 nm was formed in an exposure dose giving the sensitivity above. Then, at arbitrary 30 points included in its longitudinal 50 μm region, the distance from a reference line where the edge should be present was measured using a scanning electron microscope (S-9220, manufactured by Hitachi, Ltd.). Thereafter, the standard deviation of the measured distances was determined, and 3 was calculated. A smaller value indicates a better performance.

TABLE 2

<EB Exposure; Alkali Developing; Negative>

| Examples | Resist composition | Sensitivity (μC/cm²) | LS resolution [nm] | Scum | Isolated space pattern resolution [nm] | Bridging margin [nm] | LER [nm] |
|---|---|---|---|---|---|---|---|
| Example 1 | R-1 | 20.3 | 20 | A | 25 | 75.0 | 4.3 |
| Example 2 | R-2 | 20.3 | 20 | A | 25 | 75.0 | 4.1 |
| Example 3 | R-3 | 21.1 | 20 | A | 25 | 75.0 | 4.2 |
| Example 4 | R-4 | 20.6 | 20 | A | 25 | 75.0 | 4.0 |
| Example 5 | R-5 | 20.1 | 20 | A | 25 | 75.0 | 4.2 |
| Example 6 | R-6 | 20.4 | 22.5 | A | 27.5 | 75.0 | 4.9 |
| Example 7 | R-7 | 20.4 | 22.5 | A | 27.5 | 75.0 | 4.6 |
| Example 8 | R-8 | 20.2 | 20 | A | 25 | 75.0 | 4.5 |
| Example 9 | R-9 | 20.4 | 20 | A | 25 | 75.0 | 4.4 |
| Example 10 | R-10 | 20.2 | 20 | A | 25 | 75.0 | 4.4 |
| Example 11 | R-11 | 20.9 | 20 | A | 25 | 75.0 | 4.0 |
| Example 12 | R-12 | 20.5 | 20 | A | 25 | 75.0 | 4.3 |

TABLE 2-continued

<EB Exposure; Alkali Developing; Negative>

| Examples | Resist composition | Sensitivity ($\mu C/cm^2$) | LS resolution [nm] | Scum | Isolated space pattern resolution [nm] | Bridging margin [nm] | LER [nm] |
|---|---|---|---|---|---|---|---|
| Example 13 | R-13 | 20.7 | 22.5 | A | 27.5 | 75.0 | 4.9 |
| Comparative Example 1 | R-14 | 22.1 | 30 | C | 35 | 100 | 5.5 |
| Comparative Example 2 | R-15 | 21.3 | 32 | C | 35 | 112.5 | 6.5 |
| Comparative Example 3 | R-16 | 20.9 | 31 | B | 35 | 87.5 | 6.2 |

<EUV Exposure; Negative; Alkali Developing>

[Preparation of Resist Coating Solution]

The same resist solution as the resist solution used in the above-mentioned EB exposure was prepared.

[Preparation of Resist Film]

The resist coating solution was coated on the above-described Cr oxide-deposited 6-inch wafer by using a spin coater, MARK 8, manufactured by Tokyo Electron Ltd., and dried on a hot plate at 110° C. for 90 seconds to obtain a resist film having a thickness of 50 nm. That is, a resist-coated mask blank was obtained.

[Production of Negative Resist Pattern]

This resist film was exposed to EUV light (wavelength: 13 nm) through a reflective mask of 1:1 line and space pattern having a line width of 50 nm and was then baked for 90 seconds at 110° C. Thereafter, the film was developed using a 2.38 mass % aqueous tetramethylammonium hydroxide (TMAH) solution.

[Evaluation of Resist Pattern]

The obtained resist pattern was evaluated for sensitivity, resolution, pattern profile, and line edge roughness (LER) according to the following methods.

[Sensitivity]

The cross-sectional profile of the pattern obtained was observed using a scanning electron microscope (S-4300, manufactured by Hitachi, Ltd.). An exposure dose when resolving a 1:1 line and space resist pattern with a line width of 50 nm was taken as the sensitivity. A smaller value indicates higher sensitivity.

[L/S Resolution]

The cross-sectional profile of the pattern obtained was observed using a scanning electron microscope (S-4300, manufactured by Hitachi, Ltd.). The limiting resolution (the minimum line width when the line and the space (line: space=1:1) were separated and resolved) at the exposure dose when resolving a 1:1 line and space resist pattern with a line width of 50 nm was taken as the resolution (nm).

[Scum Evaluation]

In connection with the isolated space pattern resolution evaluation, the scum was evaluated in accordance with the following criteria.

A: No scum was observed.

B: Scum was observed in line width in the vicinity of limiting resolution.

C: Scum was observed in broader line width than limiting resolution.

[Line Edge Roughness (LER)]

A 1:1 line and space resist pattern having a line width of 50 nm was formed in an exposure dose giving the sensitivity above. Then, at arbitrary 30 points included in its longitudinal 50 µm region, the distance from a reference line where the edge should be present was measured using a scanning electron microscope (S-9220, manufactured by Hitachi, Ltd.). Thereafter, the standard deviation of the measured distances was determined, and 3 σ was calculated. A smaller value indicates a better performance.

TABLE 3

<EUV; Alkali Developing; Negative>

| Examples | Resist composition | Sensitivity ($mJ/cm^2$) | LS resolution [nm] | Scum | LER [nm] |
|---|---|---|---|---|---|
| Example 14 | R-1 | 15.8 | 21 | A | 4.3 |
| Example 15 | R-2 | 15.6 | 21 | A | 4.1 |
| Example 16 | R-3 | 15.9 | 21 | A | 4.3 |
| Example 17 | R-4 | 15.7 | 20 | A | 4.0 |
| Example 18 | R-5 | 15.7 | 20 | A | 4.2 |
| Example 19 | R-6 | 15.6 | 23 | A | 4.9 |
| Example 20 | R-7 | 15.7 | 22 | A | 4.6 |
| Example 21 | R-8 | 15.8 | 20 | A | 4.2 |
| Example 22 | R-9 | 15.9 | 20 | A | 4.3 |
| Example 23 | R-10 | 15.8 | 21 | A | 4.4 |
| Example 24 | R-11 | 15.7 | 19 | A | 4.1 |
| Example 25 | R-12 | 16.1 | 21 | A | 4.3 |
| Example 26 | R-13 | 15.5 | 24 | A | 4.9 |
| Comparative Example 4 | R-14 | 16.3 | 31 | C | 5.3 |
| Comparative Example 5 | R-15 | 16.0 | 32 | C | 6.2 |
| Comparative Example 6 | R-16 | 15.8 | 32 | B | 6.1 |

What is claimed is:

1. An actinic ray-sensitive or radiation-sensitive resin composition, comprising:
   a crosslinking agent having a polarity converting group;
   an alkali-soluble resin; and
   a compound capable of generating an acid upon irradiation with actinic rays or radiation,
   wherein the polarity converting group is a group capable of decomposing by the action of an alkaline aqueous solution to generate a carboxylic acid or sulfonic acid which is bonded to a structure having the crosslinking group,
   wherein the alkali-soluble resin includes a repeating unit represented by the following General Formula (II) and a repeating unit represented by the following General Formula (3A), and
   wherein the crosslinking agent is a compound represented by General Formula (1), or a compound in which two to five structures represented by General Formula (1) are connected via a linking group or a single bond represented by L in General Formula (3),

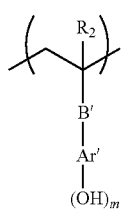

(II)

wherein in General Formula (II),
$R_2$ represents a hydrogen atom, a methyl group which may have a substituent, or a halogen atom,
B' represents a single bond or a divalent organic group,
Ar' represents an aromatic ring group, and
m represents an integer of 1 or more,

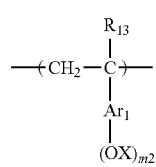

(3A)

in General Formula (3A),
$R_{13}$ represents a hydrogen atom or a methyl group,
X represents a non-acid-decomposable polycyclic alicyclic hydrocarbon structure bonded directly or via a divalent linking group to the oxygen,
$Ar_1$ represents an aromatic ring, and
m2 is an integer of 1 or more,

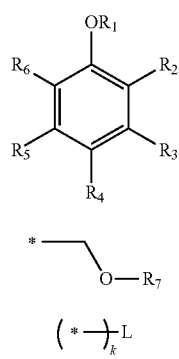

(1)

(2)

(3)

wherein in General Formula (1), $R_1$ represents a structure represented by any one of General Formulae (4) to (8), or a group containing the structure represented by any one of General Formulae (4) to (8), each of $R_2$ to $R_6$ independently represents a hydrogen atom, an organic group having 1 to 50 carbon atoms, or a binding site to a linking group or a single bond represented by L in General Formula (3), provided that at least one of $R_2$ to $R_6$ is a structure represented by General Formula (2), and at least one of $R_1$ to $R_6$ is a structure represented by any one of General Formulae (4) to (8), or a group containing the structure represented by any one of General Formulae (4) to (8),
in General Formula (2), $R_7$ represents a hydrogen atom or an organic group having 1 to 30 carbon atoms, and * represents a binding site in any one of $R_2$ to $R_6$, and in General Formula (3), L represents a linking group or a single bond, * represents a binding site in any one of $R_2$ to $R_6$, and k is an integer of 2 to 5,

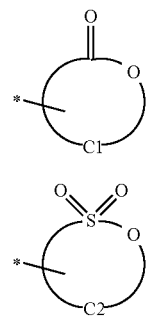

(4)

(5)

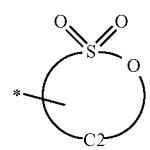

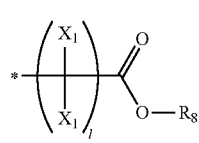

(6)

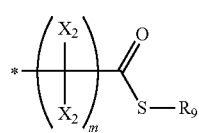

(7)

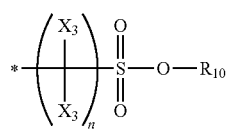

(8)

wherein in General Formula (4), C1 represents a hydrocarbon group having 1 to 15 carbon atoms and forms a monocyclic or polycyclic ring together with the —COO— group in the formula,
in General Formula (5), C2 represents a hydrocarbon group having 1 to 15 carbon atoms and forms a monocyclic or polycyclic ring together with the —$SO_3$— group in the formula,
in General Formula (6), each $X_1$ independently represents a hydrogen atom or a substituent, $R_8$ represents an alkyl group or an aryl group, and l represents an integer of 0 to 7, provided that in the case where $R_8$ is an alkyl group, the structure represented by General Formula (6) has at least one electron withdrawing group, and in the case where $R_8$ in this case is an alkyl group which does not have an electron withdrawing group, l is 1 or more, and at least one $X_1$ is an electron withdrawing group,
in General Formula (7), each $X_2$ independently represents a hydrogen atom or a substituent, $R_9$ represents an alkyl group or an aryl group, and m represents an integer of 0 to 7,
in General Formula (8), each $X_3$ independently represents a hydrogen atom or a substituent, $R_{10}$ represents an alkyl group or an aryl group, and n represents an integer of 0 to 7, and
in General Formulae (4) to (8), * represents a binding site.

2. The actinic ray-sensitive or radiation-sensitive resin composition according to claim 1, wherein the linking group L in General Formula (3) is a group selected from an alkylene group, an arylene group, a carboxylic acid ester bond, an ether bond, and combinations thereof.

3. The actinic ray-sensitive or radiation-sensitive resin composition according to claim 1, wherein the alkali-soluble resin includes at least a repeating unit represented by the following General Formula (12), as the repeating unit represented by General Formula (II),

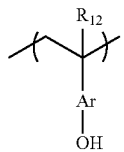
(12)

wherein in General Formula (12),
$R_{12}$ represents a hydrogen atom or a methyl group, and
Ar represents an aromatic ring group.

4. The actinic ray-sensitive or radiation-sensitive resin composition according to claim 1, further comprising a basic compound or ammonium salt compound whose basicity is decreased upon irradiation with actinic rays or radiation.

5. An actinic ray-sensitive or radiation-sensitive film comprised of the actinic ray-sensitive or radiation-sensitive resin composition according to claim 1.

6. A mask blank provided with the actinic ray-sensitive or radiation-sensitive film according to claim 5.

7. A pattern forming method, comprising:
forming the actinic ray-sensitive or radiation-sensitive film according to claim 5;
exposing the film; and
developing the exposed film using a developer to form a pattern.

8. The pattern forming method according to claim 7, wherein the exposure is carried out using X-rays, an electron beam, or EUV.

9. A method for manufacturing an electronic device, comprising the pattern forming method according to claim 7.

10. The actinic ray-sensitive or radiation-sensitive resin composition according to claim 1, further comprising a resin containing a repeating unit having an acid-crosslinkable group, represented by the following General Formula (1),

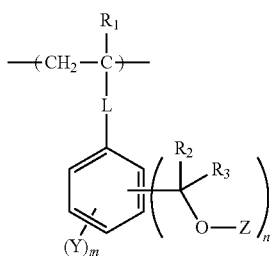
(1)

wherein in General Formula (1),
$R_1$ represents a hydrogen atom, a methyl group, or a halogen atom, $R_2$ and $R_3$ represent a hydrogen atom, an alkyl group, or a cycloalkyl group,
L represents a divalent linking group or a single bond,
Y represents a substituent except for a methylol group,
Z represents a hydrogen atom or a substituent,
m represents an integer of 0 to 4,
n represents an integer of 1 to 5, and
m+n is 5 or less.

11. A compound represented by the following General Formula (1), or a compound in which two or three structures represented by General Formula (1) are connected via a linking group or a single bond represented by L in General Formula (3a),

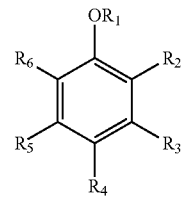
(1)

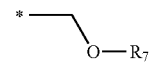
(2)

(3a)

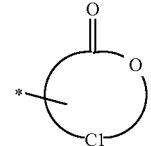
(4)

wherein in General Formula (1), $R_1$ represents a structure represented by General Formula (4), or a group containing the structure represented by General Formula (4), each of $R_2$ to $R_6$ independently represents a hydrogen atom, an organic group having 1 to 50 carbon atoms, or a binding site in which structures represented by General Formula (1) are connected via a linking group or a single bond represented by L in General Formula (3a), provided that at least one of $R_2$ to $R_6$ is a structure represented by General Formula (2), and at least one of $R_1$ to $R_6$ is a structure represented by General Formula (4), or a group containing the structure represented by General Formula (4),
in General Formula (2), $R_7$ represents a hydrogen atom or an organic group having 1 to 30 carbon atoms, and * represents a binding site in any one of $R_2$ to $R_6$,
in General Formula (3a), L represents a linking group or a single bond, * represents a binding site in any one of $R_2$ to $R_6$, and $k_1$ is 2 or 3, and
in General Formula (4), C1 represents a hydrocarbon group having 1 to 15 carbon atoms and forms a monocyclic or polycyclic ring together with a —COO— group in the formula.

* * * * *